(12) United States Patent
Martin et al.

(10) Patent No.: US 10,744,179 B2
(45) Date of Patent: Aug. 18, 2020

(54) METHOD FOR TREATMENT OF INFLAMMATORY SKIN DISORDERS WITH INHIBITORS OF IL-36 PROTEOLYTIC PROCESSING

(71) Applicant: THE PROVOST, FELLOWS, FOUNDATION SCHOLARS, & THE OTHER MEMBERS OF BOARD, OF THE COLLEGE OF THE HOLY, Dublin (IE)

(72) Inventors: Seamus J. Martin, Dublin (IE); Conor Henry, Dublin (IE); Graeme Sullivan, Dublin (IE)

(73) Assignee: THE PROVOST, FELLOWS, FOUNDATION SCHOLARS, & THE OTHER MEMBERS OF BOARD, OF THE COLLEGE OF THE HOLY, Dublin (IE)

( * ) Notice: Subject to any disclaimer, the term of this patent is extended or adjusted under 35 U.S.C. 154(b) by 8 days.

(21) Appl. No.: 15/512,139

(22) PCT Filed: Sep. 18, 2015

(86) PCT No.: PCT/EP2015/071446
§ 371 (c)(1),
(2) Date: Mar. 17, 2017

(87) PCT Pub. No.: WO2016/042131
PCT Pub. Date: Mar. 24, 2016

(65) Prior Publication Data
US 2017/0281716 A1    Oct. 5, 2017

(30) Foreign Application Priority Data
Sep. 18, 2014   (EP) .................................. 14185397

(51) Int. Cl.
| | |
|---|---|
| *A61K 38/06* | (2006.01) |
| *A61K 38/07* | (2006.01) |
| *A61K 38/05* | (2006.01) |
| *A61K 38/55* | (2006.01) |
| *A61K 31/10* | (2006.01) |
| *A61K 31/496* | (2006.01) |
| *A61K 31/137* | (2006.01) |
| *A61K 31/19* | (2006.01) |
| *A61K 31/713* | (2006.01) |
| *A61K 31/277* | (2006.01) |
| *A61K 31/495* | (2006.01) |
| *C07K 16/24* | (2006.01) |
| *A61K 39/395* | (2006.01) |
| *A61K 31/222* | (2006.01) |
| *A61K 31/675* | (2006.01) |
| *A61K 38/00* | (2006.01) |
| *C07K 16/40* | (2006.01) |

(52) U.S. Cl.
CPC .............. *A61K 38/07* (2013.01); *A61K 31/10* (2013.01); *A61K 31/137* (2013.01); *A61K 31/19* (2013.01); *A61K 31/222* (2013.01); *A61K 31/277* (2013.01); *A61K 31/495* (2013.01); *A61K 31/496* (2013.01); *A61K 31/675* (2013.01); *A61K 31/713* (2013.01); *A61K 38/005* (2013.01); *A61K 38/05* (2013.01); *A61K 38/06* (2013.01); *A61K 38/55* (2013.01); *A61K 39/3955* (2013.01); *C07K 16/244* (2013.01); *C07K 16/245* (2013.01); *C07K 16/40* (2013.01)

(58) Field of Classification Search
CPC ................................ A61K 38/06; A61K 38/07
See application file for complete search history.

(56) References Cited

U.S. PATENT DOCUMENTS

| 2004/0082544 A1 | 4/2004 | Greco et al. | |
|---|---|---|---|
| 2014/0044746 A1* | 2/2014 | Lange .................. | A61K 39/145 424/186.1 |
| 2015/0125438 A1* | 5/2015 | Kim ..................... | C12N 9/1276 424/94.5 |

FOREIGN PATENT DOCUMENTS

| DE | 102009004436 A1 | 4/2010 |
|---|---|---|
| EP | 0297362 A2 | 1/1989 |
| EP | 1493810 A1 | 1/2005 |
| EP | 2216047 A1 | 8/2010 |
| WO | 99/29339 A2 | 6/1999 |
| WO | 01/98365 A2 | 12/2001 |
| WO | 2008/106584 A1 | 9/2008 |

OTHER PUBLICATIONS

European Search Report of European Patent Application No. 14185397 dated Feb. 23, 2015.
Henriksen, P. A., "The potential of neutrophil elastase inhibitors as anti-inflammatory therapies", Current Opinion in Hematology, Jan. 1, 2014, pp. 23-28, vol. 21, No. 1.
(Continued)

*Primary Examiner* — Prema M Mertz
(74) *Attorney, Agent, or Firm* — McBee Moore & Vanik, IP, LLC

(57) ABSTRACT

This invention relates to the use of an agent capable of inhibiting IL-36 proteolytic processing for the treatment and/or reduction of inflammation in a subject. Advantageously, the agent prevents the production of a biologically active IL-36 to prevent and/or reduce the pro-inflammatory effects of IL-36. The invention also relates to a method for treatment and/or reduction of inflammation and compositions for treating and/or reducing inflammation.

14 Claims, 33 Drawing Sheets
Specification includes a Sequence Listing.

(56) References Cited

OTHER PUBLICATIONS

Hsieh, Pei-Wen et al., "The evaluation of 2,8-disubstituted benzoxazinone derivatives as anti-inflammatory and anti-platelet aggregation agents", Bioorganic & Medical Chemistry Letters, Jun. 2, 2005, pp. 2786-2789, vol. 15, No. 11.
Gresnigt, Mark S. et al., "Biology of IL-36 cytokines and their role in disease", Seminars in Immunology, 117 Dec. 2013, pp. 458-465, vol. 25, No. 6.
Database WPI, Thomson Scientific, London, GB, Dec. 11, 1991, XP002736329.
International Search Report of International Patent Application No. PCT/EP2015/071446 dated Nov. 30, 2015.
Database WPI, Thomson Scientific, London, GB, Nov. 28, 1989, XP002750861.
Sharma, Sushil K. et al., "Development of peptidomimetics targeting IAPs", International Journal of Peptide Research and Therapeutics, Jan. 1, 2006, pp. 21-32, vol. 12, No. 1.
Tseng, W A et al., "NLRP3 Inflammasome Activation in Retinal Pigment Epithelial Cells by Lysosomal Destabilization: Implications for Age-Related Macular Degeneration", Investigative Ophthalmology and Visual Science, Jan. 7, 2017, pp. 110-120, vol. 54, No. 1.

* cited by examiner

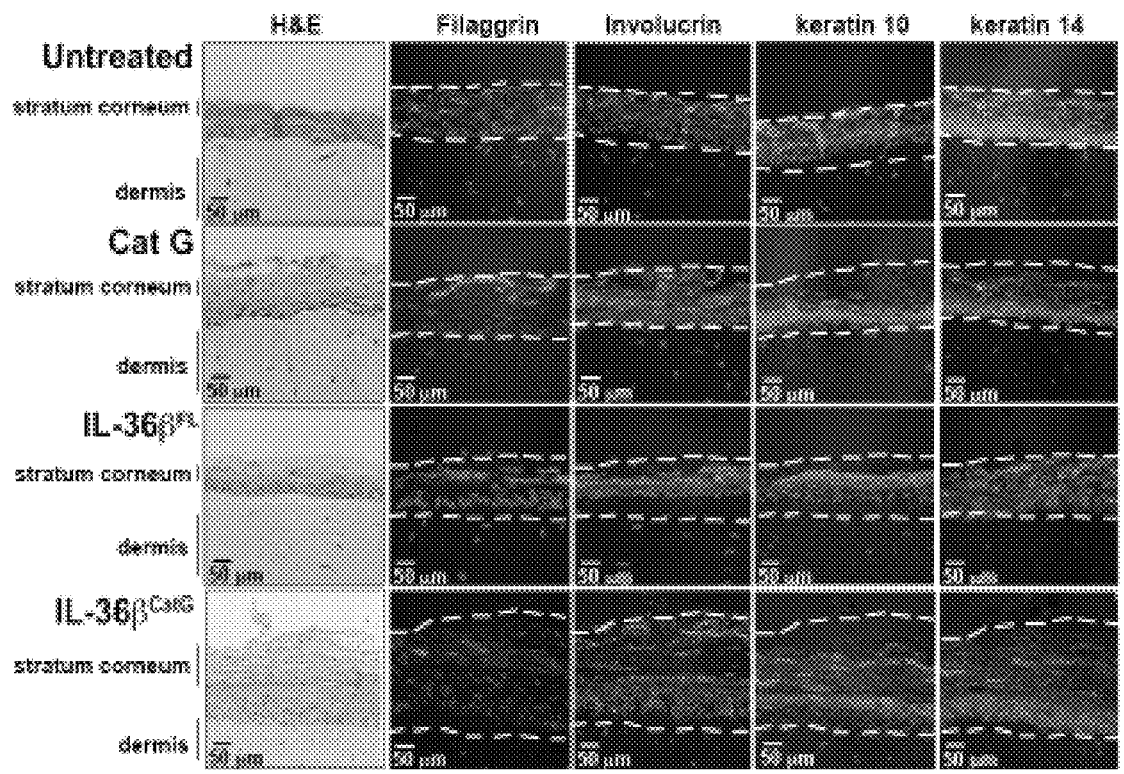
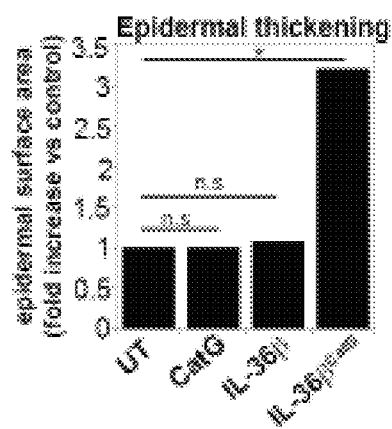
Fig.18

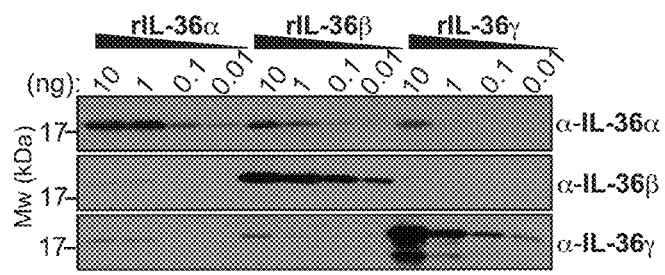
Fig.22
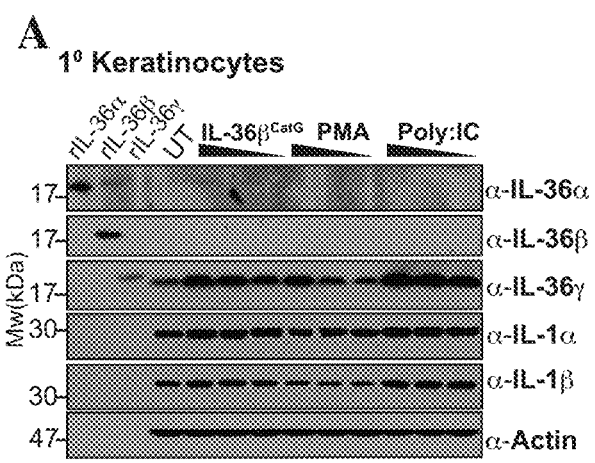
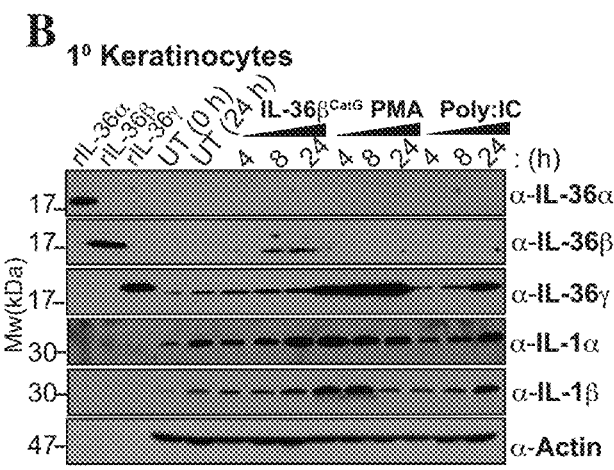
Fig.23

```
                9                   18                  27                  36                  45                  54
ATG AAC CCA CAA CGG GAG GCA GCA CCC AAA TCC TAT GCT ATT CGT GAT TCT CGA
 M   N   P   Q   R   E   A   A   P   K   S   Y   A   I   R   D   S   R 63                  72                  81                  90                  99                 108
CAG ATG GTG TGG GTC CTG AGT GGA AAT TCT TTA ATA GCA GCT CCT CTT AGC CGC
 Q   M   V   W   V   L   S   G   N   S   L   I   A   A   P   L   S   R 117                 126                 135                 144                 153                 162
AGC ATT AAG CCT GTC ACT CTT CAT TTA ATA GCC TGT AGA GAC ACA GAA TTC AGT
 S   I   K   P   V   T   L   H   L   I   A   C   R   D   T   E   F   S 171                 180                 189                 198                 207                 216
GAC AAG GAA AAG GGT AAT ATG GTT TAC CTG GGA ATC AAG GGA AAA GAT CTC TGT
 D   K   E   K   G   N   M   V   Y   L   G   I   K   G   K   D   L   C 225                 234                 243                 252                 261                 270
CTC TTC TGT GCA GAA ATT CAG GGC AAG CCT ACT TTG CAG CTT AAG GAA AAA AAT
 L   F   C   A   E   I   Q   G   K   P   T   L   Q   L   K   E   K   N 279                 288                 297                 306                 315                 324
ATC ATG GAC CTG TAT GTG GAG AAG AAA GCA CAG AAG CCC TTT CTC TTT TTC CAC
 I   M   D   L   Y   V   E   K   K   A   Q   K   P   F   L   F   F   H 333                 342                 351                 360                 369                 378
AAT AAA GAA GGC TCC ACT TCT GTC TTT CAG TCA GTC TCT TAC CCT GGC TGG TTC
 N   K   E   G   S   T   S   V   F   Q   S   V   S   Y   P   G   W   F 387                 396                 405                 414                 423                 432
ATA GCC ACC TCC ACC ACA TCA GGA CAG CCC ATC TTT CTC ACC AAG GAG AGA GGC
 I   A   T   S   T   T   S   G   Q   P   I   F   L   T   K   E   R   G 441                 450                 459                 468
ATA ACT AAT AAC ACT AAC TTC TAC TTA GAT TCT GTG GAA TAA 3'
 I   T   N   N   T   N   F   Y   L   D   S   V   E   *
```

Fig.36

```
          9              18             27             36             45             54
5' ATG AGA GGC ACT CCA GGA GAC GCT GAT GGT GGA AGG GCC GTC TAT CAA TCA
    M   R   G   T   P   G   D   A   D   G   G   R   A   V   Y   Q   S 63             72             81             90             99            108
   ATG TGT AAA CCT ATT ACT GGG ACT ATT AAT GAT TTG AAT CAG CAA GTG TGG ACC
    M   C   K   P   I   T   G   T   I   N   D   L   N   Q   Q   V   W   T 117            126            135            144            153            162
   CTT CAG GGT CAG AAC CTT GTG GCA GTT CCA CGA AGT GAC AGT GTG ACC CCA GTC
    L   Q   G   Q   N   L   V   A   V   P   R   S   D   S   V   T   P   V 171            180            189            198            207            216
   ACT GTT GCT GTT ATC ACA TGC AAG TAT CCA GAG GCT CTT GAG CAA GGC AGA GGG
    T   V   A   V   I   T   C   K   Y   P   E   A   L   E   Q   G   R   G 225            234            243            252            261            270
   GAT CCC ATT TAT TTG GGA ATC CAG AAT CCA GAA ATG TGT TTG TAT TGT GAG AAG
    D   P   I   Y   L   G   I   Q   N   P   E   M   C   L   Y   C   E   K 279            288            297            306            315            324
   GTT GGA GAA CAG CCC ACA TTG CAG CTA AAA GAG CAG AAG ATC ATG GAT CTG TAT
    V   G   E   Q   P   T   L   Q   L   K   E   Q   K   I   M   D   L   Y 333            342            351            360            369            378
   GGC CAA CCC GAG CCC GTG AAA CCC TTC CTT TTC TAC CGT GCC AAG ACT GGT AGG
    G   Q   P   E   P   V   K   P   F   L   F   Y   R   A   K   T   G   R 387            396            405            414            423            432
   ACC TCC ACC CTT GAG TCT GTG GCC TTC CCG GAC TGG TTC ATT GCC TCC TCC AAG
    T   S   T   L   E   S   V   A   F   P   D   W   F   I   A   S   S   K 441            450            459            468            477            486
   AGA GAC CAG CCC ATC ATT CTG ACT TCA GAA CTT GGG AAG TCA TAC AAC ACT GCC
    R   D   Q   P   I   I   L   T   S   E   L   G   K   S   Y   N   T   A 495            504
   TTT GAA TTA AAT ATA AAT GAC TGA 3'
    F   E   L   N   I   N   D   *
```

Fig.37

ATG GAA AAA GCA TTG AAA ATT GAC ACA CCT CAG CAG GGG AGC ATT CAG GAT ATC
 M   E   K   A   L   K   I   D   T   P   Q   Q   G   S   I   Q   D   I

AAT CAT CGG GTG TGG GTT CTT CAG GAC CAG ACG CTC ATA GCA GTC CCG AGG AAG
 N   H   R   V   W   V   L   Q   D   Q   T   L   I   A   V   P   R   K

GAC CGT ATG TCT CCA GTC ACT ATT GCC TTA ATC TCA TGC CGA CAT GTG GAG ACC
 D   R   M   S   P   V   T   I   A   L   I   S   C   R   H   V   E   T

CTT GAG AAA GAC AGA GGG AAC CCC ATC TAC CTG GGC CTG AAT GGA CTC AAT CTC
 L   E   K   D   R   G   N   P   I   Y   L   G   L   N   G   L   N   L

TGC CTG ATG TGT GCT AAA GTC GGG GAC CAG CCC ACA CTG CAG CTG AAG GAA AAG
 C   L   M   C   A   K   V   G   D   Q   P   T   L   Q   L   K   E   K

GAT ATA ATG GAT TTG TAC AAC CAA CCC GAG CCT GTG AAG TCC TTT CTC TTC TAC
 D   I   M   D   L   Y   N   Q   P   E   P   V   K   S   F   L   F   Y

CAC AGC CAG AGT GGC AGG AAC TCC ACC TTC GAG TCT GTG GCT TTC CCT GGC TGG
 H   S   Q   S   G   R   N   S   T   F   E   S   V   A   F   P   G   W

TTC ATC GCT GTC AGC TCT GAA GGA GGC TGT CCT CTC ATC CTT ACC CAA GAA
 F   I   A   V   S   S   E   G   G   C   P   L   I   L   T   Q   E

CTG GGG AAA GCC AAC ACT ACT GAC TTT GGG TTA ACT ATG CTG TTT TAA
 L   G   K   A   N   T   T   D   F   G   L   T   M   L   F   *

Fig.38

SEQUENCE LISTING

```
<160> NUMBER OF SEQ ID NOS: 33

<210> SEQ ID NO 1
<211> LENGTH: 8
<212> TYPE: PRT
<213> ORGANISM: Homo sapiens

<400> SEQUENCE: 1

Asn Pro Gln Arg Glu Ala Pro Pro
1               5

<210> SEQ ID NO 2
<211> LENGTH: 8
<212> TYPE: PRT
<213> ORGANISM: Homo sapiens

<400> SEQUENCE: 2

Gly Arg Ala Val Tyr Gln Ser Met
1               5

<210> SEQ ID NO 3
<211> LENGTH: 474
<212> TYPE: DNA
<213> ORGANISM: Homo sapiens
```

<400> SEQUENCE: 3

```
atgaacccac aacgggaggc agcacccaaa tcctatgcta ttcgtgattc tcgacagatg      60
gtgtgggtcc tgagtggaaa ttctttaata gcagctcctc ttagccgcag cattaagcct     120
gtcactcttc atttaatagc ctgtagagac acagaattca gtgacaagga aaagggtaat     180
atggtttacc tgggaatcaa gggaaaagat ctctgtctct tctgtgcaga aattcagggc     240
aagcctactt tgcagcttaa ggaaaaaaat atcatggacc tgtatgtgga agagaaagca     300
cagaagccct ttctcttttt ccacaataaa gaaggctcca cttctgtctt tcagtcagtc     360
tcttaccctg gctggttcat agccacctcc accacatcag acagcccat  ctttctcacc     420
aaggagagag gcataactaa taacactaac ttctacttag attctgtgga ataa           474
```

<210> SEQ ID NO 4
<211> LENGTH: 157
<212> TYPE: PRT
<213> ORGANISM: Homo sapiens

<400> SEQUENCE: 4

```
Met Asn Pro Gln Arg Glu Ala Ala Pro Lys Ser Tyr Ala Ile Arg Asp
1               5                   10                  15

Ser Arg Gln Met Val Trp Val Leu Ser Gly Asn Ser Leu Ile Ala Ala
            20                  25                  30

Pro Leu Ser Arg Ser Ile Lys Pro Val Thr Leu His Leu Ile Ala Cys
        35                  40                  45

Arg Asp Thr Glu Phe Ser Asp Lys Glu Lys Gly Asn Met Val Tyr Leu
    50                  55                  60

Gly Ile Lys Gly Lys Asp Leu Cys Leu Phe Cys Ala Glu Ile Gln Gly
65                  70                  75                  80

Lys Pro Thr Leu Gln Leu Lys Glu Lys Asn Ile Met Asp Leu Tyr Val
                85                  90                  95

Glu Lys Lys Ala Gln Lys Pro Phe Leu Phe Phe His Asn Lys Glu Gly
            100                 105                 110

Ser Thr Ser Val Phe Gln Ser Val Ser Tyr Pro Gly Trp Phe Ile Ala
        115                 120                 125

Thr Ser Thr Thr Ser Gly Gln Pro Ile Phe Leu Thr Lys Glu Arg Gly
    130                 135                 140

Ile Thr Asn Asn Thr Asn Phe Tyr Leu Asp Ser Val Glu
145                 150                 155
```

<210> SEQ ID NO 5
<211> LENGTH: 510
<212> TYPE: DNA
<213> ORGANISM: Homo sapiens

<400> SEQUENCE: 5

```
atgagaggca ctccaggaga cgctgatggt ggaggaaggg ccgtctatca atcaatgtgt      60
aaacctatta ctgggactat taatgatttg aatcagcaag tgtggaccct tcagggtcag     120
aaccttgtgg cagttccacg aagtgacagt gtgaccccag tcactgttgc tgttatcaca     180
tgcaagtatc cagaggctct tgagcaaggc agaggggatc ccatttattt gggaatccag     240
aatccagaaa tgtgtttgta ttgtgagaag gttggagaac agcccacatt gcagctaaaa     300
gagcagaaga tcatggatct gtatggccaa cccgagcccg tgaaacccct ccttttctac     360
cgtgccaaga ctggtaggac ctccacccct gagtctgtgg ccttcccgga ctggttcatt     420
```

```
gcctcctcca agagagacca gcccatcatt ctgacttcag aacttgggaa gtcatacaac    480
actgcctttg aattaaatat aaatgactga                                     510
```

<210> SEQ ID NO 6
<211> LENGTH: 169
<212> TYPE: PRT
<213> ORGANISM: Homo sapiens

<400> SEQUENCE: 6

```
Met Arg Gly Thr Pro Gly Asp Ala Asp Gly Gly Arg Ala Val Tyr
1               5                   10                  15

Gln Ser Met Cys Lys Pro Ile Thr Gly Thr Ile Asn Asp Leu Asn Gln
            20                  25                  30

Gln Val Trp Thr Leu Gln Gly Gln Asn Leu Val Ala Val Pro Arg Ser
                35                  40                  45

Asp Ser Val Thr Pro Val Thr Val Ala Val Ile Thr Cys Lys Tyr Pro
        50                  55                  60

Glu Ala Leu Glu Gln Gly Arg Gly Asp Pro Ile Tyr Leu Gly Ile Gln
65                  70                  75                  80

Asn Pro Glu Met Cys Leu Tyr Cys Glu Lys Val Gly Glu Gln Pro Thr
                85                  90                  95

Leu Gln Leu Lys Glu Gln Lys Ile Met Asp Leu Tyr Gly Gln Pro Glu
            100                 105                 110

Pro Val Lys Pro Phe Leu Phe Tyr Arg Ala Lys Thr Gly Arg Thr Ser
                115                 120                 125

Thr Leu Glu Ser Val Ala Phe Pro Asp Trp Phe Ile Ala Ser Ser Lys
    130                 135                 140

Arg Asp Gln Pro Ile Ile Leu Thr Ser Glu Leu Gly Lys Ser Tyr Asn
145                 150                 155                 160

Thr Ala Phe Glu Leu Asn Ile Asn Asp
                165
```

<210> SEQ ID NO 7
<211> LENGTH: 4
<212> TYPE: PRT
<213> ORGANISM: Artificial Sequence
<220> FEATURE:
<223> OTHER INFORMATION: tetrepeptide

<400> SEQUENCE: 7

```
Ala Phe Leu Phe
1
```

<210> SEQ ID NO 8
<211> LENGTH: 4
<212> TYPE: PRT
<213> ORGANISM: Artificial Sequence
<220> FEATURE:
<223> OTHER INFORMATION: tetrapeptide

<400> SEQUENCE: 8

```
Asp Thr Glu Phe
1
```

<210> SEQ ID NO 9
<211> LENGTH: 6
<212> TYPE: PRT
<213> ORGANISM: Artificial Sequence
<220> FEATURE:
<223> OTHER INFORMATION: synthetic peptide
<220> FEATURE:

```
<221> NAME/KEY: MISC_FEATURE
<222> LOCATION: (1)..(1)
<223> OTHER INFORMATION: Xaa is Ac
<220> FEATURE:
<221> NAME/KEY: MISC_FEATURE
<222> LOCATION: (6)..(6)
<223> OTHER INFORMATION: Xaa is AMC

<400> SEQUENCE: 9

Xaa Asp Glu Val Asp Xaa
1               5

<210> SEQ ID NO 10
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is Ac
<220> FEATURE:
<221> NAME/KEY: MISC_FEATURE
<222> LOCATION: (6)..(6)
<223> OTHER INFORMATION: Xaa is AMC

<400> SEQUENCE: 10

Xaa Trp Glu His Asp Xaa
1               5

<210> SEQ ID NO 11
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is Suc(oMe)
<220> FEATURE:
<221> NAME/KEY: MISC_FEATURE
<222> LOCATION: (6)..(6)
<223> OTHER INFORMATION: Xaa is AMC

<400> SEQUENCE: 11

Xaa Ala Ala Pro Val Xaa
1               5

<210> SEQ ID NO 12
<211> LENGTH: 19
<212> TYPE: DNA
<213> ORGANISM: Artificial Sequence
<220> FEATURE:
<223> OTHER INFORMATION: IL-17C Forward

<400> SEQUENCE: 12
ttggaggcag acacccacc                                            19

<210> SEQ ID NO 13
<211> LENGTH: 20
<212> TYPE: DNA
<213> ORGANISM: Artificial Sequence
<220> FEATURE:
<223> OTHER INFORMATION: IL-17C Reverse

<400> SEQUENCE: 13
gatagcggtc ctcatccgtg                                           20
```

```
<210> SEQ ID NO 14
<211> LENGTH: 23
<212> TYPE: DNA
<213> ORGANISM: Artificial Sequence
<220> FEATURE:
<223> OTHER INFORMATION: IL-36 Forward

<400> SEQUENCE: 14
gaaacccttc cttttctacc gtg                                              23

<210> SEQ ID NO 15
<211> LENGTH: 20
<212> TYPE: DNA
<213> ORGANISM: Artificial Sequence
<220> FEATURE:
<223> OTHER INFORMATION: IL-36 Reverse

<400> SEQUENCE: 15
gctggtctct cttggaggag                                                  20

<210> SEQ ID NO 16
<211> LENGTH: 20
<212> TYPE: DNA
<213> ORGANISM: Artificial Sequence
<220> FEATURE:
<223> OTHER INFORMATION: IL-8 Forward

<400> SEQUENCE: 16
tctgcagctc tgtgtgaagg                                                  20

<210> SEQ ID NO 17
<211> LENGTH: 20
<212> TYPE: DNA
<213> ORGANISM: Artificial Sequence
<220> FEATURE:
<223> OTHER INFORMATION: IL-8 Reverse

<400> SEQUENCE: 17
acttctccac aaccctctga                                                  20

<210> SEQ ID NO 18
<211> LENGTH: 20
<212> TYPE: DNA
<213> ORGANISM: Artificial Sequence
<220> FEATURE:
<223> OTHER INFORMATION: G-CSF Forward

<400> SEQUENCE: 18
gcttagagca agtgaggaag                                                  20

<210> SEQ ID NO 19
<211> LENGTH: 20
<212> TYPE: DNA
<213> ORGANISM: Artificial Sequence
<220> FEATURE:
<223> OTHER INFORMATION: G-CSF Reverse

<400> SEQUENCE: 19
aggtggcgta gaacgcggta                                                  20

<210> SEQ ID NO 20
<211> LENGTH: 24
<212> TYPE: PRT
<213> ORGANISM: Artificial Sequence
<220> FEATURE:
<223> OTHER INFORMATION: GM-CSF Forward
```

```
<400> SEQUENCE: 20

Gly Ala Gly Cys Ala Thr Gly Thr Gly Ala Thr Gly Cys Cys Ala
1               5                   10                  15

Thr Cys Cys Ala Gly Gly Ala Gly
                20

<210> SEQ ID NO 21
<211> LENGTH: 27
<212> TYPE: DNA
<213> ORGANISM: Artificial Sequence
<220> FEATURE:
<223> OTHER INFORMATION: GM-CSF Reverse

<400> SEQUENCE: 21
ctcctggact ggctcccagc agtcaaa                                       27

<210> SEQ ID NO 22
<211> LENGTH: 20
<212> TYPE: DNA
<213> ORGANISM: Artificial Sequence
<220> FEATURE:
<223> OTHER INFORMATION: beta-defensin-2 Forward

<400> SEQUENCE: 22
atgagggtct tgtatctcct                                               20

<210> SEQ ID NO 23
<211> LENGTH: 20
<212> TYPE: DNA
<213> ORGANISM: Artificial Sequence
<220> FEATURE:
<223> OTHER INFORMATION: beta -defensin-2 Reverse

<400> SEQUENCE: 23
tatctttgga caccatagtt                                               20

<210> SEQ ID NO 24
<211> LENGTH: 20
<212> TYPE: DNA
<213> ORGANISM: Artificial Sequence
<220> FEATURE:
<223> OTHER INFORMATION: beta-Actin Forward

<400> SEQUENCE: 24
atgtttgaga ccttcaacac                                               20

<210> SEQ ID NO 25
<211> LENGTH: 20
<212> TYPE: DNA
<213> ORGANISM: Artificial Sequence
<220> FEATURE:
<223> OTHER INFORMATION: beta-Actin Reverse

<400> SEQUENCE: 25
cacgtcacac ttcatgatgg                                               20

<210> SEQ ID NO 26
<211> LENGTH: 477
<212> TYPE: DNA
<213> ORGANISM: Homo sapiens

<400> SEQUENCE: 26
atggaaaaag cattgaaaat tgacacacct cagcagggga gcattcagga tatcaatcat    60
```

```
cgggtgtggg ttcttcagga ccagacgctc atagcagtcc cgaggaagga ccgtatgtct    120
ccagtcacta ttgccttaat ctcatgccga catgtggaga cccttgagaa agacagaggg    180
aaccccatct acctgggcct gaatggactc aatctctgcc tgatgtgtgc taaagtcggg    240
gaccagccca cactgcagct gaaggaaaag gatataatgg atttgtacaa ccaacccgag    300
cctgtgaagt cctttctctt ctaccacagc cagagtggca ggaactccac cttcgagtct    360
gtggctttcc ctggctggtt catcgctgtc agctctgaag gaggctgtcc tctcatcctt    420
acccaagaac tggggaaagc caacactact gactttgggt taactatgct gttttaa       477
```

<210> SEQ ID NO 27
<211> LENGTH: 158
<212> TYPE: PRT
<213> ORGANISM: Homo sapiens

<400> SEQUENCE: 27

```
Met Glu Lys Ala Leu Lys Ile Asp Thr Pro Gln Gln Gly Ser Ile Gln
1               5                   10                  15

Asp Ile Asn His Arg Val Trp Val Leu Gln Asp Gln Thr Leu Ile Ala
            20                  25                  30

Val Pro Arg Lys Asp Arg Met Ser Pro Val Thr Ile Ala Leu Ile Ser
        35                  40                  45

Cys Arg His Val Glu Thr Leu Glu Lys Asp Arg Gly Asn Pro Ile Tyr
    50                  55                  60

Leu Gly Leu Asn Gly Leu Asn Leu Cys Leu Met Cys Ala Lys Val Gly
65                  70                  75                  80

Asp Gln Pro Thr Leu Gln Leu Lys Glu Lys Asp Ile Met Asp Leu Tyr
                85                  90                  95

Asn Gln Pro Glu Pro Val Lys Ser Phe Leu Phe Tyr His Ser Gln Ser
            100                 105                 110

Gly Arg Asn Ser Thr Phe Glu Ser Val Ala Phe Pro Gly Trp Phe Ile
        115                 120                 125

Ala Val Ser Ser Glu Gly Gly Cys Pro Leu Ile Leu Thr Gln Glu Leu
    130                 135                 140

Gly Lys Ala Asn Thr Thr Asp Phe Gly Leu Thr Met Leu Phe
145                 150                 155
```

<210> SEQ ID NO 28
<211> LENGTH: 8
<212> TYPE: PRT
<213> ORGANISM: Homo sapiens

<400> SEQUENCE: 28

```
Met Glu Lys Ala Leu Lys Ile Asp
1               5
```

<210> SEQ ID NO 29
<211> LENGTH: 4
<212> TYPE: PRT
<213> ORGANISM: Artificial Sequence
<220> FEATURE:
<223> OTHER INFORMATION: tetrapeptide

<400> SEQUENCE: 29

```
Met Ala Leu Ala
1
```

<210> SEQ ID NO 30
<211> LENGTH: 4

```
<212> TYPE: PRT
<213> ORGANISM: Artificial Sequence
<220> FEATURE:
<223> OTHER INFORMATION: tetrapeptide

<400> SEQUENCE: 30

Asn Pro Gln Arg
1

<210> SEQ ID NO 31
<211> LENGTH: 4
<212> TYPE: PRT
<213> ORGANISM: Artificial Sequence
<220> FEATURE:
<223> OTHER INFORMATION: tetrapeptide

<400> SEQUENCE: 31

Gln Arg Glu Ala
1

<210> SEQ ID NO 32
<211> LENGTH: 4
<212> TYPE: PRT
<213> ORGANISM: Artificial Sequence
<220> FEATURE:
<223> OTHER INFORMATION: tetrapeptide

<400> SEQUENCE: 32

Gly Arg Ala Val
1

<210> SEQ ID NO 33
<211> LENGTH: 4
<212> TYPE: PRT
<213> ORGANISM: Artificial Sequence
<220> FEATURE:
<223> OTHER INFORMATION: tetrapeptide

<400> SEQUENCE: 33

Ala Val Tyr Gln
1
```

METHOD FOR TREATMENT OF INFLAMMATORY SKIN DISORDERS WITH INHIBITORS OF IL-36 PROTEOLYTIC PROCESSING

CROSS-REFERENCE TO RELATED APPLICATIONS

This application is a National Stage entry of International Application No. PCT/EP2015/071446, filed 18 Sep. 2015, which claims priority to European Patent Application No. 14185397.8, filed 18 Sep. 2014.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_3000036-002000_ST25.txt" created on 13 Mar. 2017, and 12,069 bytes in size) is submitted concurrently with the instant application, and the entire contents of the Sequence Listing are incorporated herein by reference.

BACKGROUND

Field

This invention relates to the use of an agent capable of inhibiting interleukin-36 (IL-36) proteolytic processing for the treatment and/or reduction of inflammation in a subject. The invention also relates to a method for treatment and/or reduction of inflammation and compositions for treating and/or reducing inflammation.

Description of Related Art

Inflammation of barrier organs, including the gut, lung and skin can result in many undesirable chronic long term conditions including inflammatory skin conditions, inflammatory bowel disease and associated conditions of Crohn's disease, ulcerative colitis, and colorectal cancer and chronic obstructive pulmonary disease. These conditions tend to be difficult to treat and costly from both a long-term management and healthcare perspective. New ways of effectively treating these chronic and long-term conditions are of great importance.

Inflammation of barrier organs in a subject includes inflammation of the skin, gut and/or lung. For example, inflammatory skin conditions typically present as heterogenous conditions with disease subtypes displaying varying degrees of severity, from mild itching to grave medical health complications. They are characterized by irritation and excessive inflammation of the skin. These diseases may sometimes be disfiguring and can cause great discomfort to the affected individual. Inflammatory skin conditions include psoriasis such as plaque psoriasis, guttate psoriasis, flexural (inverse) psoriasis, erythroderma psoriasis, generalized pustular psoriasis, palmoplanter pustulosis, psoriatic nail disease, sebaceous cysts, vasculitis, eczema, dermatitis, granuloma annulare, lichen planus, bullous pemphigoid, molluscum contagiosum, dermatomyositis, acne and ichthyosis vulgaris.

What underpins this heterogeneity is not clear in many cases but some inflammatory conditions have a clear genetic component that predisposes particular individuals to spontaneous autoinflammatory disease or exacerbates immune reactions to infectious agents[1-2]. In severe cases, such as in mongenic autoinflammatory disease, the genetic perturbation can be mapped to loss-of-function or severe hypomorphic mutations in single genes, such as NLPR3 in cryopyrin-associated periodic syndromes (CAPS), deficiency in IL-1R antagonist (DIRA) and Deficiency in IL-36R antagonist (DITRA)[1-2]. In both of the latter examples, there is extreme hypersensitivity to disturbance of the skin barrier, the first line of defence against injury or infection. As a consequence, such individuals frequently display severe and life threatening autoinflammatory diseases such as generalized pustular psoriasis, pustulosis or stomatitis[1]. The underlying genetic basis of elevated pro-inflammatory responses in other immune diseases are somewhat less obvious and typically includes deregulation of multiple inflammatory pathways and environmental components, but nonetheless leads to heightened and prolonged immune responses that lead to conditions such as psoriasis, dermatitis, inflammatory bowel diseases and rheumatoid arthritis. However, it is becoming increasingly clear that particular cytokines, such as members of the extended IL-1 family and TNF, play central roles in initiating and/or sustaining many of these autoimmune/autoinflammatory conditions.

Psoriasis is a common inflammatory skin condition that effects approximately 1-3% of the Caucasian population[3]. The most prevalent form of this condition, plaque psoriasis, accounts for approximately 80% of cases. Of those, the related, psoriatic arthritis is encountered in 5-30% of individuals. Palmoplanter psoriasis is encountered in about 10% of psoriasis patients and a life-threatening severe form of psoriasis, Generalized Pustular Psoriasis (GPP), accounts for less than 5% of cases[3]. Psoriasis is characterised by hyperproliferation and impaired differentiation of keratinocytes, the most abundant cell type in the skin, leading to thickening of the skin in lesional areas (acanthosis). It is well established that psoriasis features excessive inflammatory reactions in the skin, as a result of innate as well as adaptive immune cell types that result in the pathological features of psoriasis. While the triggering events remain unclear, skin damage, viral and bacterial infection (e.g streptococcal bacteria in the throat) and inherited genetic susceptibilities are all major factors[4-5].

Current treatment for psoriasis include the use of agents such as anthralin (dihydroxyanthralin), azarabine, colchicine, fluorouracil, methotrexate, methoxsalen (8-methoxypsoralen), resorcinol, retinoids (for example, retinoic acid), corticosteroids (for example, clobetasol propionate, trimcinolone acetonide and the like), cyclosporin, iodochlorhydroxyquin, salicyclic acid, vitamin D, dapsone, somatostatin, sulfur, tars and zinc oxide. Ultra-violet light treatment, alone or in combination with other agents such as psoralen (i.e., PUVA treatment), is also used to treat psoriasis[3]. Because of the critical role that cytokines play in driving inflammation, and by extension the pathological effects associated with excessive inflammation, apical cytokines and their downstream effectors represent very attractive therapeutic targets. Cytokine-targeted biologics are highly specific with minimal off-target effects or toxicity. As a consequence, there has been a revolution in the development of cytokine-targeted biological therapies using neutralizing antibodies or receptor-IgFc fusion proteins over the past decade. In particular, TNF neutralization has been transformative in the treatment of several inflammatory diseases[6-7], and neutralization approaches targeted against IL-12/IL-23, IL-17, and IL-4 have entered the clinic or are on clinical trials at present. In particular, IL-12/IL-23 and IL-17 neutralizing antibodies have shown great efficacy in the treatment of moderate to severe forms (>10% surface area affected) of psoriasis during clinical trials[8].

IL-1 family cytokines, which include the recently described IL-36α, β and γ proteins, play major roles as initiators of inflammation and are frequently among the first cytokines produced in response to infection or injury[9-11]. IL-1 cytokines are capable of triggering complex cascades of additional cytokine production from diverse cells types, such as resident tissue macrophages and dendritic cells, as well as keratinocytes and endothelial cells lining local blood vessels[12-14]. IL-36α, IL-36β and IL-36γ are encoded by distinct genes and evidence is rapidly accumulating to suggest that these cytokines play a key role in skin inflammation, particularly in psoriasis[15].

Individuals that carry hypomorphic mutations in the IL-36 receptor antagonist (IL-36RA) display a severe and highly debilitating form of psoriasis, called generalized pustular psoriasis[1,16-18]. This suggests that deregulated IL-36 cytokine signaling is sufficient to drive aggressive skin inflammation and also that IL-36 is an important barrier cytokine. Moreover, analysis of IL-36 mRNA expression in skin biopsies from individuals with the most common form of psoriasis, psoriasis vulgaris, found dramatically elevated expression (100-fold) of all three IL-36 transcripts compared with non-lesional skin from the same individuals, or non-affected controls[19]. Consistent with the idea that elevated IL-36 activity is an initiating event in psoriasis, transgenic expression of IL-36α in the mouse leads to a psoriasis-like condition at birth that can be further exacerbated with the skin irritant, phorbol acetate[20-21]. Application of a toll receptor agonist (imiquomod) to the skin in humans and mice can provoke psoriasis outbreaks[23], which are increased in severity in IL-36RA$^{-/-}$ mice[22]. Furthermore, imiquomod-induced psoriasis in mouse models is completely abolished on an IL-36R$^{-/-}$ background[22], and transplantation of human psoriatic lesions onto immunodeficient (SCID) mice produces a psoriasis-like condition that is greatly improved through blocking the IL-36 receptor[20].

IL-36α, IL-36β and IL-36γ are all generated as leaderless cytokines that lack biological activity[24]. Thus, proteolytic processing of IL-36 proteins is required to unlock the pro-inflammatory potential of these cytokines, similar to other members of the IL-1 family, such as IL-1β and IL-18. Sims and colleagues[24] have shown that removal of a small number of residues from the N-termini of IL-36α, IL-36β and IL-36γ increases their biological activity by greater than 10,000-fold. Because IL-36 cytokines appear to play a key role as initiators of inflammation in the skin barrier, inhibitors of IL-36 activation are therefore likely to have considerable potential for the treatment of inflammatory skin conditions[15].

However, to date there are no specific compositions or treatment methods which address and target the IL-36 aspect of inflammatory disorders. Accordingly, the present invention is directed to new and improved methods and compositions for the treatment of inflammatory conditions.

SUMMARY

According to a first aspect of the invention, there is provided the use of an agent capable of inhibiting IL-36 proteolytic processing, particularly IL-36 activation that occurs via proteolytic processing, for the treatment and/or reduction of inflammation, particularly inflammatory skin disorders, in a subject.

According to a second aspect of the invention, there is provided a composition comprising an agent capable of inhibiting IL-36 proteolytic processing, particularly IL-36 activation that occurs via proteolytic processing, and a suitable pharmaceutical excipient.

According to a third aspect of the invention, there is provided a topical inflammatory skin disorder treatment composition comprising an agent capable of inhibiting IL-36 proteolytic processing, particularly IL-36 activation that occurs via proteolytic processing, and a suitable pharmaceutical excipient.

According to a forth aspect of the invention, there is provided an agent capable of inhibiting IL-36 proteolytic processing, particularly IL-36 activation that occurs via proteolytic processing, for use in the manufacture of a medicament for the treatment and/or reduction of inflammation particularly inflammatory skin disorders, in a subject.

According to a fifth aspect of the invention, there is provided a method for the treatment and/or reduction of inflammation in a subject, preferably inflammation of barrier organs, including inflammation of the skin, gut and/or lung, particularly inflammatory skin disorders, comprising administering an agent capable of inhibiting IL-36 proteolytic processing, particularly IL-36 activation that occurs via proteolytic processing, to a subject to result in the treatment and/or reduction of inflammation in said subject.

DETAILED DESCRIPTION OF A PREFERRED EMBODIMENT

Unless otherwise defined, all terms of art, notations and other scientific terminology used herein are intended to have the meanings commonly understood by those skilled in the art to. In some cases, terms with commonly understood meanings are defined herein for clarity and/or for ready reference; thus, the inclusion of such definitions herein should not be construed to represent a substantial difference over what is generally understood in the art.

In particular, the terms "physiologically acceptable excipient" or "pharmaceutically acceptable excipient" herein refers to a substance devoid of any pharmacological effect of its own and which does not produce adverse reactions when administered to a mammal, preferably a human. Physiologically acceptable excipients are well known in the art and are disclosed, for instance in the Handbook of Pharmaceutical Excipients, sixth edition (2009), herein incorporated by reference.

The term "approximately" herein refers to the range of the experimental error, which may occur in a measurement.

The terms "comprising", "having", "including" and "containing" are to be construed as open-ended terms (i.e. meaning "including, but not limited to") and are to be considered as including the terms as "consist essentially of", "consisting essentially of", "consist of" or "consisting of".

The terms "consist essentially of", "consisting essentially of" are to be construed as a semi-closed terms, meaning that no other ingredients which materially affects the basic and novel characteristics of the invention are included (optional excipients may thus be included).

The terms "consists of", "consisting of" are to be construed as a closed term. As used herein, the terms "therapeutically effective amount" and "effective amount" refer to an amount sufficient to elicit the desired biological response. In the present invention the desired biological response is to inhibit, reduce or ameliorate the severity, duration, progression, or onset of inflammation or associated disease, disorder or condition, prevent the advancement, recurrence, or progression of inflammation or associated disease, disorder or condition or a symptom associated with a disease, disorder or condition. The precise amount of compound administered to a subject will depend on the mode of administration, the type and severity of the disease, disorder or condition and on the characteristics of the subject, such as general health, age, sex, body weight and tolerance to drugs. The skilled artisan will be able to determine appropriate dosages depending on these and other factors. Suitable dosages are known for approved agents and can be adjusted by the skilled artisan according to the condition of the subject, the type of condition(s) being treated and the amount of a compound described herein being used. In cases where no amount is expressly noted, an effective amount should be assumed.

As used herein, the terms "treat", "treatment" and "treating" refer to therapeutic treatments includes the reduction or amelioration of the progression, severity and/or duration of inflammation to associated disease, disorder or condition, or the amelioration of one or more symptoms (specifically, one or more discernible symptoms) of inflammation or associated disease, disorder or condition, resulting from the administration of one or more therapies (e.g., one or more therapeutic agents such as a compound or composition of the invention). In specific embodiments, the therapeutic treatment includes the amelioration of at least one measurable physical parameter of inflammation or associated disease, disorder or condition. In other embodiments the therapeutic treatment includes the inhibition of the progression of inflammation or associated condition, either physically by, e.g., stabilization of a discernible symptom, physiologically by, e.g., stabilization of a physical parameter, or both. In other embodiments the therapeutic treatment includes the reduction or stabilization of inflammation or associated disease, disorder or condition.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In one embodiment, the subject is a human.

In this specification, it will be understood that reference to Interleukin-36, IL-36 cytokines or IL-36 includes one or more of the IL-36 isoforms, IL-36α (IL-36A; IL-36 alpha; Interleukin-36 alpha), IL-36β (IL-36B; IL-36 beta; Interleukin-36 beta) and/or IL-36γ (IL-36G; IL-36 gamma; Interleukin-36 gamma) and reference to IL-36 proteolytic processing includes one or more of IL-36α, IL-36β and/or IL-36γ proteolytic processing.

In this specification, it will be understood that reference to protease cleavage site or relevant protease cleavage site refers to an IL-36 protease cleavage site which is required for activation of IL-36.

According to a first aspect of the invention, there is provided the use of an agent capable of inhibiting IL-36 activation that occurs via proteolytic processing for the treatment and/or reduction of inflammation in a subject. Although, the treatment and/or reduction of inflammation of the skin, gut and/or lung is contemplated, the treatment and/or reduction of inflammatory skin disorders are preferred.

The agent of the invention prevents the production of a biologically active IL-36 by preventing the activation that occurs by proteolytic processing of IL-36, including one or more of IL-36α, IL-36β and/or IL-36γ, to prevent and/or reduce the pro-inflammatory effects of IL-36 including IL-36α, IL-36β and/or IL-36γ.

Previously, it was not known which proteases were responsible for activation of IL-36 proteins. We have surprisingly discovered that the neutrophil-derived proteases, including serine proteases and cysteine proteases such as cathepsin G and elastase are potent IL-36, IL-36α, IL-36β (IL-36B) and/or IL-36γ (IL-36G), processing proteases. Other relevant proteases which may be targeted in the invention include cathepsin K, proteinase-3 and/or DPPI (dipeptidyl peptidase I) known as Cathepsin C. As psoriasis plaques are frequently associated with neutrophil infiltrates, we have surprisingly found that inhibitors of neutrophil granule proteases have significant potential as inhibitors of IL-36 activation in inflammatory skin conditions, including but not limited to psoriasis. These surprising findings suggest that targeted inhibition of these proteases have therapeutic benefits in inflammatory skin conditions such as psoriasis and other similar skin conditions.

We have also identified the protease cleavage sites within the IL-36 isoforms which result in the activation of IL-36. Our findings suggest that the protease cleavage sites of the IL-36 isoforms may also be targeted and/or mimicked to directly inhibit IL-36 activation.

We postulate that the prevention of a biologically active IL-36 isoform can be used in the treatment and/or prevention of IL-36 associated diseases or disorders.

It will be understood that the agent of the invention may inhibit IL-36 proteolytic processing either directly or indirectly. Direct inhibition aims to target and/or mimic the newly identified IL-36 protease cleavage sites and/or amino acid residues downstream and/or upstream of the cleavage site. Indirect inhibition aims to inhibit the activity of the IL-36 activating proteases and activators thereof. According to a preferred embodiment of the invention, the agent inhibits IL-36 activation by binding to the IL-36 protease cleavage sites required for activation of IL-36 (direct inhibition) and/or amino acid residues downstream and/or upstream of the cleavage site; and/or the agent prevents and/or inhibits the activity of IL-36 activating proteases or activators thereof (indirect inhibition).

The agent may be selected from one or more of the following group a small molecule or biologics, including peptide, polypeptide, protein, siRNA, sgRNA, and antibody.

According to a preferred embodiment, the agent is a small molecule protease inhibitor. According to a preferred embodiment the small molecule protease inhibitor is a serine protease or cysteine protease inhibitor. For example, the protease inhibitor may be selected from one or more of a cathepsin K inhibitor, cathepsin C(DPPI) inhibitor, elastase inhibitor, cathepsin-G inhibitor and proteinase-3 inhibitor. Suitable protease inhibitors, include, but are not limited to boswellic Acids, cathepsin G inhibitor I, Elastase inhibitor IV, Sodium Fluoride, 4-(2-Aminoethyl) benzenesulfonyl fluoride hydrochloride (AEBSF.HCl), phenylmethanesulfonylfluoride (PMSF), Odanacatib™ (MK-0822) (N-(1-cyanocyclopropyl)-4-fluoro-N2-{(1S)-2,2,2-trifluoro-1-[4'-(methylsulfonyl)biphenyl-4-yl]ethyl}-L-leucinamide), Balicatib™ (N-[1-(cyanomethylcarbamoyl)cyclohexyl]-4-(4-propylpiperazin-1-yl)benzamide), MV061194, Aprotinin™ (small protein bovine pancreatic trypsin inhibitor (BPTI)), Leupeptin™ (N-Acetyl-leucyl-N-{(5-[(diaminomethylidene)amino]-1-oxopentan-2-yl}-leucinamide), peptide inhibitor dipeptide-derived diazoketones such as Gly-Phe-CHN2 and vinyl sulfones such as Ala-Hph-VS-Ph.

Optional protease inhibitors includes aspartate protease inhibitors, glutamic acid protease inhibitors, metalloprotease inhibitors, asparagine peptide lyase inhibitors.

According to another preferred embodiment, the agent is a peptide, derivative, peptidomimetic or combination thereof. Ideally, the peptide comprises 3, 4, 5, 6, 7, 8, 9 or 10 amino acids. In one preferred embodiment, the peptide is a tripeptide or tetrapeptide. The peptide is a synthetic or non-natural peptide. The peptide may inhibit IL-36 activation via proteolytic processing in several ways including:
i) by binding to the protease cleavage site(s) within IL-36 required for activation of IL-36;
ii) competing with IL-36 activating protease(s) for binding to the protease cleavage site(s) within IL-36 required for activation of IL-36; and/or
iii) inhibiting IL-36 activation by preventing and/or inhibiting the activity of IL-36 activating proteases or activators thereof;

Suitable peptides include Lys-Ala-Leu (KAL); Ala-Leu-Ala (ALA); Met-Ala-Leu-Ala (MALA); Asp-Pro Gln-Arg (NPQR); Pro-Gln-Arg (PQR); Gln-Arg-Glu-Ala (QREA); Arg-Ala-Val (RAV); Gly-Arg-Ala-Val (GRAV); Ala-Val-Tyr-Gln (AVYQ); and derivatives or peptidomimetics thereof. Derivatives include chemically modified derivatives explained below including CMK modified peptides.

Other suitable peptides include Phe-Leu-Phe (FLF); Glu-Pro-Phe (EPF); Ala-Phe-Leu-Phe (ALPF); Lys-Ala-Leu (KAL); Arg-Ala-Val (RAV), Asp-Thr-Glu-Phe (DTEF), Ala-Pro-Leu (APL), Pro-Gln-Arg (PQR), Arg-Pro-Leu (RPL); and derivatives or peptidomimetics thereof. Derivatives include chemically modified derivatives explained below including chloromethyl ketones (CMK) modified peptides.

Direct Inhibition

According to one embodiment, the agent may directly inhibit IL-36 proteolytic processing by binding to the protease cleavage sites within IL-36 required for activation of IL-36 and/or competing with the IL-36 activating proteases, such as cathepsin G, elastase or cathepsin K, cathepsin C(DPPI) or proteinase-3, for binding to their respective cleavage sites within IL-36 required for activation of IL-36. In this manner the agent of the invention is designed to target and/or mimic the protease cleavage sites within IL-36 required for activation of IL-36 (IL-36α, IL-36β and/or IL-36γ).

Additionally, in addition to targeting the protease cleavage sites within IL-36 required for activation of IL-36, the agent may also target and/or mimic one or more amino acid residues downstream and/or upstream of the protease cleavage site.

For example, the agent may target IL-36β cleavage site, R (amino acid residue 5), and optionally one or more of the surrounding downstream residues N, P and/or Q (NPQR$_5$).

Additionally, the agent may target the IL-36γ cleavage site V (amino acid residue 15) and optionally one or more of the surrounding downstream residues G, R and or V (GRA$\underline{V}_{15}$).

Additionally, the agent may target the IL-36α cleavage site K (amino acid residue 3) and/or cleavage site A (amino acid 4) and optionally one or more of the surrounding downstream residues MEK$_3$ A$_4$(SEQ ID No. 28). We have found that Cathepsin G cleaves IL-36α at residue K(3) while elastase cleaves at residue A(4).

Ideally, the agent targets both the cleavage site and one or more of the surrounding upstream and downstream residues, including for example, IL-36β cleavage site NPQR$_5$ EAPP (SEQ ID No. 1) or the IL-36γ cleavage sites GRAV$_{15}$ YQSM (SEQ ID No. 2) or IL-36α cleavage sites MEK$_3$ A$_4$ LKID (SEQ ID No. 28). In this manner one or more additional amino acid residue selected from N, P and/or Q and one or more additional amino acid residues selected from E, A, P and/or P may be targeted for IL-36β. Additionally, one or more additional amino acid residue selected from G, R and/or V and one or more additional amino acid residues selected from Y, Q, S and/or M may be targeted for IL-36γ. Additionally, one or more additional amino acid residue selected from M, E, K, and/or A and one or more additional amino acid residues selected from L, K, I, and/or D may be targeted for IL-36α.

Full details of IL-36 including GenBank IDs and the cleavage sites are listed below. The cleavage sites within each amino acid sequence are underlined below.

IL-36β (IL-36B) DNA and Amino Acid Sequence:
GenBank: BC101833.1 (DNA Sequence) as Shown in FIG. 36 (SEQ ID No. 3)
gb|BC101833.1|:63-536 Homo sapiens interleukin 1 family, member 8 (eta), mRNA (cDNA clone MGC:126882 IMAGE:8069339), complete cds
GenBank: AAI01834.1 (Amino Acid Sequence) SEQ ID No. 4
gi|75517955|gb|AAI01834.1| Interleukin 1 family, member 8 (eta) [Homo sapiens]

$_1$MNPQR$_5$EAAPKSYAIRDSRQMVWVLSGNSLIAAPLSRSIKPVTLHLIAC

RD<u>TEFS</u>DKEKGNMVYLGIKGKDLCLFCAEIQGKPTLQLKEKNIMDLYVEK

KAQKPFLFFHNKEGSTSVFQSVSYPGWFIATSTTSGQPIFLTKERGITNN

TNFYLDSVE$_{157}$

NPQR is a protease cleavage site within IL-36β which is required for the activation of IL-36β. DTEF (also underlined) is another protease cleavage site that is cleaved by cathepsin G, however, we understand that DTEF is not required for activation of IL-36B.

IL-36γ (IL-36G) DNA and Amino Acid Sequence:
GenBank: BC098337.1 (DNA Sequence) as Shown in FIG. 37 (SEQ ID No. 5)
gb|BC098337.1|:25-534 Homo sapiens interleukin 1 family, member 9, mRNA (cDNA clone MGC:119102 IMAGE:40003612), complete cds
The coding region (CDS) for IL-36γ comprises nucleotides 25 to 534 from the entire IL-36γ sequence which comprises nucleotide 1 to 791.
GenBank: AAH98337.1 (Amino Acid Sequence) (SEQ ID No. 6)
gi|68226701|gb|AAH98337.1| Interleukin 1 family, member 9 [Homo sapiens]

$_1$MRGTPGDADGGGRAV$_{15}$YQSMCKPITGTINDLNQQVWTLQGQNLVAVP

RSDSVTPVTVAVITCKYPEALEQGRGDPIYLGIQNPEMCLYCEKVGEQPT

LQLKEQKIMDLYGQPEPVKPFLFYRAKTGRTSTLESVAFPDWFIASSKRD

QPIILTSELGKSYNTAFELNIND$_{169}$

GRAV is a protease cleavage site within IL-36γ which is required for the activation of IL-36γ.

IL-36α (IL-36A) DNA and Amino Acid Sequence:
GenBank: NM 014440.1 (DNA Sequence) as Shown in FIG. 38 (SEQ ID No. 26)
gi|7657091|ref|NM_014440.1|Homo sapiens interleukin 36, alpha (IL36A), mRNA
GenBank: NP_055255.1 (Amino Acid Sequence) SEQ ID No. 27 gi|7657092|ref|NP_055255.1| interleukin-36 alpha [Homo sapiens] SV=1

$_1$MEK$_3$A$_4$LKIDTPQQGSIQDINHRVWVLQDQTLIAVPRKDRMSPVTIALI
SCRHVETLEKDRG
NPIYLGLNGLNLCLMCAKVGDQPTLQLKEKDIMDLYNQPEPVKSFLFYHS
QSGRNSTFES VAFPGWFIAVSSEGGCPLILTQELGKANTTDFGLTML
F$_{158}$

MEK$_3$ is a protease cleavage site of cathepsin-G within IL-36α, which is required for the activation of IL-36α. MEKA$_4$ is a protease cleavage site of elastase within IL-36α, which is required for the activation of IL-36α.

These findings have led to the generation of agents, preferably synthetic peptides, peptides derivatives and peptidomimetics thereof, which aim to target and/or mimic the IL-36 protease cleavage sites which directly inhibit IL-36 activation via proteolytic processing.

According to one embodiment, the peptides are tri-peptide and tetra-peptides or peptides derivatives and peptidomimetics thereof which aim to target and/or mimic the IL-36 protease cleavage sites which directly inhibit IL-36 activation via proteolytic processing.

These peptides are designed to target and/or mimic the new protease cleavage sites identified. The peptides can be conventionally designed to target and/or mimic these new protease cleavage site using standard chemistry techniques (e.g.

Thornberry et al., A novel heterodimeric cysteine protease is required for interleukin-1 beta processing in monocytes. Nature. 1992 Apr. 30; 356(6372):768-74; Nicholson et al., Identification and inhibition of the ICE/CED-3 protease necessary for mammalian apoptosis. Nature. 1995 Jul. 6; 376(6535):37-43; Powers J C et al, Irreversible inhibitors of serine, cysteine, and threonine proteases. Chem. Rev. 102, 4639-750. (2002); Merrifield, R. B. Solid Phase Peptide Synthesis. I. The Synthesis of a Tetrapeptide, J. Am. Chem. Soc., 85, 2149-2154 (1963); Nilsson, B. L., Soellner, M. B., Raines, R. T. Chemical Synthesis of Proteins. Annu. Rev. Biophys. Biomol. Struct 2005; 34: 91-118 (2005)).

The agents may be a peptide which mimics the protease cleavage sites within IL-36β, IL-36γ and/or IL-36α required for activation of IL-36β, IL-36γ and/or IL-36α and binds said protease cleavage sites to inhibit its activity; or derivatives or peptidomimetics thereof.

Suitable peptide derivatives include chemically modified peptides. Chemical modifications to the peptides aim to increase stability and efficiency. Furthermore, the coupling or combinations of peptides using chemical linkers may also be contemplated. Chemical modifications include addition of chloromethyl ketones (CMK), fluoromethyl ketone (FMK), and aldehyde/formyl group (R—CHO) to the C-terminus (carboxyl group) to increase potency, through the formation of irreversible or reversible bonds with the target proteases active site amino acid (e.g. serine, cysteine), such that lower concentrations of peptides are required to achieve inhibition.

Additional chemical modifications may include addition of protection groups to the N-terminus (amino group) to stabilizes the tri-/tetra-peptide and protect it from degradation; including N-benzyloxycarbonyl (Benzyl carbamate), butyl carbamate, Acetamide, phthalimide, benzylamine, triphenylmethylamine, benzylideneamine, p-toluenesulfonamide.

Preferred chemical modifications or derivates include:
Cyclization: Cyclization is typically carried out using side chains or N-/C-terminal regions of the peptide sequence through the formation of disulfide bonds. For example, lanthionine, dicarba, hydrazine or lactam bridges. Advantages to cycling peptides are to reduce hydrophilicity, decrease conformational flexibility, enhance membrane permeability and increase stability to proteolysis.
PEGylation: is the process of both covalent and non-covalent attachment of polyethylene glycol (PEG) polymer chains to molecules and macrostructures, such as a peptide, a therapeutic protein or antibody. Advantages to PEGylation include slowed systemic clearance and increased absorption.
Lipidization: is the addition of fatty acids to a peptide or protein to increase the lipophilicity of the peptides by forming a stable amide bond between a carboxyl group of a lipid molecule and an amino group of a peptide or protein. Advantages include improved transport across biological membrane, higher stability and longer plasma half-life.
N-acetylation: The addition of a acetyl functional group to the N-terminus of a peptide. Advantages include increased metabolic stability, resistance to proteolytic degradation and increased bioavailability of the peptide.
D-AA: is the substitution of natural L-amino acids with D-amino acids. Advantages to D-amino acid substitution can result in increased resistance to proteolytic degradation and improved stability.
Cross-linking: These are a-helical peptides containing a synthetic hydrocarbon backbone linking various residues. The backbone, referred to as the staple, locks the conformation of the peptide increasing it helicity, stability and increased cell penetration. [REF:34]

Peptidomimetics are also contemplated, involving modifying the peptides themselves or by designing an alternative compound/composition which mimics the peptide. Conventional techniques may be used to generate such peptidomimetics.

Table 1 provides a list of exemplary tri-peptides and tetra-peptides designed to mimic the protease cleavage sites of the invention. CMK altered derivatives of these tripeptide and tetra-peptides may also be used.

TABLE 1

Exemplary Agents and derivatives thereof which mimic and/or target the IL-36 protease cleavage sites

| AGENT WITH CMK derivative thereof | AGENT TARGETS IL-36 ISOFORM |
|---|---|
| Lys-Ala-Leu (KAL); KAL-CMK | IL-36α |
| Ala-Leu-Ala (ALA); ALA-CMK | IL-36α |
| Met-Ala-Leu-Ala (MALA) (SEQ ID No. 29); MALA-CMK; | IL-36α |
| Asp-Pro-Gln-Arg (NPQR) (SEQ ID No. 30); NPQR-CMK; | IL-36β |

TABLE 1-continued

Exemplary Agents and derivatives thereof which mimic and/or target the IL-36 protease cleavage sites

| AGENT WITH CMK derivative thereof | AGENT TARGETS II-36 ISOFORM |
|---|---|
| Pro-Gln-Arg (PQR); PQR-CMK; | IL-36β |
| Gln-Arg-Glu-Ala (QREA) (SEQ ID No. 31); QREA-CMK | IL-36β |
| Arg-Ala-Val (RAV) RAV-CMK | IL-36γ |
| Gly-Arg-Ala-Val (GRAV) (SEQ ID No. 32); GRAV-CMK | IL-36γ |
| Ala-Val-Tyr-Gln (AVYQ) (SEQ ID No. 33); AVYQ-CMK; | IL-36γ |

The skilled man would understand that these peptides have been designed to bind and/or mimic the respective IL-36 protease active site and effectively compete with the substrate, IL-36, for proteolysis. This is governed by electrostatic interactions between the protease active site and the peptide which mimics the proteolytic cleavage site of a naturally occurring substrate. Therefore, an effective amount of these peptide this will result in reversible inhibition, as the active site of the protease will be occupied by the tri/tetrapeptide, thus protecting the substrate, IL-36, from proteolysis.

In the case of CMK modified peptides, the CMK chemical group located at the C-terminus of the peptide will similarly occupy the active site but will form a covalent bond resulting in irreversible inhibition of the protease. (REF:35)

Indirect Inhibition

According to another embodiment, the agent may indirectly inhibit IL-36 proteolytic processing by preventing and/or inhibiting the activity of proteases which proteolytically process IL-36.

According to a one embodiment, the agent of the invention may be a conventional cysteine protease inhibitor or a serine protease inhibitor. Other proteases may be used as described above.

This is based on our finding that cysteine proteases including cathepsin-C/DPPI and cathepsin K and the serine proteases including cathepsin G, elastase and proteinase-3 have a role in activating IL-36 via proteolytic processing.

Serine proteases are characterised by a distinctive structure, consisting of two beta-barrel domains that converge at the catalytic active site. The catalytic triad of a serine protease consists of a Serine-Histidine-Aspartic acid (Ser-His-Asp), whereby the serine is the nucleophillic residue. Suitable serine protease inhibitors which may be used in the invention bind into the active site of the protease, typically exploiting the nucleophilic serine, either forming stable acyl intermediates (sulphonyl flourides/chlorides, phosphonates), or stable tetrahedral intermediates (aldehydes, halomethyl ketones, boronic acids.)

Accordingly, it will be understood that additional serine protease inhibitors may also be utilised in the present invention. Suitable serine protease inhibitors may be selected from the following groups:

Trypsin-like serine proteases: Trypsin-like proteases cleave peptide bonds following a positively charged amino acid (lysine (K) or arginine (R). This specificity is driven by the residue, which is located at the base of the enzyme's S1 pocket, typically a negatively charged aspartic acid (D) or glutamic acid (E).

Chymotrypsin-like serine proteases: The S1 pocket of chymotrypsin-like enzymes is more hydrophobic than in trypsin-like proteases. A consequence of this is that there is a specificity for medium to large sized hydrophobic residues, such as tyrosine (Y), phenylalanine (F) and tryptophan (W).

Elastase-like serine proteases: Elastase-like proteases have a smaller S1 cleft than either trypsin- or chymotrypsin-like proteases. Consequently, residues such as alanine (A), glycine (G) and valine (V) tend to be preferred.

Subtilisin-like serine proteases: Subtilisin is a serine protease in prokaryotes. Subtilisin share the same catalytic mechanism as chymotrypsin-like utilising a catalytic triad, to create a nucleophilic serine.

According to a preferred embodiment, one or more serine proteases selected from serine protease families S1 to S81 (MEROPS classification system) may be used.

According to a preferred embodiment, the agent of the invention may be a naturally occurring serine protease inhibitors from the serpin family and the chelonianin family.

Members of the serpin family include α1-Antichymotrypsin, α1-Antitrypsin, SerpinB1, PI6, PI9. It is known that serpins inhibit proteases by a suicide substrate inhibition mechanism. The protease initially recognizes the serpin as a potential substrate using residues of the reactive center loop (RCL) and cleaves it between P1 and P1'. This cleavage allows insertion of the cleaved RCL into the R-sheet A of the serpin, dragging the protease with it and moving it over 71 Å to the distal end of the serpin resulting in a 1:1 stoichiometric covalent inhibitory complex. The protease is distorted into a conformation, where the acyl enzyme intermediate is hydrolysed extremely slowly.

Members of the chelonianin family include SLPI and Elafin.

Cysteine protease are characterised by a common catalytic mechanism. The catalytic triad of a cysteine protease consists of a cysteine-histidine-aspartic acid (Cys-His-Asp), whereby the cysteine is the nucleophillic residue. We postulate that other cysteine proteases may work in accordance with the invention. These include naturally occurring cysteine protease inhibitors from cysteine families C1-C110 (MEROPS classification).

Based on our surprising findings that the neutrophil-derived proteases elastase, cathepsin G, cathepsin K orcathepsin-C/DPPI process and activate IL-36. Thus, according to a preferred embodiment of the invention the agent may be designed to prevent the binding of elastase, cathepsin G, proteinase-3, cathepsin K or cathepsin-C/DPPI, or other related proteases to IL-36 and to prevent conversion of IL-36 to its active form by elastase, cathepsin G, proteinase-3, cathepsin K or cathepsin-C/DPPI, or other neutrophil-derived proteases.

We have also found that cathepsin K, a protease predominantly expressed in osteoclasts, can cleave and activate IL-36β (beta) at the same residue as Cathepsin G (NPQR$_5$ EAAP).

Furthermore, DPPI is an enzyme expressed in neutrophil granules that processes the neutrophil proteases (Elastase, Cathepsin G and proteinase 3) into fully active proteases. DPPI is responsible for the activation of a number of proteases, which include CatG, elastase, proteinase-3 granzyme A, granzyme B, granzyme C and chymase. In this manner, DPPI is an activator of IL-36 proteases. Targeted inhibition of DPPI would be an indirect way in which to suppress IL-36 activation. Dipeptide-derived diazoketones, such as Gly-Phe-CHN2 (Gly-Phe-diazomethane) can be used to inhibit DPPI.

In this manner, the agent may be a conventional elastase, cathepsin G, proteinase-3, cathepsin K or cathepsin-C/DPPI inhibitor as highlighted in Table 2 below.

It will be understood that the agent of the invention may be a small molecule or a biologic including, peptides, polypeptide, protein, siRNA, antibody, and/or targeted genome editing/sgRNA e.g CRISPR-Cas system. sgRNA relates to the emerging CRISP/Cas9 genome editing technology.

acids, that binds an IL-36 activating protease and/or competes with IL-36 activating proteases for access to the IL-36 cleavage sites.

Ideally, the peptide is a tripeptide or tetrapeptide, although longer peptide chains may be used. Optionally the peptide may be up to 8-10 amino acids in length.

According to one embodiment of the invention, the peptide, which may be a tripeptide or tetrapeptide, binds to the IL-36 neutrophil-derived protease and/or competes with neutrophil-derived proteases for access to the IL-36 neutrophil-derived protease cleavage sites.

Additionally, the peptide of the invention may be linked to form multi-peptide combinations, comprising for example from 2 to 20 tripeptide or tetrapeptide units. Optionally, the multi-peptide combination comprises 6/8, 9/12 or 12/16

TABLE 2

Exemplary Agents which indirectly inhibit activation of IL-36 proteolytic processing by preventing and/or inhibiting the activity of IL-36 activating proteases or activators thereof

| Agent Type | Protease Target |
| --- | --- |
| SERINE PROTEASE INHIBITORS (SMALL MOLECULE) | |
| Boswellic Acids | Cathepsin G inhibitor (serine protease) |
| cathepsin G inhibitor I | Cathepsin G inhibitor (serine protease) |
| Elastase inhibitor IV | Elastase inhibitor (serine protease) |
| Sodium Fluoride | Ser/Thr and acidic phosphatases |
| 4-(2-Aminoethyl) benzenesulfonyl fluoride hydrochloride (AEBSF•HCl) | Non-specific serine protease inhibitor |
| phenylmethanesulfonylfluoride (PMSF) | Non-specific serine protease inhibitor |
| dipeptide-derived diazoketones, such as Gly-Phe-CHN2 (Gly-Phe-diazomethane) | DPPI/Cathepsin C inhibitor (cysteine protease) |
| Vinyl sulfones such as Ala-Hph-VS-Ph | DPPI/Cathepsin C inhibitor (cysteine protease) |
| Odanacatib ™ (MK-0822) (N-(1-cyanocyclopropyl)-4-fluoro-N2-{(1S)-2,2,2-trifluoro-1-[4'-(methylsulfonyl)biphenyl-4-yl]ethyl}-L-leucinamide) | Cathepsin K inhibitor (cysteine protease) |
| Balicatib ™ (N-[1-(cyanomethylcarbamoyl)cyclohexyl]-4-(4-propylpiperazin-1-yl)benzamide) | Cathepsin K (cysteine protease) |
| MV061194 | Cathepsin K (cysteine protease) |
| SERINE PROTEASE INHIBITORS (BIOLOGIC) | |
| Aprotinin ™ (small protein bovine pancreatic trypsin inhibitor (BPTI)) | Non-specific serine protease inhibitor |
| Leupeptin ™ (N-Acetyl-leucyl-N-{(5-[(diaminomethylidene)amino]-1-oxopentan-2-yl}-leucinamide) | Non-specific serine protease inhibitor |

According to a preferred embodiment of the invention, the agent may be a small molecule or biologic inhibitor of cathepsin G and elastase is selected from known serine protease inhibitors and cathespin K inhibitors including but not limited to cathepsin G inhibitor I, Elastase inhibitor IV, Sodium Fluoride, 4-(2-Aminoethyl) benzenesulfonyl fluoride hydrochloride (AEBSF.HCl), Aprotinin, Leupeptin, phenylmethanesulfonylfluoride (PMSF), Boswellic Acids, cathepsin K inhibitor 1, and/or Odanacatib (cathepsin K inhibitor).

According to another embodiment, the agent of the invention may be a peptide from 3 to 10 amino acids in length, comprising or consisting of 3, 4, 5, 6, 7, 8, 9 or 10 amino multiples of tripeptides or tetra peptides. As described below the peptides may be chemically linked to form multi-peptide combinations.

In this manner, the peptides target the proteases directly. The peptide sequences (e.g. tri/tetra peptides etc as outlined below) are designed to mimic and/or target the cleavage sites and motifs within the IL-36 proteins to act as targets for any proteases, thereby, protecting IL-36 from proteolysis.

These peptides may be designed and manufactured using standard chemistry techniques (e.g. Thornberry et al., A novel heterodimeric cysteine protease is required for interleukin-1 beta processing in monocytes. Nature. 1992 Apr. 30; 356(6372):768-74; Nicholson et al., Identification and inhibition of the ICE/CED-3 protease necessary for mammalian apoptosis. Nature. 1995 Jul. 6; 376(6535):37-43; Powers J C et al, Irreversible inhibitors of serine, cysteine, and threonine proteases. Chem. Rev. 102, 4639-750. (2002); Merrifield, R. B. Solid Phase Peptide Synthesis. I. The Synthesis of a Tetrapeptide, J. Am. Chem. Soc., 85, 2149-2154 (1963); Nilsson, B. L., Soellner, M. B., Raines, R. T. Chemical Synthesis of Proteins. Annu. Rev. Biophys. Biomol. Struct 2005; 34: 91-118 (2005))

TABLE 3

Exemplary synthetic peptides which indirectly inhibit activation of IL-36 proteolytic processing by preventing and/or inhibiting the activity of IL-36 activating proteases or activators thereof

SYNTHETIC PEPTIDE

| AGENT | AGENT INHIBITS THE ACTIVITY OF THE FOLLOWING IL-36 ACTIVATING PROTEASES | AGENT TARGETS IL-36 ISOFORM |
|---|---|---|
| Phe-Leu-Phe (FLF) | Cathepsin G-inhibitory peptides | IL-36β |
| Glu-Pro-Phe (EPF) | Cathepsin G-inhibitory peptides | IL-36β |
| Ala-Phe-Leu-Phe (AFLF) (SEQ ID No. 7) | Cathepsin G-inhibitory peptides | IL-36β |
| Lys-Ala-Leu (KAL) | | |
| Phe-Leu-Phe (FLF-CMK) | Cathepsin G-inhibitory peptides | IL-36β |
| Glu-Pro-Phe-CMK (EPF-CMK) | Cathepsin G-inhibitory peptides | IL-36β |
| Ala-Phe-Leu-Phe-CMK (AFLF-CMK) | Cathepsin G-inhibitory peptides | IL-36β |
| Lys-Ala-Leu-CMK (KAL-CMK) | Cathepsin G/Elastase-inhibitory peptides | IL-36α |
| Arg-Ala-Val (RAV) | Elastase-inhibitory peptides | IL-36γ |
| Asp-Thr-Glu-Phe (DTEF) (SEQ ID No. 8) | Elastase/Proteinase-3-inhibitory peptides | IL-36γ |
| Ala-Pro-Leu (APL) | Elastase/Proteinase-3-inhibitory peptides | IL-36γ |
| Pro-Gln-Arg (PQR) | Elastase/Proteinase-3-inhibitory peptides | IL-36γ |
| Arg-Pro-Leu (RPL) | Elastase/Proteinase-3-inhibitory peptides | IL-36γ |

The rationale for designing peptides Arg-Ala-Val (RAV), Asp-Thr-Glu-Phe (DTEF), Ala-Pro-Leu (APL), Pro-Gln-Arg (PQR), Arg-Pro-Leu (RPL) was to inhibit elastase activity, centered around tri-peptide motifs that elastase preferentially cleaves (see FIG. 32). CMK modified Arg-Ala-Val (RAV), Asp-Thr-Glu-Phe (DTEF), Ala-Pro-Leu (APL), Pro-Gln-Arg (PQR), Arg-Pro-Leu (RPL) are also contemplated.

As described above, chemical modifications to the peptides aim to increase stability and efficiency. Furthermore, the coupling or combinations of peptides using chemical linkers may also be contemplated. Chemical modifications include addition of chloromethyl ketones (CMK), fluoromethyl ketone (FMK), and aldehyde/formyl group (R—CHO) to the C-terminus (carboxyl group) to increase potency, through the formation of irreversible or reversible bonds with the target proteases active site amino acid (e.g. serine, cysteine), such that lower concentrations of peptides are required to achieve inhibition.

Additional chemical modifications may include addition of protection groups to the N-terminus (amino group) to stabilizes the tri-/tetra-peptide and protect it from degradation; including N-benzyloxycarbonyl (Benzyl carbamate), butyl carbamate, Acetamide, phthalimide, benzylamine, triphenylmethylamine, benzylideneamine, p-toluenesulfonamide.

Combinations of peptides may be used that simultaneously target both elastase, cathepsin G or cathepsin K. In one embodiment of the invention, candidate peptides that target both elastase and cathepsin G and/or cathepsin K may be "linked" via a chemical linker. According to another aspect of this, the agent may chemically cross-link two or more peptides to form multi-peptide combinations According to a preferred embodiment the peptide may be selected from the peptides listed within the following table

TABLE 4

| Tri/Tetra Peptides |
|---|
| Glu-Pro-Phe (EPF) |
| Ala-Phe-Leu-Phe (AFLF) (SEQ ID No. 7) |
| Lys-Ala-Leu (KAL) |
| Glu-Pro-Phe-CMK (EPF-CMK) |
| Ala-Phe-Leu-Phe-CMK (ALFL-CMK) |
| Lys-Ala-Leu-CMK (KAL_CMK) |
| Arg-Ala-Val (RAV) |
| Asp-Thr-Glu-Phe (DTEF) (SEQ ID No. 8) |
| Ala-Pro-Leu (APL) |
| Pro-Gln-Arg (PQR) |
| Arg-Pro-Leu (RPL) | or chemically modified derivatives thereof or combinations thereof.

According to yet another aspect of the invention, the antibody may be a polyclonal or monoclonal antibody raised against IL-36 activating proteases, including the proteases elastase or cathepsin G, K or C. In this manner, the antibody binds to the IL-36 activating protease to prevent the protease binding to the protease cleavage sites within IL-36.

According to another aspect of the invention, the antibody may be a polyclonal or monoclonal antibody raised against the protease cleavage site amino acid sequence within IL-36, preferably IL-36β and IL-36γ. In this manner, the antibody binds the amino acid sequence encompassing the protease cleavage site within IL-36 to block access of the IL-36 activating protease to the IL-36 cleavage sites.

It will be understood that the present invention may be directed to the treatment of inflammation of barrier organs in a subject, including inflammation of the skin, g Ideally, the present invention may be used in the treatment of inflammatory skin disorders, such as psoriasis, including Psoriasis vulgaris, dermatitis and/or acne, sebaceous cysts, vasculitis, eczema, dermatitis, granuloma annulare, lichen planus, bullous pemphigoid, molluscum contagiosum, dermatomyositis and ichthyosis vulgaris. For example, plaque, guttate, palmoplantar, generalized pustular and/or arthritic psoriasis may be treated in accordance with the invention. Psoriasis will be understood to cover all forms of psoriasis including psoriasis vulgaris, plaque psoriasis, guttate psoriasis, flexural (inverse) psoriasis, erythroderma psoriasis, generalized pustular psoriasis, arthritic psoriasis, palmoplanter pustulosis and psoriatic nail disease.

According to a second aspect of the invention, there is provided a composition comprising an agent as described above which is capable of inhibiting IL-36 activation via proteolytic processing and a suitable pharmaceutical excipient.

The agents described herein can be formulated into pharmaceutical compositions that further comprise a pharmaceutically acceptable carrier, diluent, adjuvant or vehicle. In one embodiment, the present invention relates to a pharmaceutical composition comprising an agent of the invention described herein, and a pharmaceutically acceptable carrier, diluent, adjuvant or vehicle. In one embodiment, the present invention is a pharmaceutical composition comprising an effective amount of an agent of the present invention and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

Suitable pharmaceutical excipients include but are not limited to binders, disintegrants, fillers, flavours, colours, lubricants, glidants, sorbents and/or preservatives.

It will be understood that the agent capable of inhibiting IL-36 activation via proteolytic processing may be adapted for administration in the following alternative forms tablets, capsules, oral liquids, transdermal patches, injectable products, implants, eye products, nasal products, inhalers and suppositories.

The compositions of the invention can also be in liquid form, for example, solutions, emulsions, suspensions or syrups.

The invention is also directed to agents which target and/or mimic one or more of the following IL-36 protease cleavage sites
the IL-36β protease cleavage site NPQR$_5$ and/or one or more of upstream amino acid residues EAAP;
the IL-36γ cleavage site GRAV$_{15}$ and/or one or more of upstream amino acid residues YQSM; and/or
the IL-36α protease cleavage sites MEK$_3$ or and MEKA$_4$ and/or one or more of upstream residues LKID.

The invention is also directed to agents which inhibit IL-36 activation via proteolytic processing by preventing and/or inhibiting the activity of IL-36 activating proteases or activators thereof selected from elastase, cathepsin G, cathepsin K, proteinase-3 and DPPI (Cathepsin C).

Preferably, the agent comprises or consists of the peptides listed in Tables 1 and 3, or derivatives, peptidomimetic or combinations thereof.

According to a third aspect of the invention, there is provided a comprising an agent capable of inhibiting IL-36 activation via proteolytic processing and a suitable pharmaceutical excipient. It will be understood that the agent, is as defined above, and inhibits IL-36 activation by binding to the IL-36 protease cleavage sites required for activation of IL-36; or the agent prevents and/or inhibits the activity of IL-36 activating proteases or activators thereof.

Ideally, the composition is for topical treatment although other administration routes, for example oral, parenteral, intravenous are also contemplated.

According to one embodiment, there is provided a topical inflammatory composition, ideally a skin disorder treatment composition, comprising an agent as described above which is capable of inhibiting IL-36 activation via proteolytic processing and a suitable pharmaceutical excipient.

Preferably, the composition is adapted for the treatment and prevention of inflammatory skin disorders and comprises an agent capable of inhibiting IL-36 activation via proteolytic processing and a suitable pharmaceutical excipient.

The topical treatment composition may be in the form of a cream or gel. Accordingly, the suitable pharmaceutical excipient may be any conventional topical pharmaceutical excipient.

Ideally, the agent is a small molecule, peptide, polypeptide, protein, siRNA, sgRNA, and/or antibody. For example, the agent may be selected from Table 1, 2 or 3.

According to a fourth aspect of the invention, there is provided an agent as described above which is capable of inhibiting IL-36 activation via proteolytic processing for use in the manufacture of a medicament for the treatment and/or reduction of inflammation, preferably inflammatory skin disorders, in a subject.

According to a fifth aspect of the invention, there is provided a method for the treatment and/or reduction of inflammation in a subject, preferably inflammation of barrier organs, including inflammation of the skin, gut and/or lung, comprising administering an effective amount of an agent as described above which is capable of inhibiting IL-36 proteolytic processing to a subject.

The subject is a subject suffering from an inflammatory skin disorder selected from psoriasis, including Psoriasis vulgaris; dermatitis and/or acne, sebaceous cysts, vasculitis, eczema, dermatitis, granuloma annulare, lichen planus, bullous pemphigoid, molluscum contagiosum, dermatomyositis and ichthyosis vulgaris.

Ideally, plaque, guttate, palmoplantar, generalized pustular and/or arthritic psoriasis may be treated in accordance with the invention. Psoriasis will be understood to cover all forms of psoriasis including psoriasis vulgaris, plaque psoriasis, guttate psoriasis, flexural (inverse) psoriasis, erythroderma psoriasis, generalized pustular psoriasis, arthritic psoriasis, palmoplanter pustulosis and psoriatic nail disease.

The subject is ideally a mammal, preferably a human.

Preferably, the agent capable of inhibiting IL-36 proteolytic processing may be applied topically to the subject.

The present invention will now be described by the following non-limiting figures and examples.

FIGURE LEGENDS

The Invention will be more clearly understood from the following description of embodiments thereof, given by way of example only, with references to the accompanying drawings, in which—

FIG. 1 (A) is a schematic of modified forms of IL-36α, IL-36β and IL-36γ where a caspase-3-processing motif (DEVD) was inserted into the IL-36 sequence, N-terminal to the known processing sites. (B) IL-36α/β/γ and DEVD-IL-36α/β/γ were incubated at 37° C. for 2 h, either alone or in the presence of indicated concentrations of recombinant caspase-3, followed by analysis by immunoblot.

FIG. 2 (A) are graphs showing HeLa$^{Vector}$ and HeLa$^{IL36R}$ stimulated with caspase-3 cleaved DEVD-IL36α, β and γ. After 24 h, cytokine concentrations in culture supernatants were determined by ELISA. (B) are graphs showing HeLa$^{IL36R}$ stimulated with full-length or caspase-3 cleaved DEVD-IL-36α, β and γ. At indicated time-points cytokine concentrations in culture supernatants were determined by ELISA.

FIG. 3 are graphs showing HeLa$^{IL36R}$ were stimulated with (A) full-length DEVD-IL-36α or caspase-3 cleaved DEVD-IL-36α, (B) full-length DEVD-IL-36β or caspase-3 cleaved DEVD-IL-36β, (C) full-length DEVD-IL-36γ or caspase-3 cleaved DEVD-IL-36γ at the indicated concentrations. (D) showing HaCat stimulated with full-length DEVD-IL-36β or caspase-3 cleaved DEVD-IL-36β at the indicated concentrations. After 24 h, cytokine concentrations in culture supernatants were determined by ELISA.

FIG. 4 (A) are photographs showing primary blood derived neutrophils stimulated in the presence or absence of PMA (50 nM) for 3 h. (B) are graphs showing HeLa$^{IL36R}$ were stimulated with 500 pM Il36α, β and γ pre-incubated for 2 h at 37° with indicated dilutions of either control or PMA-activated degranulates. After 24 h, cytokine concentrations in culture supernatants were determined by ELISA.

FIG. 5 are graphs showing HeLa$^{IL36R}$ stimulated with IL36α, IL36β and IL36γ, pre-incubated for 2 h at 37° with neutrophils degranulates in the presence or absence of PMSF (1 mM), leupeptin (10 μg/ml), aprotinin (10 mg/ml), Cathepsin G inhibitor 1 (10 μM), zVAD-fmk (10 μM), Elastase Inhibitor IV (10 μM), ALLN (5 μM), Antipain (100 μM). After 24 h, cytokine concentrations in culture supernatants were determined by ELISA.

FIG. 6 (A and B) are graphs showing Control and PMA-activated neutrophil degranulates that were pre-incubated with biotin-VAD-CMK (10 μM), biotin-FLF-CMK (10 μM) or Elastase Inhibitor IV (10 μM) for 30 min on ice followed by incubation with strepavidin agarose beads. Degranulates were subsequently assessed for Cathepsin G activity by FLF-sBzl hydrolysis assay (A) or Elastase activity was assessed by AAPV-AMC hydrolysis. HeLa$^{IL36R}$ were stimulated with IL36β (A) or IL36γ (B) pre-incubated for 2 h at 37° with mock, biotin-VAD-CMK (10 μM) or biotin-FLF-CMK (10 μM) treated degranulates. After 24 h, cytokine concentrations in culture supernatants were determined by ELISA.

FIG. 7 (A) are graphs showing hydrolysis of the synthetic caspase peptide (WEHD-AMC), by caspase-1; the caspase peptide (DEVD-AMC), by caspase-3; the cathepsin peptide (Suc-FLF-sBzL), by purified neutrophil cathepsin G; the elastase peptide (AAPV-AMC), purified neutrophil elastase. (B) are graphs showing HeLa$^{IL36R}$ stimulated with 500 pM IL-36α, β and γ pre-incubated for 2 h at 37° with indicated concentrations of recombinant caspase-1,-3 or purified cathepsin-G and elastase. IL-1β p17 served as a positive control for caspase titrations. After 24 hr, cytokine concentrations in culture supernatants were determined by ELISA.

FIG. 8 are graphs showing HeLa$^{IL36R}$ stimulated with a titration of IL-36α, β and γ pre-incubated for 2 hr at 37° with fixed concentrations of purified cathepsin-G (50 nM) and elastase (200 nM). After 24 hr, cytokine concentrations in culture supernatants were determined by ELISA.

FIG. 9 (A) is a Coomassie blue stained gel of recombinant IL-36β that was incubated in the presence or absence of Cathepsin G (50 nM). Indicated fragments were analysed by Edman Degradation sequencing and novel N-termini were identified as ($^6$EAAP) and ($^{54}$SDKE). (B) is schematics representing NPQR$^5$ and DTEF$^{53}$ cleavage motifs within IL-36β and point mutants IL-36β F53A and IL-36β R5A.

FIG. 10 is a Coomassie blue stained gel of recombinant Recombinant IL-36β, IL-36β$^{F53A}$ and IL-36β$^{R5A}$ were incubated with fixed concentration of cathepsin-G, as indicated, followed by analysis by SDS-PAGE and Coomassie stain. Representative gel is shown from at least two independent experiments.

FIG. 11 (A) are graphs showing HeLa$^{IL36R}$SEAP stimulated with a titration of IL36β and IL36β$^{R5A}$ pre-incubated for 2 h at 37° with cathepsin-G (50 nM). After 24 h, NF-kB activity was measured as a fold induction of SEAP in the supernatant and cytokine concentrations in culture supernatants were determined by ELISA. (B) HeLa$^{IL36R}$ stimulated with 500 pM of IL36β, IL-36β$^{R5A}$ and IL36β$^{F53A}$ pre-incubated for 2 h at 37° with a titration of cathepsin-G. After 24 h, NF-kB activity was measured as a fold induction of SEAP in the supernatant and cytokine concentrations in culture supernatants were determined by ELISA.

FIG. 18 are photographs of graphs showing Organotypic skin reconstructs cultivated at the air to liquid interface were topically stimulated with either cathepsin-G alone (We applied 2 μl in 10 μl MM), 2 nM IL-36β$^{FL}$ or IL-36β$^{CatG}$ in a volume of 10 μl MM, respectively, every other day. Application of 10 μl MM only served as negative control. After 15 days skin reconstructs were harvested, fixed in paraffin, and sections stained with H&E, against filaggrin, involucrin, cytokeratin 10 and 14 as indicated to display epidermal thickness and differentiation.

Figure 19:
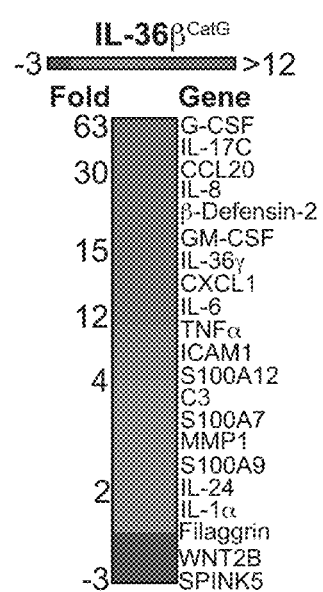

FIG. 19 is a gene expression heat map of IL-36β$^{CatG}$ induced in primary keratinocytes at 8 h.

Figure 20:
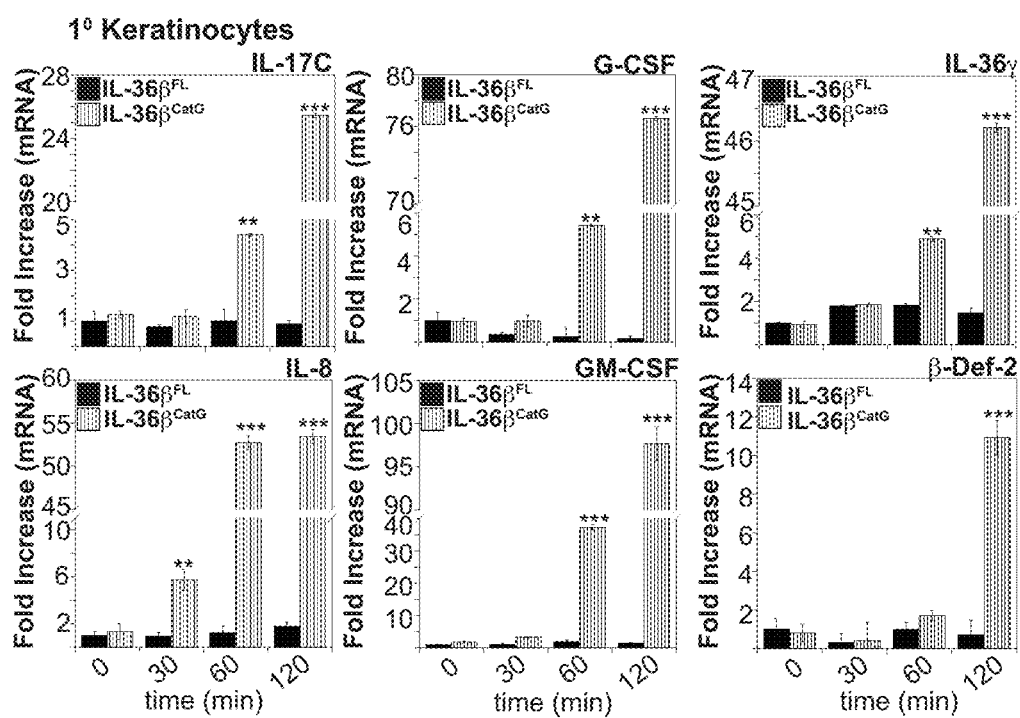

FIG. 20 are graphs showing primary keratinocytes stimulated with IL-36β$^{FL}$ (5 nM) and IL-36β$^{CatG}$ (5 nM). At indicated time-points mRNA levels of cytokine were determined by RT-PCR.

Figure 21:
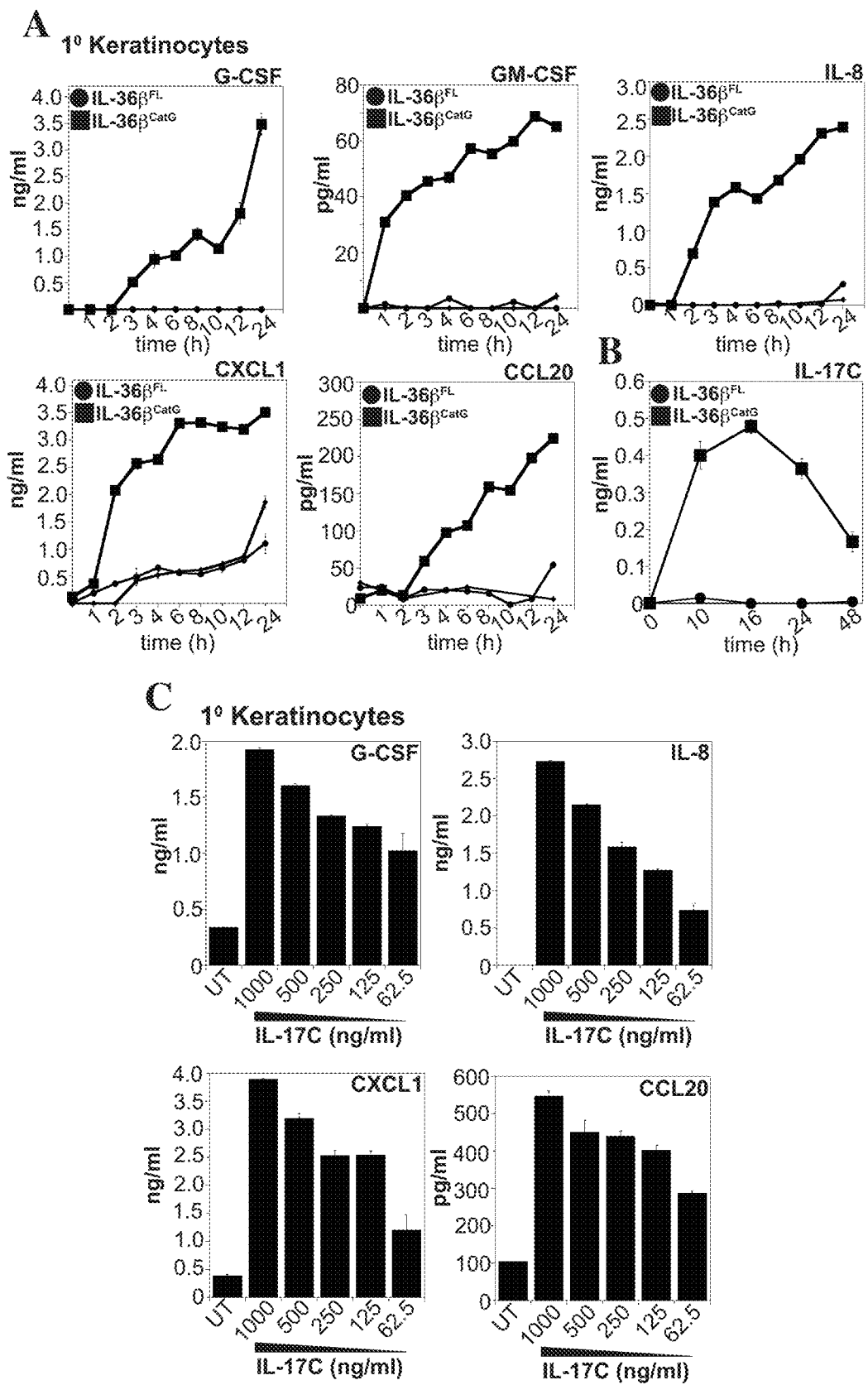

FIG. 21 (A-B) are graphs showing primary keratinocytes stimulated with IL-36β$^{FL}$ (5 nM) and IL-36β$^{CatG}$ (5 nM). At indicated time-points levels of cytokine were determined by ELISA. (C) graphs showing primary keratinocytes stimulated with indicated concentrations of recombinant IL-17C. After 48 h, levels of cytokine were determined by ELISA.

FIG. 22 are immunoblots showing the specificity and cross-reactivity of IL-36 rabbit polyclonal antibodies tested against indicated protein amounts of recombinant IL-36 ligands.

FIG. 23 (A) are immunoblots showing Primary keratinocytes treated with a titration of IL-36β$^{CatG}$ (10, 5, 2.5 nM), PMA (40, 20, 10 nM) and Poly:IC (100, 50, 25 mg/ml). Recombinant IL-36 (500 pg) serves as a positive control for each immunoblot. (B) Primary keratinocytes treated with fixed concentrations of IL-36β$^{CatG}$ (5 nM), PMA (20 nM) and Poly:IC (100 μg/ml) over indicated time-points. Recombinant IL-36 (500 pg) serves as a positive control for each immunoblot.

Figure 24:
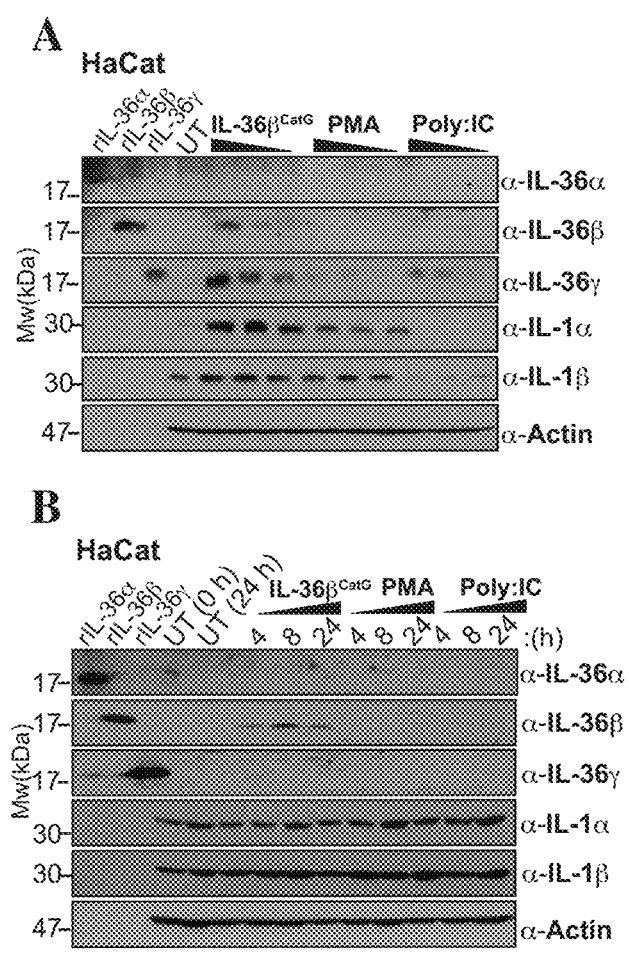

FIG. 24 (A) are immunoblots showing HaCat treated with a titration of IL-36β$^{CatG}$ (10, 5, 2.5 nM), PMA (40, 20, 10 nM) and Poly:IC (100, 50, 25 mg/ml). Recombinant IL-36 (500 pg) serves as a positive control for each immunoblot. (B) HaCat treated with fixed concentrations of IL-36β$^{CatG}$ (5 nM), PMA (20 nM) and Poly:IC (100 μg/ml) over indicated time-points. Recombinant IL-36 (500 pg) serves as a positive control for each immunoblot.

Figure 25:
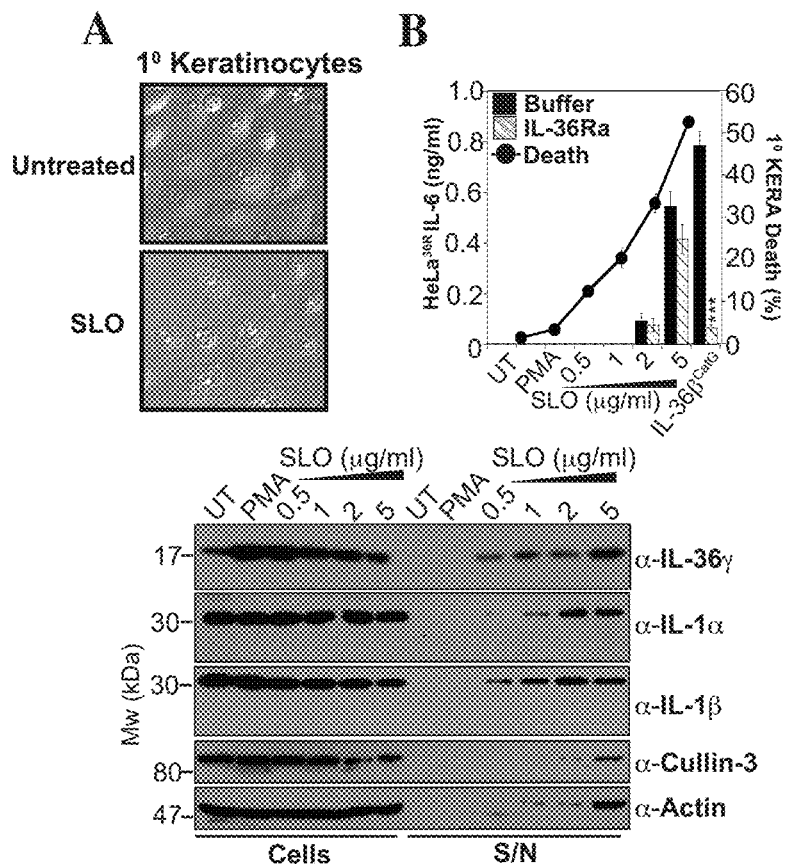

FIG. 25 (A) are photographs showing primary keratinocytes incubated in the presence or absence of PMA (20 nM) for 12 h, followed by 1 h incubation with SLO (5 μg/ml). (B) is a graph showing primary keratinocytes incubated with indicated concentrations of SLO, followed by transfers of the supernatants onto Hela$^{IL36R}$ cells. After 24 h, cytokine concentrations in culture supernatants were determined by ELISA. Cell death is measured by annexin V/PI staining and quantified by flow cytometry. Cells and supernatants were analysed for indicated proteins by immunoblot.

Figure 26:
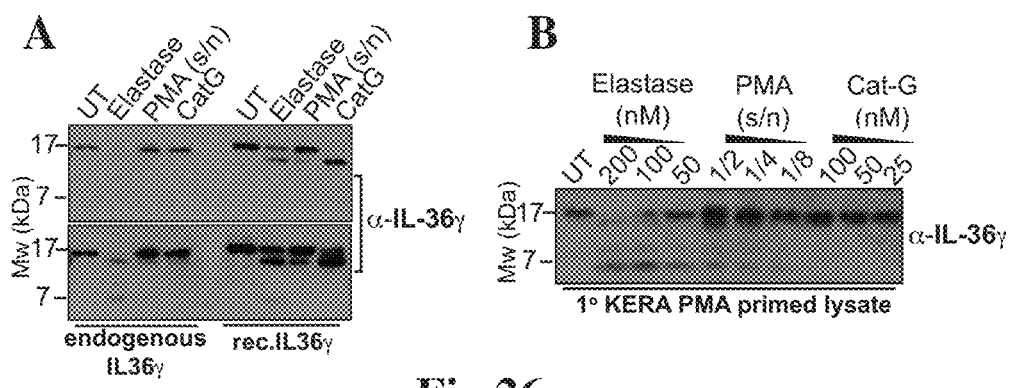

FIG. 26 (A) is an immunoblot showing endogenous and recombinant IL-36γ incubated for 1 h at 37° with buffer, elastase (100 nM), cathepsin-G (50 nM), and neutrophil degranulate (1/4 dilution). (B) is an immunoblot showing endogenous IL-36γ incubated for 1 h at 37° with indicated concentrations of elastase, cathepsin-G and neutrophil degranulate.

Figure 27:
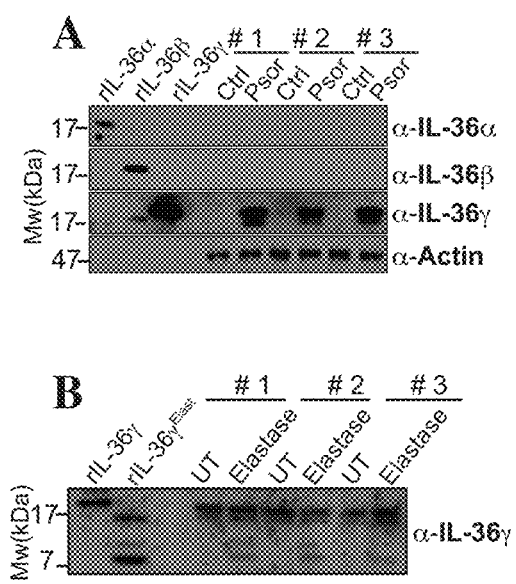

FIG. 27 (A) is an immunoblot of control versus psoriatic biopsy samples, analysed for indicated proteins. Recombinant IL-36 (500 pg) serves as a positive control for each immunoblot. (B) is an immunoblot showing endogenous IL-36γ from psoriatic skin incubated for 1 h at 37° in the presence or absence of elastase (100 nM).

Figure 28:
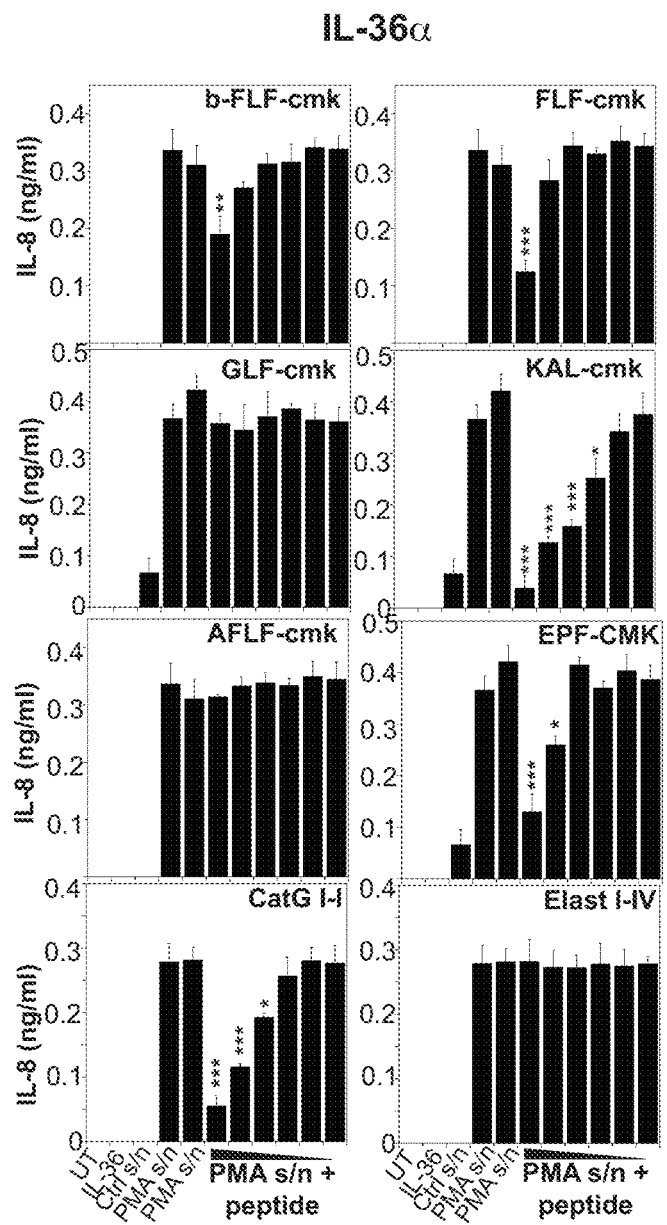

FIG. 28 are graphs showing Neutrophils degranulates pre-incubated for 30 min on ice in the presence or absence of a titration of peptide (20, 10, 5, 2.5, 1.25, 0.625 μM) followed by addition of IL36α for 2 h at 37°. HeLa$^{IL36R}$ were stimulated for 24 h. IL-8 cytokine concentrations in culture supernatants were determined by ELISA. Note: AFLF, GLF peptides and Elast I-IV serve as negative controls for IL-36α assay.

Figure 29:
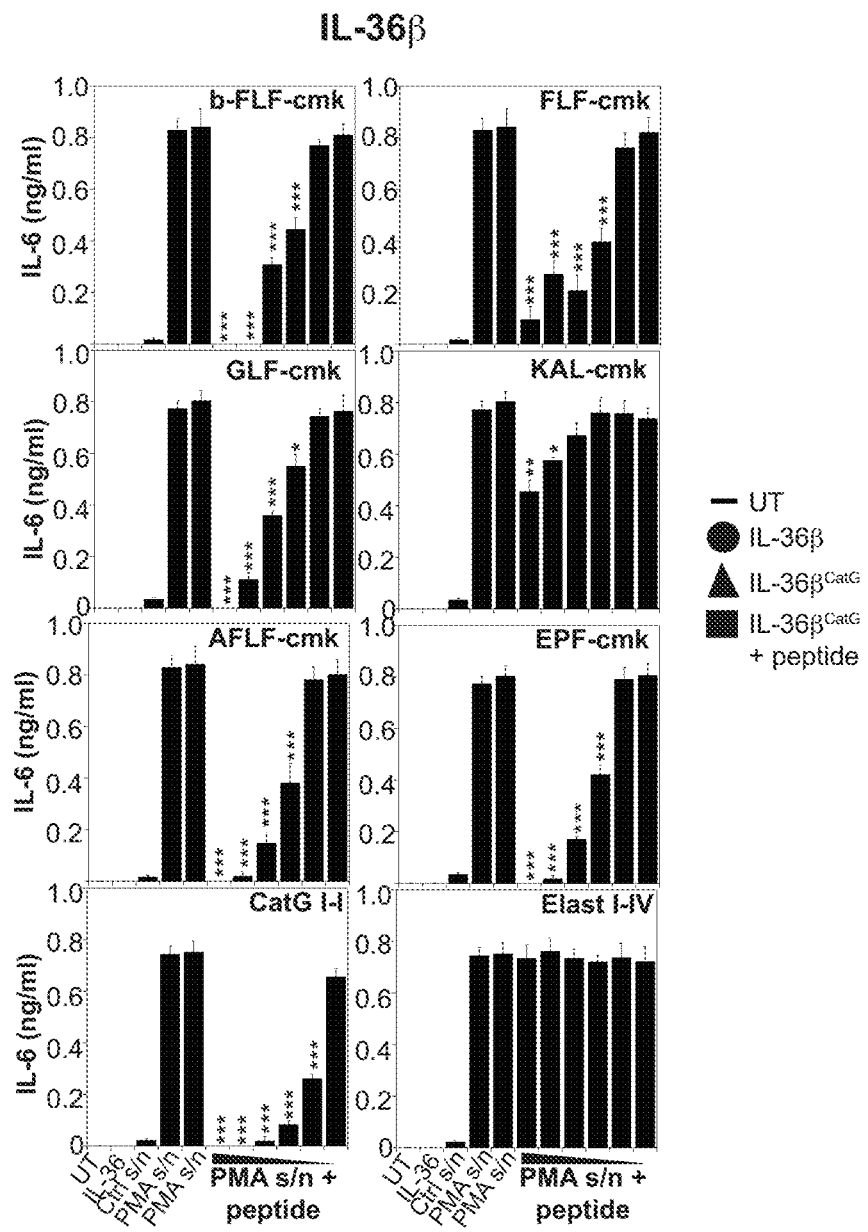

FIG. 29 are graphs showing Neutrophils degranulates pre-incubated for 30 min on ice in the presence or absence of a titration of peptide (20, 10, 5, 2.5, 1.25, 0.625 μM) followed by addition of IL36β for 2 h at 37°. HeLa$^{IL36R}$ were stimulated for 24 h. IL-6 cytokine concentrations in culture supernatants were determined by ELISA. Note: Elast I-IV serves as negative controls for IL-36β assay.

Figure 30:
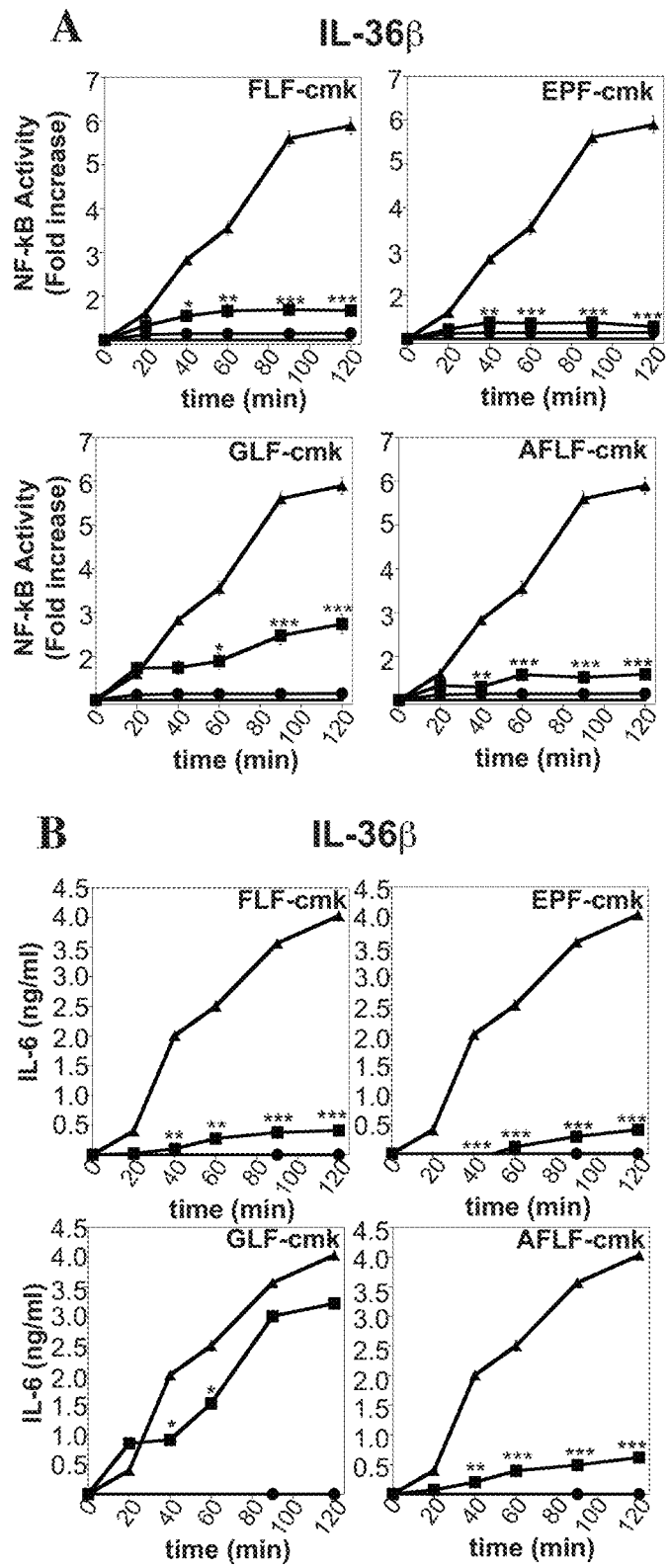

FIG. 30 are graphs showing cathepsin-G were pre-incubated for 30 min on ice in the presence or absence of peptide (10 μM) followed by incubation with IL36β. HeLa$^{IL36R}$SEAP were stimulated with samples of each reaction taken at indicated timepoints. NF-kB activity was measured as a fold induction of SEAP in the supernatant and cytokine concentrations in culture supernatants were determined by ELISA.

Figure 31:
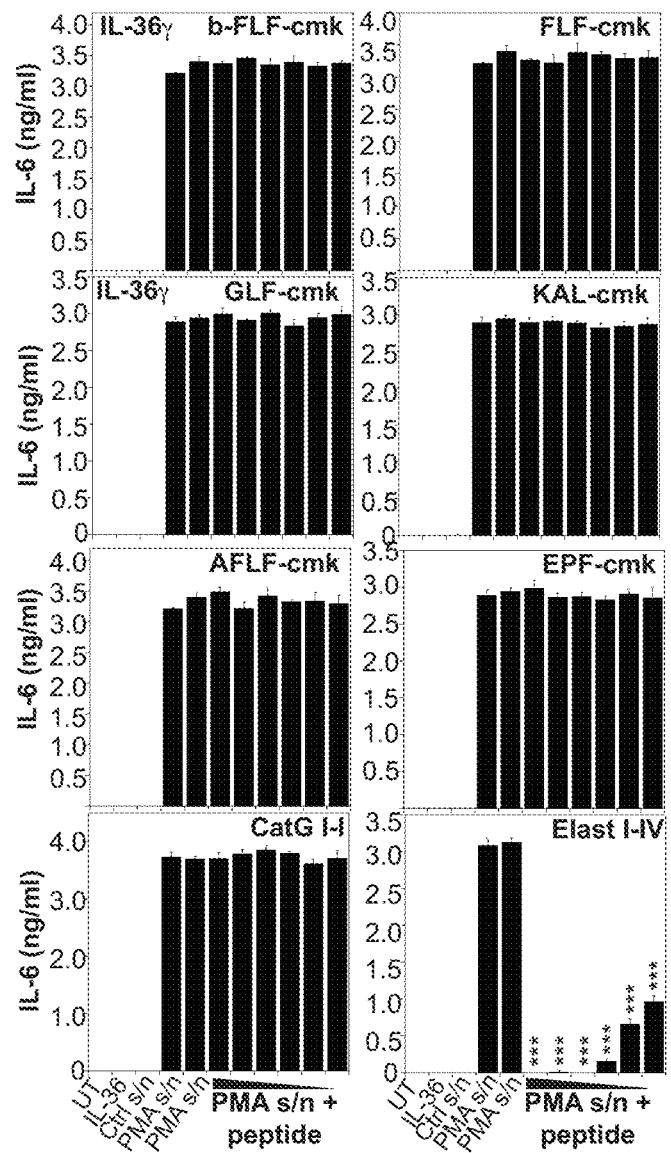

FIG. 31 are graphs showing Neutrophils degranulates pre-incubated for 30 min on ice in the presence or absence of a titration of peptide (20, 10, 5, 2.5, 1.25, 0.625 M) followed by addition of IL36γ for 2 h at 37°. HeLa$^{IL36R}$ were stimulated for 24 h. IL-6 cytokine concentrations in culture supernatants were determined by ELISA. Note: b-FLF, FLF, GLF, KAL, AFLF, EPF peptides and CatG I-1 serve as negative controls for IL-36γ assay.

Figure 32:
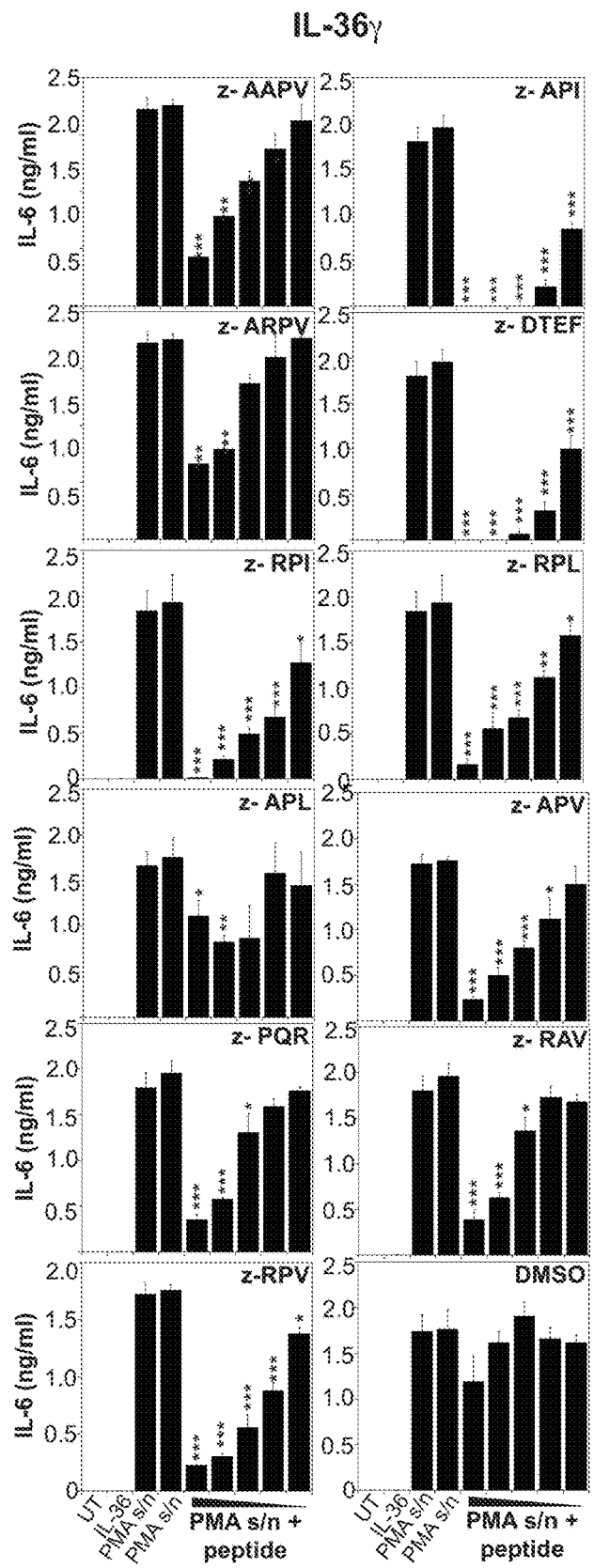

FIG. 32 are graphs showing Neutrophils degranulates pre-incubated for 30 min on ice in the presence or absence of a titration of peptide (200, 100, 50, 25, 12.5 μM) followed by addition of IL36γ for 2 h at 37°. HeLa$^{IL36R}$ were stimulated for 24 h. IL-6 cytokine concentrations in culture supernatants were determined by ELISA.

Figure 33:
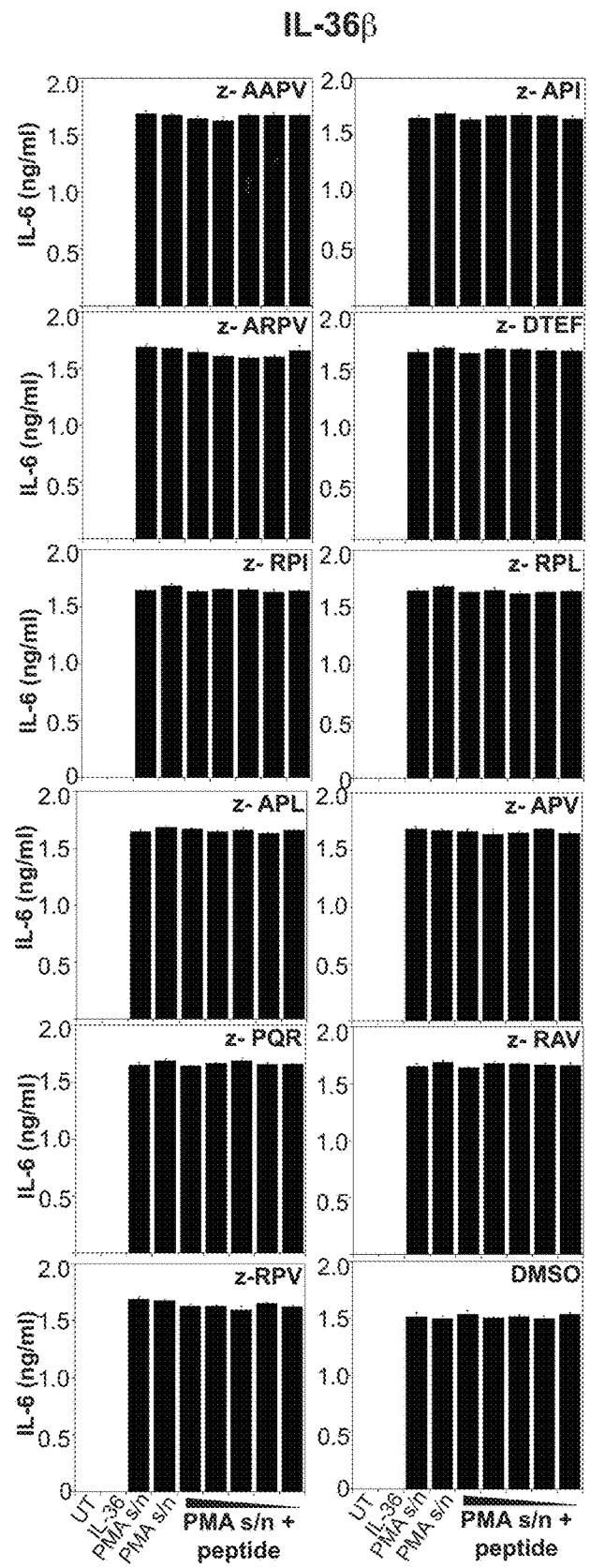

FIG. 33 are graphs showing Neutrophils degranulates pre-incubated for 30 min on ice in the presence or absence of a titration of peptide (200, 100, 50, 25, 12.5 μM) followed by addition of IL36β for 2 h at 37°. HeLa$^{IL36R}$ were stimulated for 24 h. IL-6 cytokine concentrations in culture supernatants were determined by ELISA. Note: AAPV, API, ARPV, DTEF, RPI, RPL, APL, APV, PQR, RAV, and RPV peptides serve as negative controls for IL-36β assay.

Figure 34:
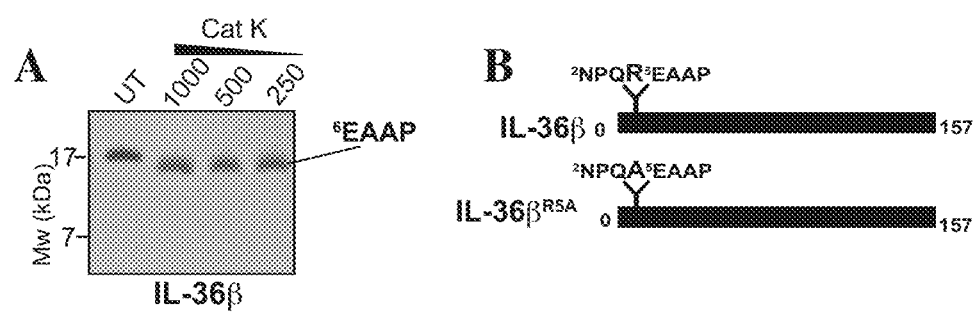

FIG. 34 (A) is a Coomassie blue stained gel of recombinant IL-36β that was incubated with a titration of purified cathepsin K. Indicated fragment was analysed by Edman Degradation sequencing and novel N-terminus was identified as ($^6$EAAP). (B) is schematics representing NPQR$^5$ cleavage motif within IL-36β and the point mutant IL-36β R5A.

Figure 35:
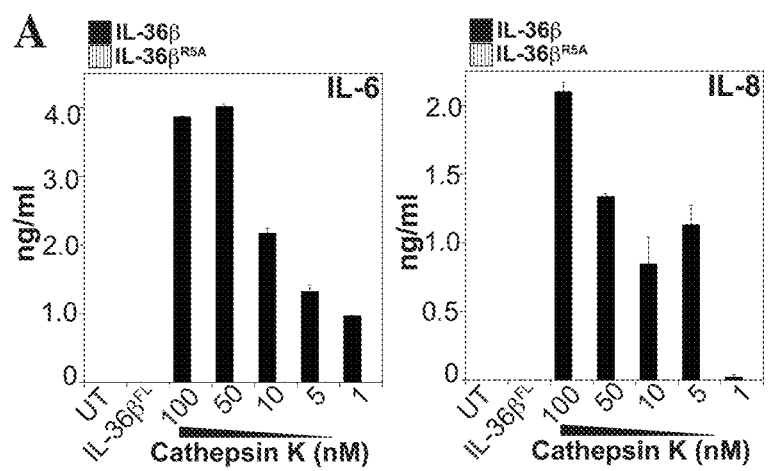

FIG. 35 (A) are graphs showing HeLa$^{IL-36R}$ stimulated with recombinant IL-36β and IL-36β$^{R5A}$ (625 pM) incubated with indicated concentrations of cathepsin K. After 24 hr, cytokine concentrations in culture supernatants were determined by ELISA.

FIG. 36 is the complete DNA coding sequence (SEQ ID No. 3) and corresponding amino acid sequence (SEQ ID No. 4) for the IL-36β gene (Homo sapiens interleukin 1 family, member 8 (eta), mRNA (cDNA clone MGC:126882 IMAGE:8069339), complete cds)

FIG. 37 is the complete DNA coding sequence (SEQ ID No. 5) and corresponding amino acid sequence (SEQ ID No. 6) for the IL-36γ gene (Homo sapiens interleukin 1 family, member 9, mRNA (cDNA clone MGC:119102 IMAGE: 40003612), complete cds)

FIG. 38 is the complete DNA coding sequence (SEQ ID No. 26) and corresponding amino acid sequence (SEQ ID No. 27) for the IL-36α gene (Homo sapiens interleukin 1 family, member 6, mRNA (cDNA clone MGC:129553 IMAGE:40002576), complete cds)

Figure 39:
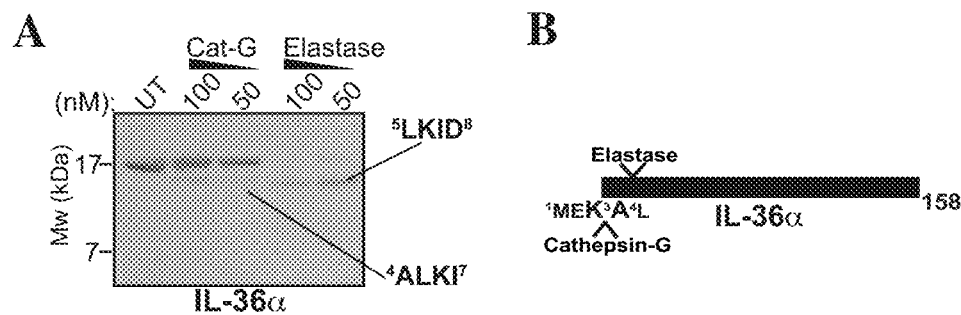

FIG. 39 (A) is a Coomassie blue stained gel of recombinant IL-36α that was incubated with a titration of purified cathepsin-G and elastase. Indicated fragment was analysed by Edman Degradation sequencing and novel N-terminus was identified as ($^4$ALKI) for cathepsin-G and ($^5$LKID) elastase, respectively. (B) is a schematic representing cathepsin-G and elastase cleavage motifs within IL-36α.

Figure 40:
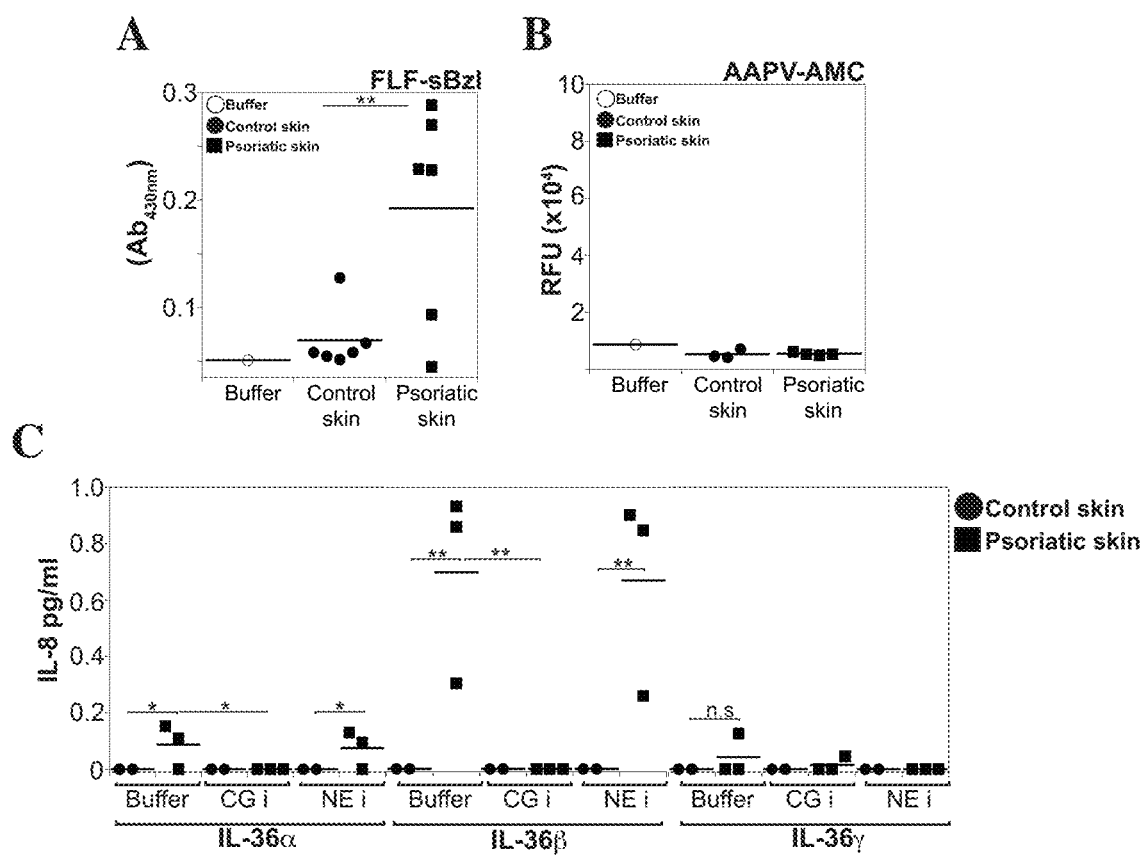

FIG. 40 (A and B) are graphs showing control and psoriatic skin elutes that were assessed for Cathepsin G activity by FLF-sBzl hydrolysis assay (A) or Elastase activity (B). (C) is a graph showing HeLa$^{IL36R}$ cells incubated with equal concentrations of IL-36α, β, γ cytokines (500 pM) that had been pre-incubated for 2 h at 37° with either control or psoriatic skin elutes in the presence or absence of either cathepsin G inhibitor 1 (10 μM) or elastase inhibitor IV (10 μM). IL-8 cytokine concentrations in culture supernatants were determined by ELISA.

Figure 41:
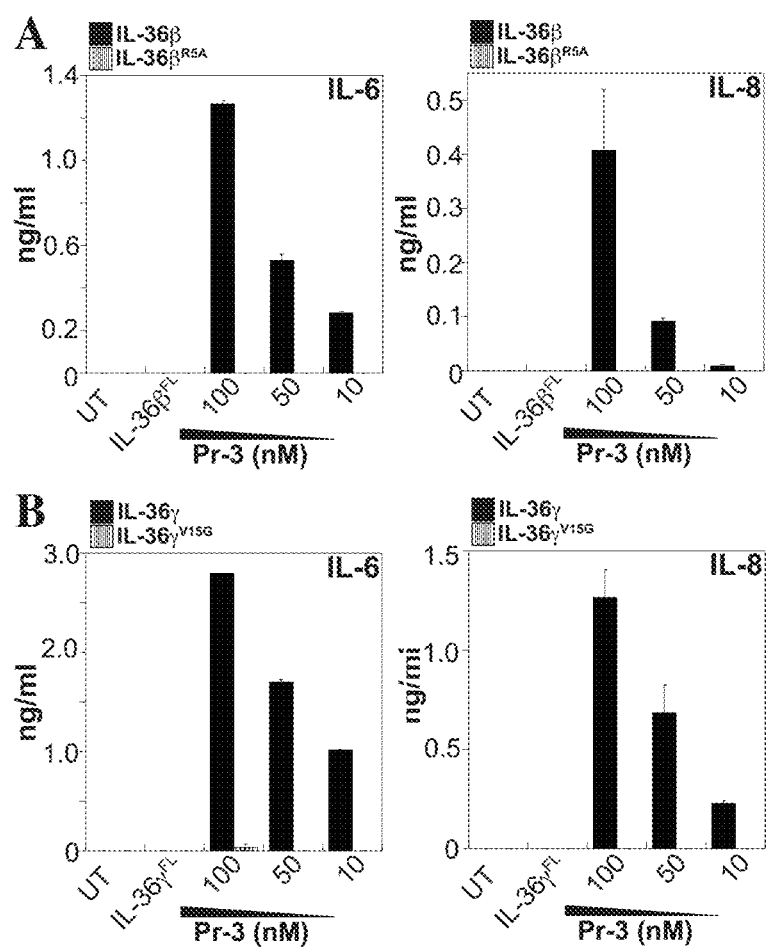

FIG. 41 (A) are graphs showing HeLa$^{IL-36R}$ stimulated with recombinant IL-36β and IL-36β$^{R5A}$ (500 pM) incubated with indicated concentrations of proteinase-3 (B) are graphs showing HeLa$^{IL-36R}$ stimulated with recombinant IL-36γ and IL-36γ$^{V15G}$ (500 pM) incubated with indicated concentrations of proteinase-3. After 24 hr, cytokine concentrations in culture supernatants were determined by ELISA.

EXPERIMENTAL PROCEDURES

Reagents

Polyclonal antibodies were generated against IL-36α, β and γ by repeated immunization of rabbits with the full-length recombinant IL-36 proteins (Biogenes, Germany). anti-IL-1α and anti-IL-1β were purchased from R&D systems (UK). anti-Actin (clone C4) was from MP Biomedicals, anti-Bax (clone 6A7) was from Sigma, anti-Cullin-3 was from BD antibodies. Synthetic peptides, Ac-DEVD-AMC (SEQ ID No. 9), Ac-WEHD-AMC (SEQ ID No. 10), and biotin-VAD-FMK were all purchased from Bachem (Germany); Suc(oMe)-AAPV-AMC (SEQ ID No. 11) was purchased from Peptanova (Germany); biotin-VAD-FMK was purchased from ICN (UK). Novel synthetic peptides biotin-FLF-CMK, z-FLF-CMK, z-AFLF-CMK, z-EPF-CMK, z-GLF-CMK, z-KAL-CMK, z-GLK-CMK and z-GLW-CMK were synthesised by Boston Open Labs (USA). Chemical inhibitors Cathepsin G Inhibitor I and Elastase Inhibitor IV were purchased from Calbiochem (UK). Purified Neutrophil-derived Cathepsin G was purchased from Calbiochem (UK). Purified Neutrophil-derived Elastase was purchased from Serva (Germany). Unless otherwise indicated, all other reagents were purchased from Sigma (Ireland) Ltd.

Expression and Purification of Recombinant IL-36 and Caspases

Full-length poly-histidine-tagged IL-36α, β and γ proteins was generated by cloning the human coding sequence in frame with the poly-histidine tag sequence in the bacterial expression vector pET45b. Protein was expressed by addition of 600 μM IPTG to exponentially growing cultures of BL21 strain *E. coli* followed by incubation for 3 h at 37° C. Bacteria were lysed by sonication and poly-histidine tagged proteins were captured using nickel-NTA agarose (Qiagen, UK), followed by elution into PBS, pH 7.2, in the presence of 100 mM imidazole. Modified forms of IL-36 where cloned that included a caspase-3-processing motif (DEVD) into the IL-36 sequences, N-terminal to the known processing sites[22]. All IL-36 mutants were expressed and purified in the same way. Recombinant poly-histidine-tagged caspases-1, and -3, were also expressed and purified as described above.

Site-Directed Mutagenesis

Site-directed mutagenesis was carried out using the QuikChange kit (Stratagene). Mutagenesis of IL-36 genes was verified by sequencing (Eurofins MWG Operon).

Coupled In Vitro Transcription/Translation Reactions

In vitro transcription/translation reactions were carried out using purified plasmid templates added to a rabbit reticulocyte lysate system (Promega, UK).

Immunoblotting of Lysates and Precipitated Supernatants

To precipitate protein from supernatant, TCA was added at a 1:4 ratio to supernatant volume (250 μl to 1 ml supernatant) and incubated on rotation for 10 min. Supernatants were centrifuged at 15,000 g for 10 min. Top layer was removed without disturbing the pellet. 200 μl pre-chilled acetone was added to each pellet and mixed by several inversions. Samples were centrifuged for a further 10 min at 15,000 g. Samples were then put on heating block to burn off the acetone. 1×SDS-PAGE loading buffer (Tris.Cl, 50 mM, SDS, 2%, Glycerol 10%, Bromophenol Blue, 0.05%, β-mercaptoethanol, 2.5%) was added to each sample pellet. Samples were then boiled for a further 5 mins. Cell lysates were prepared using SDS-PAGE loading buffer and were electrophoresed on 8-13% SDS-polyacrylamide gels followed by transfer onto nitrocellulose membranes. Protein expression was subsequently examined by immunoblotting with the appropriate antibodies.

Purification of Primary Cell Populations and Preparation of Degranulates

Primary neutrophils were purified from donor human blood using the plasma-Percoll gradient method. Purity of cell preparations (>90%) was determined by Hematoxylin and Eosin staining of cytospins. To prepare degranulates, neutrophils (10$^7$ per treatment) were stimulated in the presence or absence of 50 nM PMA in HBSS/0.25% BSA for 1-3 h at 37° C. in a humidified atmosphere with 5% $CO_2$. Supernatants were harvested and clarified by centrifugation. Degranulate aliquots were stored at −80°.

Protease Activity Assays

Reactions (50 μl final volume) were carried out in protease reaction buffer (50 mM Hepes, pH 7.4/75 mM NaCl/0.1% CHAPS/2 mM DTT) containing 50 μM Ac-DEVD-AFC, Ac-WEHD-AMC, Suc(oMe)-AAPV-AMC. Samples were measured by using an automated fluorimeter (Spectrafluor Plus; TECAN) at wavelengths of 430 nm (excitation) and 535 nm (emission). For suc-FLF-sBzl assay, substrate was diluted to a final concentration of 300 μM in protease reaction buffer (50 mM Hepes, pH 7.4/75 mM NaCl/0.1% CHAPS/DTNB 300 μM). Samples were measured by automated fluorimeter (Spectrafluor Plus; TECAN) at an absorbance wavelength of 430 nM.

Protease Cleavage Assays

Reactions (40-100 μl final volume) were carried out in protease reaction buffer (50 mM Hepes, pH 7.4/75 mM NaCl/0.1% CHAPS) for 2 h at 37°.

Measurement of Cytokines and Chemokines

Cytokines and chemokines were measured from cell culture supernatants using specific ELISA kits obtained from R&D systems (human IL-6, IL-8, CXCL1, MCP-1, IL-17C). Each assay was repeated a minimum of three times and all cytokine assays were carried out using triplicate samples from each culture.

Cell Culture

HeLa were cultured in RPMI media (Gibco), supplemented with 5% fetal calf serum (FCS). HaCat were cultured in DMEM (Gibco) supplemented with FCS (10%). Primary neonatal foreskin derived Keratinocytes P0 were purchased from Cell Systems (Germany) and cultured in serum-free Dermalife K media (Cell Systems, Germany). HeLa.vector or HeLa.IL-36R cell lines were generated by transfection with pCDNA3 or pCDNA3.IL-1rrp2 followed by selection using G-418 antibiotic (Sigma). IL-1rrp2 over-expressing clones were confirmed by immunoblotting and the final clone selected by demonstration of acquired responsiveness to active forms of IL-36. All cells were cultured at 37° C. in a humidified atmosphere with 5% $CO_2$.

Generation and Immunhistochemical Analyses of Organotypic Skin Equivalents.

Skin models were generated using 24 well inserts (Nunclon™ Δ, Nunc, Rochester, N.Y.) in 24 well plates (Greiner-bio-one). Per insert $1\times10^5$ fibroblasts in GNL (322.5 ml 2×DMEM; 7.5 ml 3 M HEPES; 1.25 ml chondroitin-4-sulfate; 1.25 ml chondroitin-6-sulfate; 7.5 ml FCS) were mixed 1:3 with collagen I isolated from rat tails to a final volume of 500 µl and cultivated in DMEM/4.5 g/l glucose/1% L-glutamine/10% FCS/-L-pyruvate over night at 37° C. Next day dermal gels were equilibrated with EGM/10% FCS/1% PenStrep/10 mg/ml gentamycine for 2 h at 37° C. The medium was withdrawn and $1\times10^5$ keratinocytes in EGM carefully seeded on top and incubated for 1.5 h at 37° C. to allow adhesion. Subsequently, skin equivalent were covered with EGM and cultivated for 7 days—changing the medium every other day. At day 7 skin equivalents were transferred to 6 well plates and cultivated/treated at the air-liquid interface in MM for 15 more days at 37° C., changing the medium every other day. Skin reconstructs were fixed in Roti-Histofix (Roth; Karlsruhe, Germany) for 3 h at RT released from the insert and embedded into paraffin. Sections of 3 µm were cut using a RM 2145-microtome (Leica, Biberach, Germany), transferred onto slides (LABOnord; Greiner-bio-one) for hematoxylin-eosin (HE)-staining or onto sialynized slides (Menzel GmbH, Braunschweig, Germany) for immunhistochemical analysis and dried at 37° C. over night. Sections were released from paraffin using Roticlear (Roth) and subjected to HE-staining at RT or were incubated with primary antibodies against keratin 10 (Dako, Hamburg, Germany), keratin 14, filaggrin (Biomedia, Singapore) and involucrin (Acris, Herford, Germany), respectively, as recommended by the manufacturer at 4° C. over night. Secondary polyclonal goat-anti-mouse-FITC (Dako) or goat-anti-mouse-Cy3 IgG (Jackson ImmunoResearch) antibodies were used, slides mounted in Pro-Long® Gold with or without DAPI (MolecularProbes® Life Technologies™) and analyzed using an Apotom1-Axio Imager and CEN software (Zeiss).

Gene Expression Microarray

Primary human neonatal foreskin-derived Keratinocytes (P3) were used for gene expression analysis. Primary Keratinocytes were stimulated with IL-36β for 8 and 24 h timepoints. Cells were harvested with RNAprotect cell reagent (Qiagen) and stored at −80°. Analysis of samples were performed using SurePrint G3 Human Gene Expression 8x60K v2 Microarray using a one-color based hybridization protocol and preformed by IMGM Laboratories (Germany).

RNA Analysis by Real-Time PCR (RT-PCR)

RNA was extracted from cells using the RNeasy Kit (Qiagen) as per manufacturer's instructions. cDNA was generated using the Omniscript RT Kit (Qiagen) and used to seed RT-PCR reactions (LightCycler® FastStart DNA Master Mix Sybr Green I). Quantification of cytokine gene products was preformed using the Roche Light Cycler 1.5 software and normalized to the β-Actin housekeeping gene.

Primers for RT-PCR

Primer sequence design for cytokine gene expression by real-time RT-PCR.

IL-17C Forward
(SEQ ID No. 12)
5' TTG GAG GCA GAC ACC CAC C 3'

IL-17C Reverse
(SEQ ID No. 13)
5' GAT AGC GGT CCT CAT CCG TG 3'

IL-36γ Forward
(SEQ ID No. 14)
5' GAA ACC CTT CCT TTT CTA CCG TG 3'

IL-36γ Reverse
(SEQ ID No. 15)
5' GCT GGT CTC TCT TGG AGG AG 3'

IL-8 Forward
(SEQ ID No. 16)
5' TCTGCAGCTCTGTGTGAAGG 3'

IL-8 Reverse
(SEQ ID No. 17)
5' ACT TCT CCA CAA CCC TCT GA 3'

G-CSF Forward
(SEQ ID No. 18)
5' GCT TAG AGC AAG TGA GGA AG 3'

G-CSF Reverse
(SEQ ID No. 19)
5' AGG TGG CGT AGA ACG CGG TA 3'

GM-CSF Forward
(SEQ ID No. 20)
5' GAG CAT GTG AAT GCC ATC CAG GAG 3'

GM-CSF Reverse
(SEQ ID No. 21)
5' CTC CTG GAC TGG CTC CCA GCA GTC AAA 3'

β-defensin-2 Forward
(SEQ ID No. 22)
5' ATG AGG GTC TTG TAT CTC CT 3'

β-defensin-2 Reverse
(SEQ ID No. 23)
5' TAT CTT TGG ACA CCA TAG TT 3'

β-Actin Forward
(SEQ ID No. 24)
5' ATG TTT GAG ACC TTC AAC AC 3'

β-Actin Reverse
(SEQ ID No. 25)
5' CAC GTC ACA CTT CAT GAT GG 3'

Psoriatic Patient Samples 4 mm punch biopsies were obtained from 3 individuals presenting with clinical features of psoriais. The punch biopsies were obtained from uninvolved as well as involved areas of epidermis. Samples were homogenized using a dounce homogenizer in protease reaction buffer (50 mM Hepes, pH 7.4/75 mM NaCl/0.1% CHAPS. 1×SDS-PAGE loading buffer (Tris.Cl, 50 mM, SDS, 2%, Glycerol 10%, Bromophenol Blue, 0.05%, β-mercaptoethanol, 2.5%) was added to each sample pellet. Samples were then boiled for a further 5 mins. Cell lysates were prepared using SDS-PAGE loading buffer and were electrophoresed on 8-13% SDS-polyacrylamide gels followed by transfer onto nitrocellulose membranes. Protein expression was subsequently examined by immunoblotting with the appropriate antibodies.

Tape-Strip Samples from Control and Psoriatic Skin

Fixomull (2 cm×2 cm) adhesive tape strips were applied to a healthy or psoriatic skin, under firm pressure for 10 seconds. The tape-strip was placed in sterile 1.5 ml eppendorfs and eluated with protease reaction buffer (50 mM Hepes, pH 7.4/75 mM NaCl/0.1% CHAPS) under constant rotation for 1 h at 4° C. Sample eluates were stored at −80° C. Enzymatic assays and bioassays were setup using control and psoriatic eluates as described above.

Assessment of Agents as Capable of Inhibiting IL-36 Activation Via Proteolytic Processing To identify whether IL-36 isoforms are proteolytically processed and activated by a particular protease, IL-36 is incubated with the protease for approximately 2 hours at 37° C. The reaction is then added to a cell line and the biological activity of the IL-36 protein is determined by the ability of IL-36 receptor (IL-36R) expressing cells, such as HeLa cells, Primary Keratinocytes, HaCat cells, to secrete factors into the cell culture medium. These secreted factors are quantified by ELISA (as shown in for example, FIG. 4B, FIG. 7, FIG. 8, FIG. 16, FIG. 17, FIG. 21A).

Assessment and Determination of Protease Cleavage Sites

To determine the proteolytic cleavage site(s) that activate IL-36, the protease is incubated with IL-36 for approximately 2 hours at 37° C., and the resulting reaction is analyzed by gel electrophoresis using an SDS-PAGE gel to separate denatured protein by the length of the polypeptide. The SDS-PAGE gel is then transferred onto PDVF membrane. This embeds the protein content of the SDS-PAGE gel onto the PVDF membrane. The PDVF membrane is stained with Coomassie blue. This dye stains the protein content of the PDVF and resolves the IL-36 protein and any cleavage bands are also made visible. These cleavage bands are subsequently excised and analysed by conventional Edman degradation sequencing to determine what is the N-terminus amino acid for the particular cleavage band that has been analysed. This is shown in, for example, IL-36α (see FIG. 39), IL-36β (see FIG. 9-12, FIG. 34) and IL-36γ (see FIG. 13-15).

Once this has been determined, this enables the particular residue(s) to be mutated via site-directed mutagenesis, whereby the cleavage site residue is changed to some other amino acids, typically a Glycine (Gly) or Alanine (Ala) (FIG. 9-12, FIG. 13-15, FIG. 39). The proteolytic reaction is now repeated using this mutant version of IL-36 (whereby the cleavage site has to be changed) with the protease. Again, this is shown FIG. 9-12, FIG. 13-15, FIG. 34, FIG. 39, whereby point mutants within IL-36 block activation by either cathepsin-G, Elastase, proteinase-3 or cathepsin K.

Design of Peptides Mimicking the Protease Cleavage Site for Use as Agents

Based on the cleavage sites identified within the IL-36 isoforms, peptides, including tri-/tetra-peptides, can be designed that mimic these cleavage motifs using conventional techniques.

Typically, a tri-/tetra-peptide will encompass the residues upstream and downstream of the cleavage site. The general nomenclature of cleavage site positions of the substrate were formulated by Schechter and Berger[32-33]. They designate the cleavage site between P1-P1', incrementing the numbering in the N-terminal direction of the cleaved peptide bond (P2, P3, P4, etc.). On the carboxyl side of the cleavage site the numbering is incremented in the same way (P1', P2', P3' etc.).

This has enabled the design and synthesis of suitable peptide. For example, RAV peptide (FIG. 32, second row) mimics the cleavage site of IL-36α $GRAV_{15}$, (G-R-A-V-P1'-P2'-P3'). Additionally, KAL peptide (FIG. 28, second row) mimics the cleavage site of IL-36α $MEK_3AL$, (M-E-K-P1'-P2'-P3') by cathepsin-G and the cleavage site of IL-36α $MEKA_4L$, (M-E-K-A-P1'-P2'-P3') by elastase.

It is standard practice to synthesize peptides that reproduce the P1, P2, P3 or P1, P2, P3 and P4 amino acid residues in the substrate cleavage motif (i.e. the region at which the protease cleaves the substrate) to mimic the substrate itself and therefore compete with the protease for access to the substrate. It is also standard practice to choose chemically similar peptides to those specified in the P1, P2, P3 or P1, P2, P3 and P4 amino acid residues of the substrate to generate alternative peptide mimetics that would achieve the same effect. Thornberry et al., (Thornberry N A, Bull H G, Calaycay J R, Chapman K T, Howard A D, Kostura M J, Miller D K, Molineaux S M, Weidner J R, Aunins J, et al. A novel heterodimeric cysteine protease is required for interleukin-1 beta processing in monocytes. Nature. 1992 Apr. 30; 356(6372):768-74) and Nicholson et al., (Nicholson D W, Ali A, Thornberry N A, Vaillancourt J P, Ding C K, Gallant M, Gareau Y, Griffin P R, Labelle M, Lazebnik Y A, et al. Identification and inhibition of the ICE/CED-3 protease necessary for mammalian apoptosis. Nature. 1995 Jul. 6; 376(6535):37-43) are examples of the approach.

Design of Peptides that Binds an IL-36 Activating Protease or Activator Thereof for Use as Agents Based on the identification of the proteases responsible for activating IL-36 isoforms, peptides, including tri-/tetra-peptides, can be designed that bind these proteases using conventional techniques.

As described above it is standard practice to synthesize peptide which target and/or inhibit a protease (e.g. Thornberry et al., (Thornberry N A, Bull H G, Calaycay J R, Chapman K T, Howard A D, Kostura M J, Miller D K, Molineaux S M, Weidner J R, Aunins J, et al. A novel heterodimeric cysteine protease is required for interleukin-1 beta processing in monocytes. Nature. 1992 Apr. 30; 356 (6372):768-74) and Nicholson et al., (Nicholson D W, Ali A, Thornberry N A, Vaillancourt J P, Ding C K, Gallant M, Gareau Y, Griffin P R, Labelle M, Lazebnik Y A, et al. Identification and inhibition of the ICE/CED-3 protease necessary for mammalian apoptosis. Nature. 1995 Jul. 6; 376(6535):37-43)).

Synthesis of Tri/Tetra Peptide and Derivatives Thereof (Chemical Modification) for Use as Agents In the most common strategy of solid phase peptide synthesis, as described by Merrifield (37), an amino acid with both α-amino group and side chain protection is immobilized to a resin. The α-amino-protecting group is usually an acid-sensitive tert-butoxycarbonyl (Boc) group or a base-sensitive 9-fluorenylmethyloxycarbonyl (Fmoc) group. These α-amino-protecting groups can be efficiently removed, and a protected amino acid with an activated carboxyl group can then be coupled to the unprotected resin-bound amine. The coupling reactions are forced to completion by using an excess of activated soluble amino acid. The cycle of deprotection and coupling is repeated to complete the sequence. With side chain deprotection and cleavage, the resin yields the desired peptide (36, 37).

For chloromethyl ketone (CMK)-modified peptides, the CMK chemical group located at the C-terminus of the peptide will occupy the active site but will form a covalent bond resulting in irreversible inhibition of the protease. More specifically, CMK are transition-state irreversible inhibitors. The active site Ser 195 of the enzyme forms a tetrahedral adduct with the carbonyl group of the inhibitor, and the active site histidine is alkylated by the CMK functional group (See REF:35)

Results

Truncated IL-36 Proteins Exhibit Biological Activity

Figure 1:
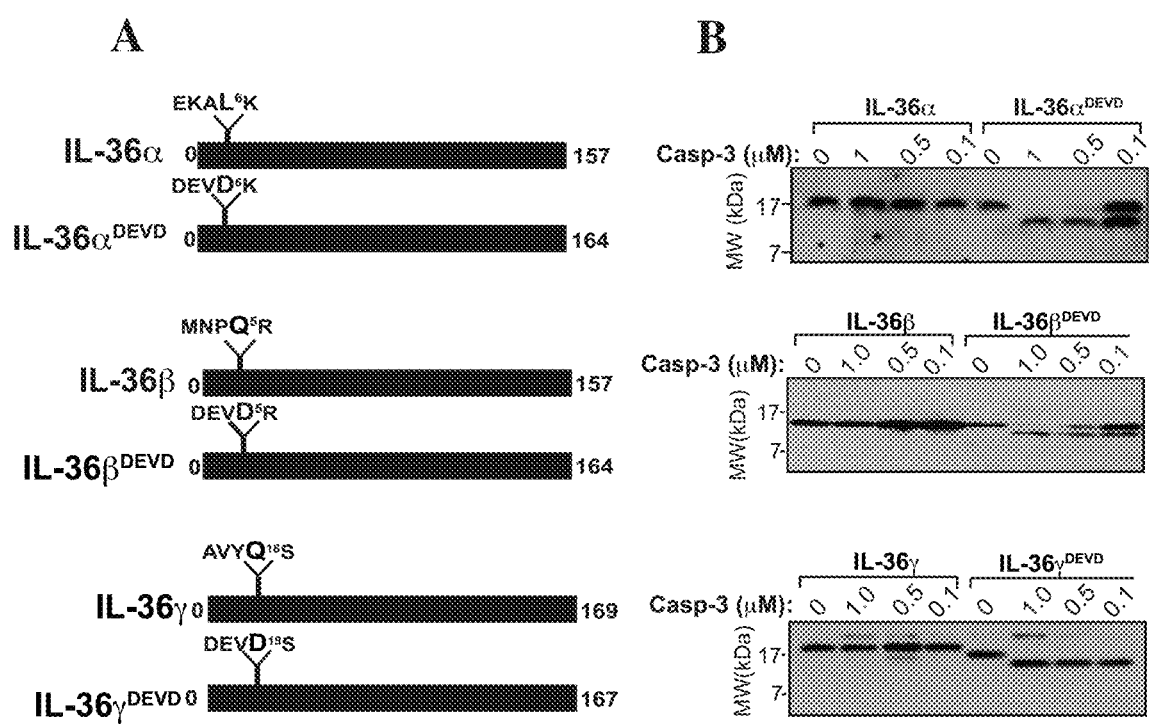
Figure 2:
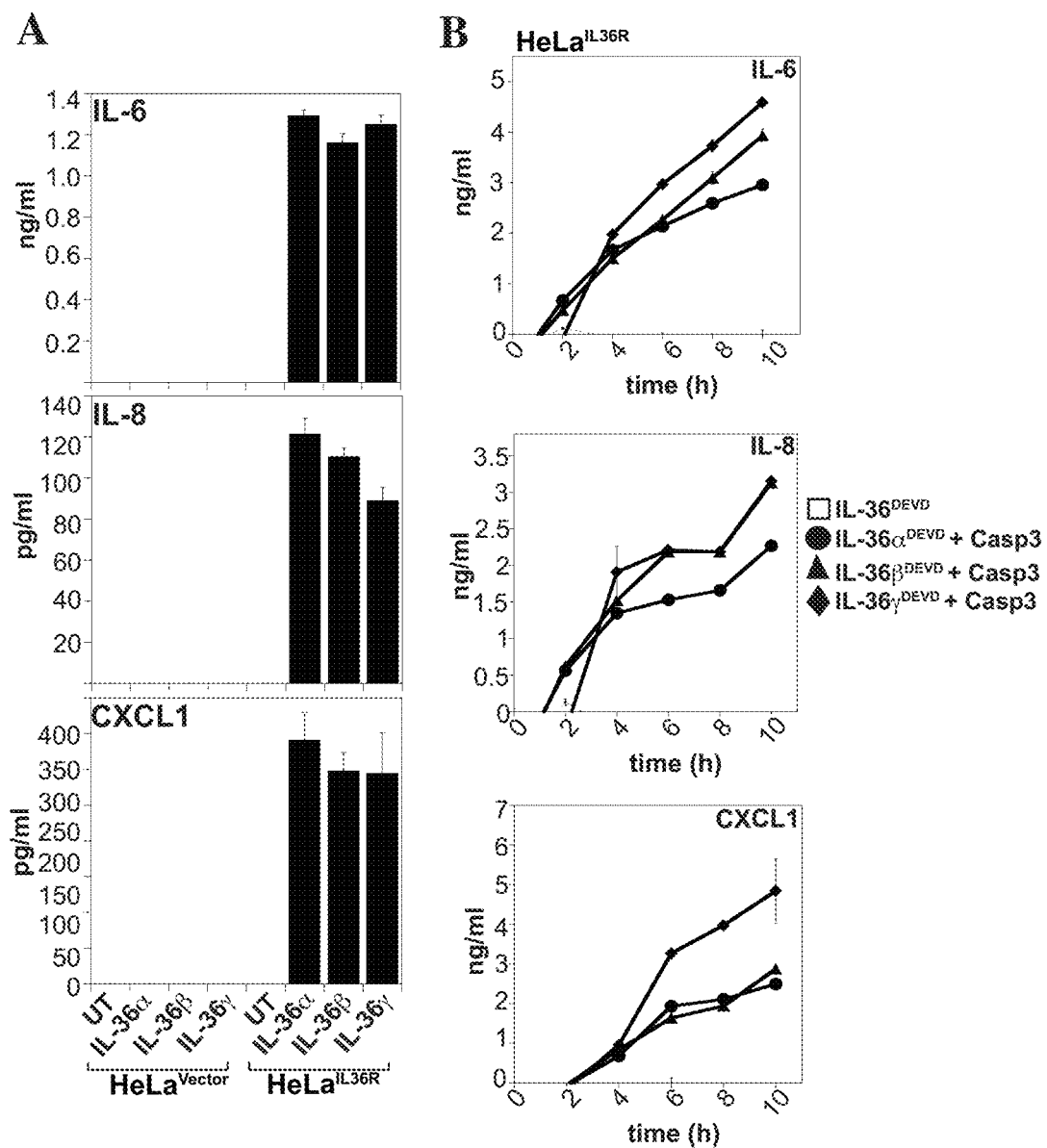
Figure 3:
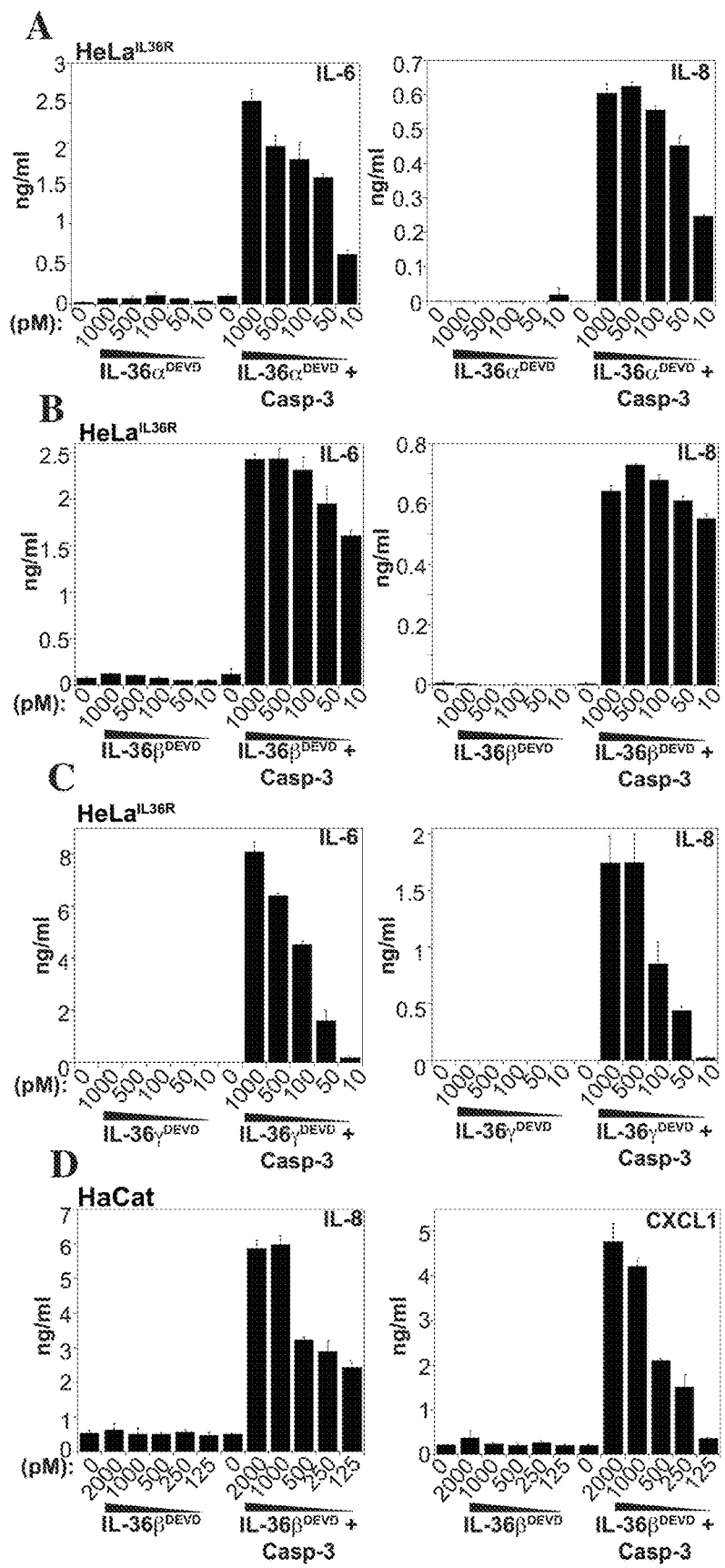

To identify the proteases responsible for processing and activation of IL-36 cytokines, we established an IL-36 bioassay by stably transfecting HeLa cells with the human IL-36 receptor (IL-1Rrp2). Sims and colleagues have reported that artificial truncation of IL-36α, β and γ at particular N-terminal residues dramatically increases the activity of these proteins[24] (FIG. 1a). To confirm that HeLa$^{IL-36R}$ cells were IL-36-responsive, we created modified forms of IL-36α, β and γ by inserting a caspase-3 cleavage motif, DEVD, proximal to the residues identified by Towne et al. to lead to IL-36-dependent NFkB activation when exposed at the N-termini of IL-36 cytokines (FIG. 1a). As FIG. 1b illustrates, DEVD-modified IL-36β (IL-36β$^{DEVD}$) and DEVD-modified IL-36γ (IL-36γ$^{DEVD}$) was readily processed by caspase-3 whereas IL-36b$^{wt}$ and IL-36g$^{wt}$ were not. HeLawi cells failed to respond to either full length or caspase-3-cleaved IL-36β$^{DEVD}$, while HeLa$^{IL-36R}$ cells secreted multiple cytokines in response to caspase-3-processed IL-36β$^{DEVD}$, but not full length unprocessed IL-36β$^{DEVD}$ (FIG. 2a, b, FIG. 3). Similar data were obtained for a DEVD-modified form of IL-36α (FIG. 3a, b). Furthermore, the transformed skin line HaCat, which naturally express IL-1Rrp2, also responded to the caspase-3-cleaved IL-36$^{DEVD}$ forms. (FIG. 3d). These data confirmed that proteolytic processing of IL-36α, β and γ dramatically increase the biological activity of these cytokines and established a bioassay to screen for proteases that naturally process and activate IL-36 cytokines.

Neutrophil-Derived Proteases Activate IL-36 Cytokines

Figure 4:
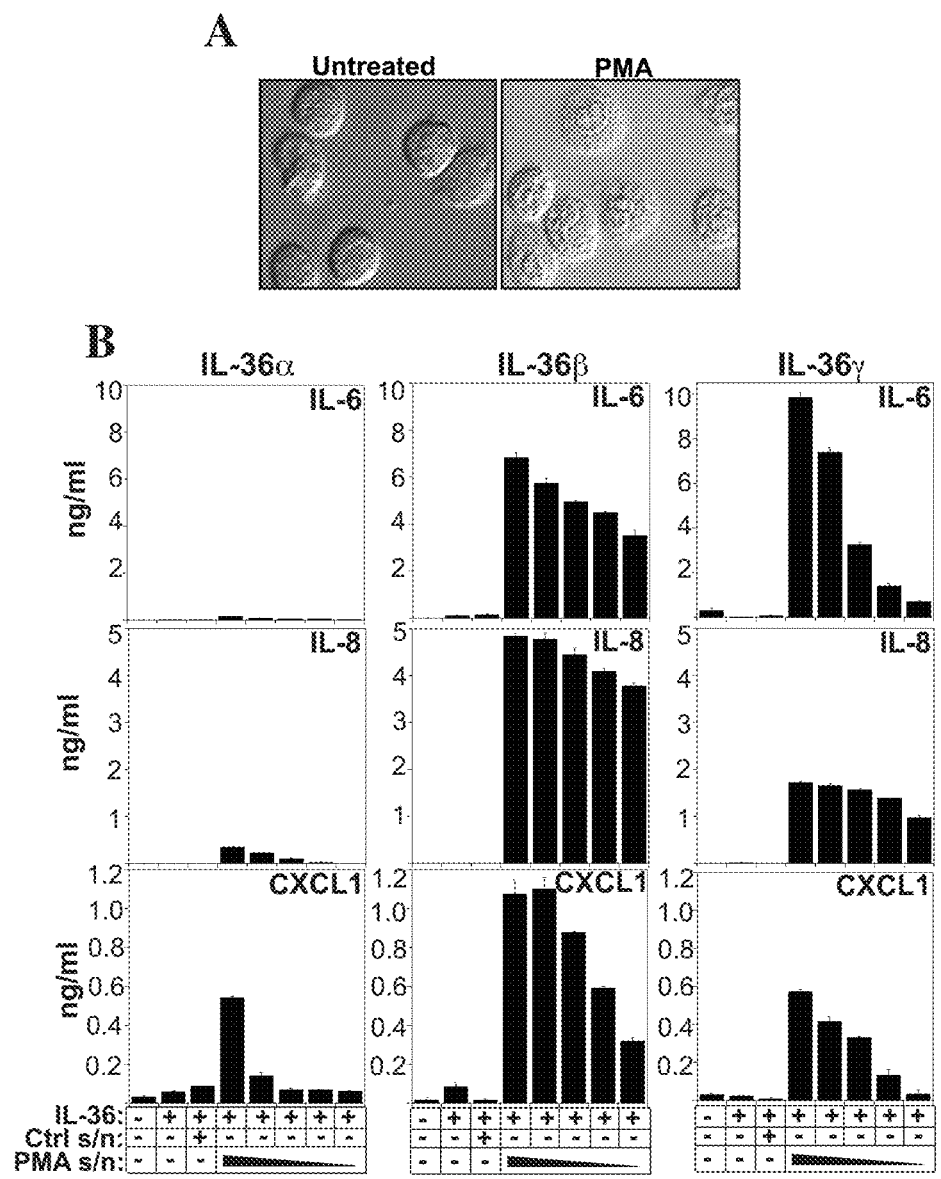

One of the hallmarks of psoriatic lesions is persistent infiltration of the epidermis by neutrophils[23,25]. Neutrophil granule proteases contain three major seine proteases (elastase, cathepsin G and proteinase-3) that are involved in bacterial killing as well as in the processing of certain cytokines and chemokines[27]. Indeed, previous studies have found that neutrophil elastase can process and activate IL-1α[28] and that cathepsin G and elastase can activate IL-33[29]. To explore whether neutrophil-derived proteases can process and activate IL-36 cytokines, we induced human peripheral blood neutrophils to degranulate with PMA, thereby liberating granule proteases and generating reactive oxygen species (ROS)[30-31] (FIG. 4a, b). Robust ROS production and protease activity was found in supernatants from PMA-treated neutrophils, as expected (FIG. 4b). Purified full-length IL-36a, b and g were then incubated with supernatants from untreated versus PMA-treated neutrophils, followed by assessment of IL-36 activity using HeLa$^{IL-36R}$ cells. As shown in FIG. 4c, incubation of IL-36 cytokines in the presence of PMA-activated neutrophil 20 degranulates resulted in robust activation of IL-36β and IL-36γ, whereas IL-36α was poorly activated under the same conditions.

Identification of IL-36-Activating Proteases

Figure 5:
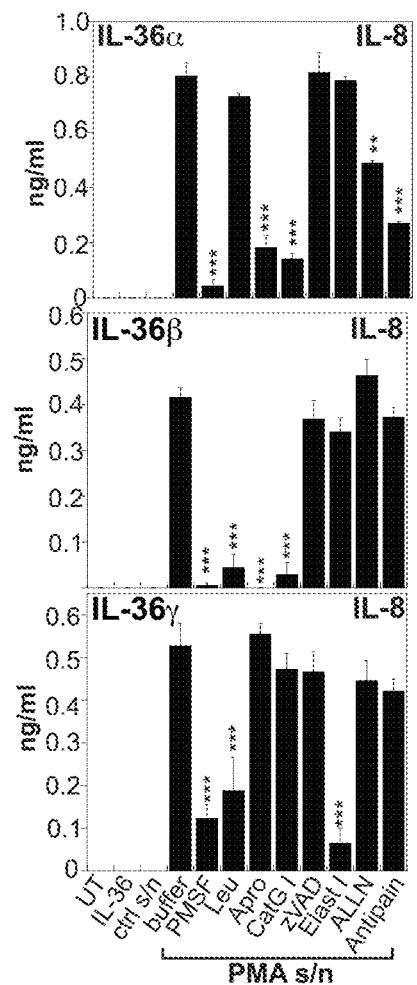
Figure 6:
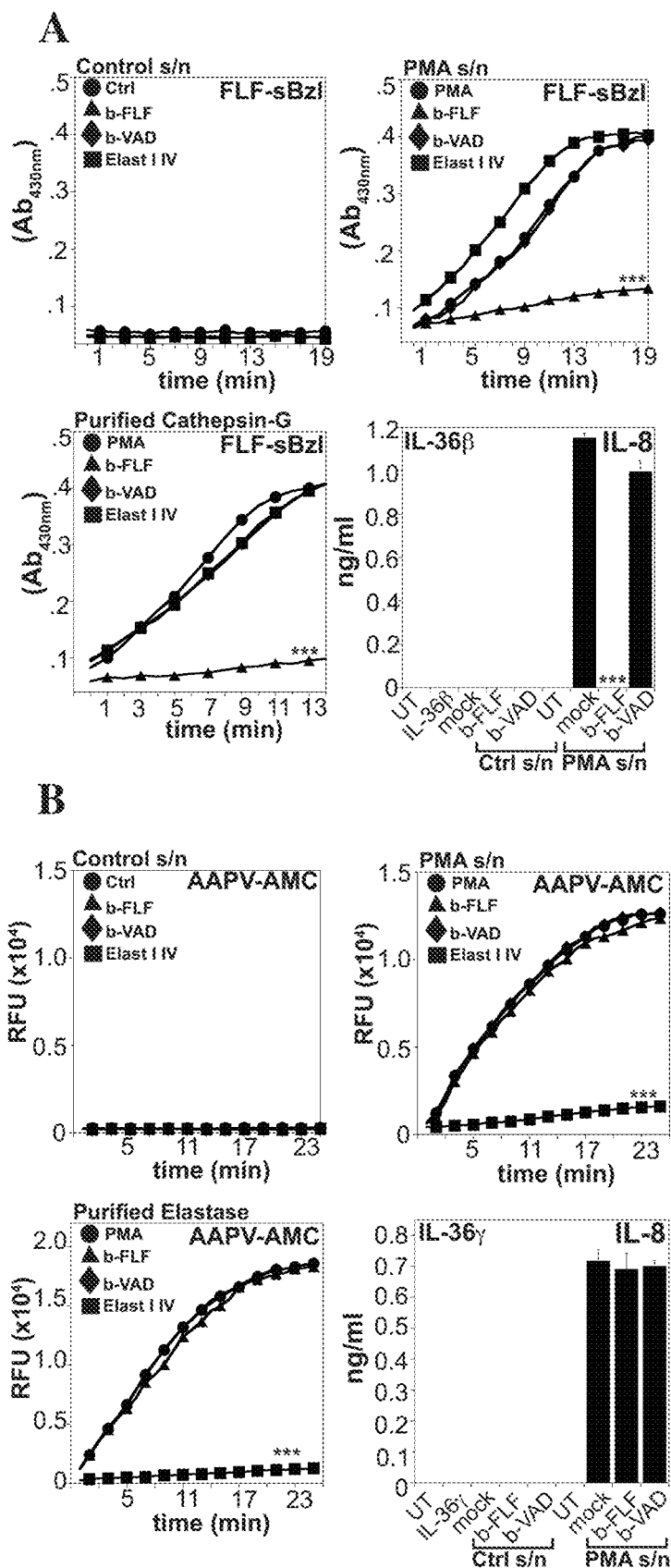
Figure 7:
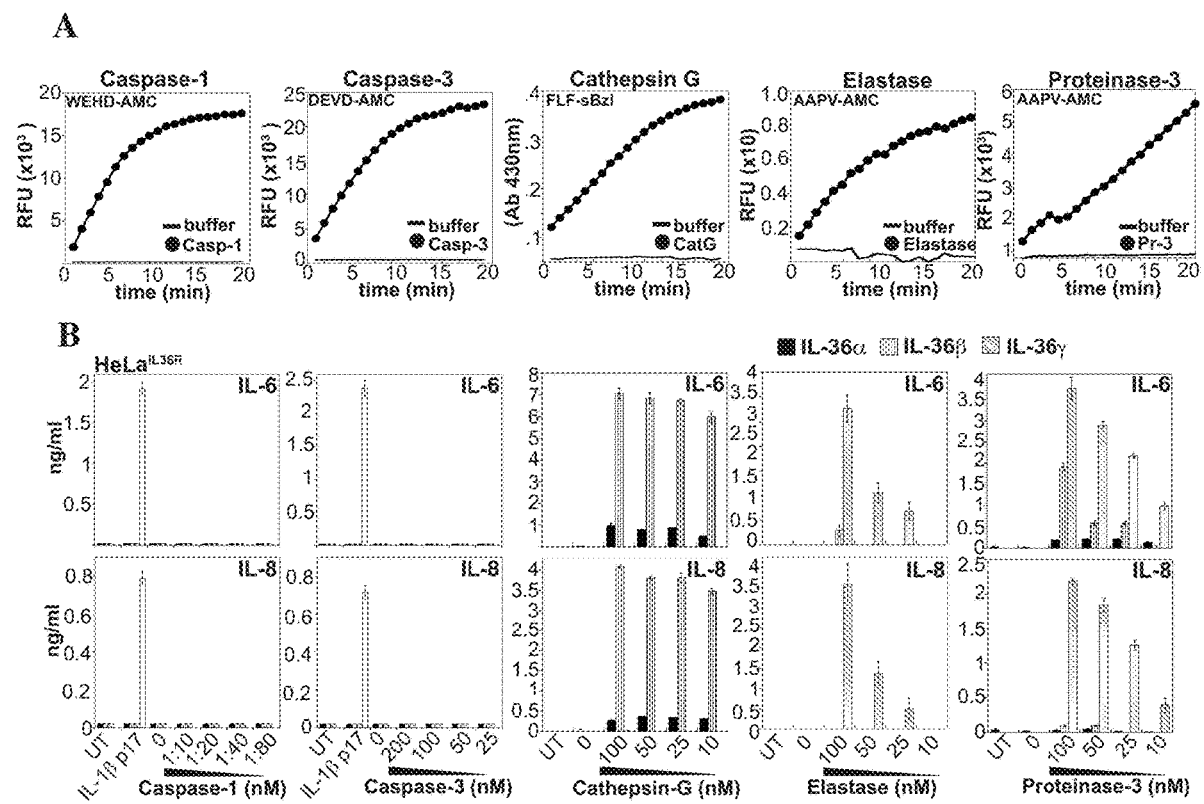

To identify the specific protease(s) involved in IL-36β and γ activation, we initially used a panel of broad-spectrum protease inhibitors. As FIG. 5 illustrate, the serine protease inhibitor PMSF, as well a specific chemical inhibitor of cathepsin G robustly inhibited the activation of IL-36α and IL-36β while a specific chemical inhibitor of elastase inhibited the activation of IL-36γ by activated neutrophil degranulates. To explore the identity of the IL-36 processing protease(s) further, we designed a panel of peptides based upon optimal cathepsin G cleavage motifs. These peptides were then assessed for their ability to inhibit activation of IL-36 cytokines by PMA-activated neutrophil degranulates. As FIG. 6, FIG. 29, FIG. 30 demonstrate, the cathepsin G-inhibitory peptides, FLF-CMK, AFLF-CMK and EPF-CMK, proved to be the most potent inhibitors of IL-36β activation by neutrophil degranulates. In contrast, IL-36γ activation was antagonized by a specific chemical inhibitor of elastase (FIG. 6). We also generated a biotin-conjugated form of the cathepsin G inhibitor, biotin-FLF-CMK, to ask whether this depleted the IL-36b activating activity from neutrophil degranulates. As FIG. 6a illustrates, selective depletion of cathepsin G activity from PMA-treated neutrophil degranulates using biotin-FLF-CMK largely eliminated activation of IL-36b but not of IL-36g (FIG. 6b).

Purified Cathepsin G and Elastase Activate IL-36 Cytokines

Figure 8:
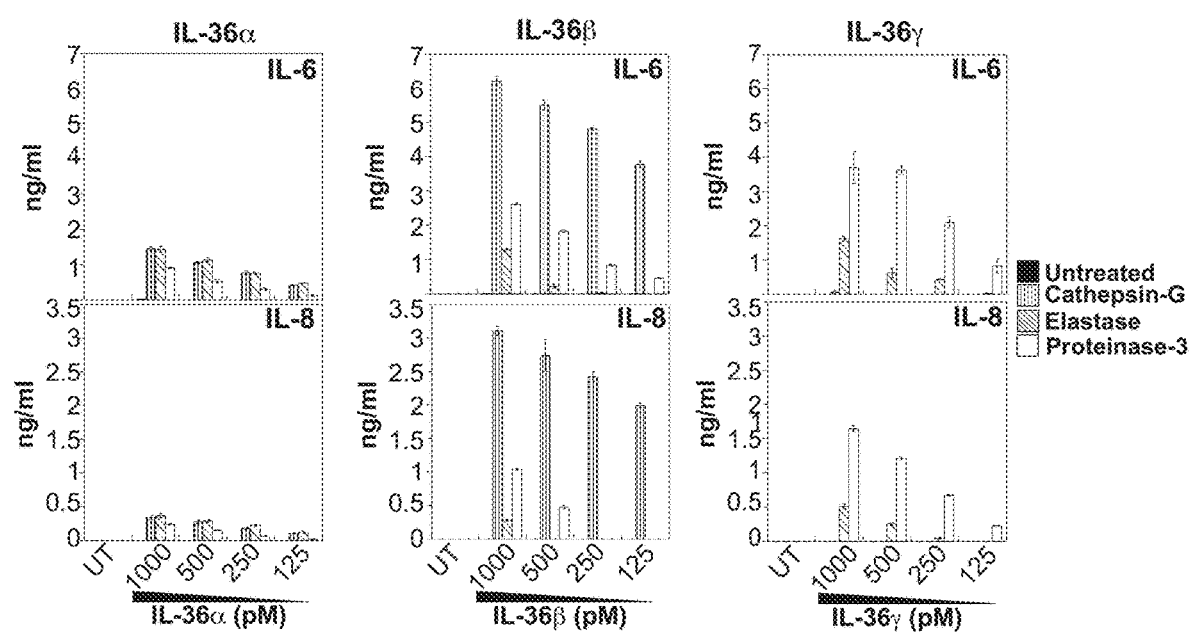

We next compared the ability of purified cathepsin G, elastase and proteinase-3 to process and activate IL-36 cytokines. The activity of all purified proteases employed was confirmed using synthetic substrate peptides (FIG. 7a). As FIG. 7b demonstrates, cathepsin G selectively promoted IL-36β activation, whereas elastase and proteinase-3 preferentially activated IL-36γ. Furthermore, IL-36α is activated by cathepsin-G and proteinase-3 (FIG. 7b). Because caspase-1 processes and activates the IL-1 family cytokines, IL-1β and IL-18, we also explored whether caspase-1 or caspase-3 could process and activate IL-36 family cytokines. However, as FIG. 7b illustrates, neither caspase activated any of the IL-36 cytokines. To exclude the possibility that the concentrations of IL-36α we used in the above experiments were too low to detect biological activity, we also titrated IL-36 cytokines over a wide concentration range in the presence and absence of cathepsin G, elastase or proteinase-3. As FIG. 8 shows, once again cathepsin G was found to preferentially activate IL-36β and to some extent proteinase-3 while elastase and proteinase-3 preferentially activate IL-36γ. Cathepsin G also exhibiting modest activation of IL-36γ at higher molar concentrations. Finally, all three neutrophils proteases activate IL-36α at higher molar concentrations (FIG. 8).

Mapping of Cathepsin G and Elastase Cleavage Sites in IL-36 Cytokines

Figure 9:
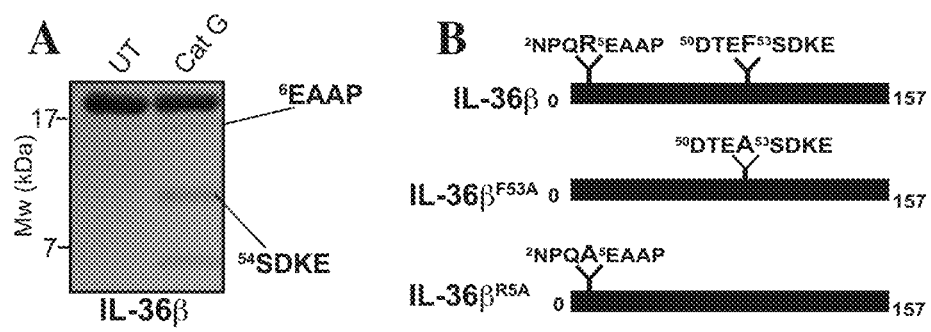
Figure 10:
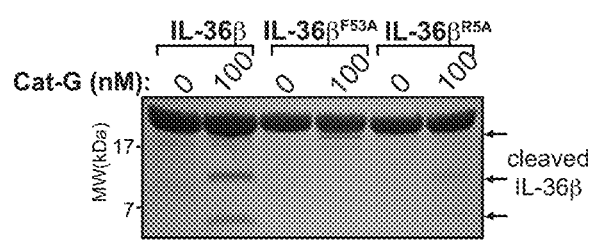
Figure 11:
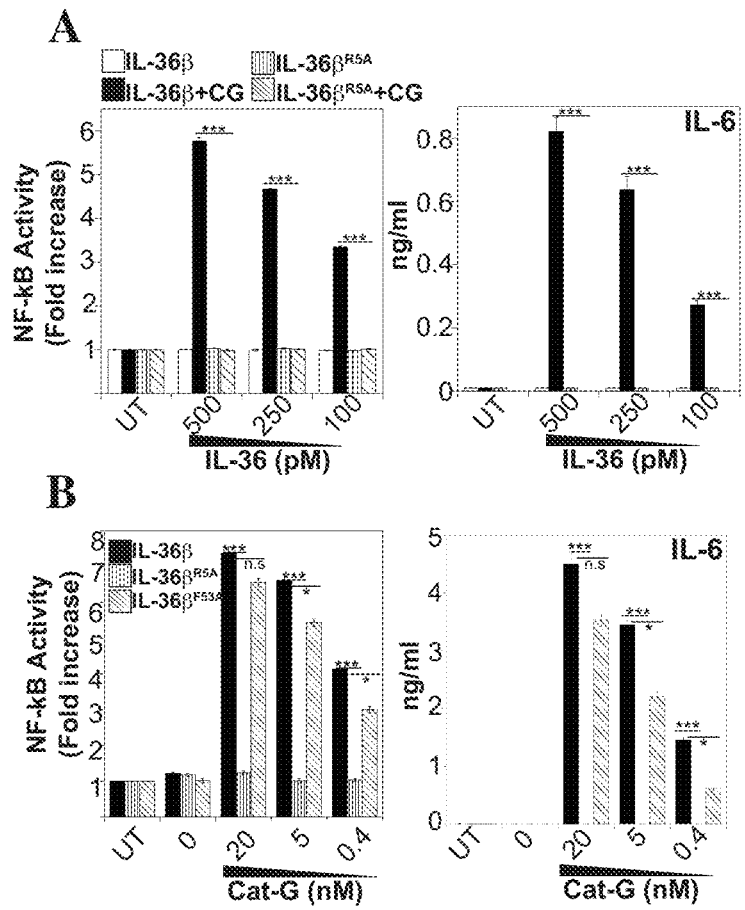
Figure 12:
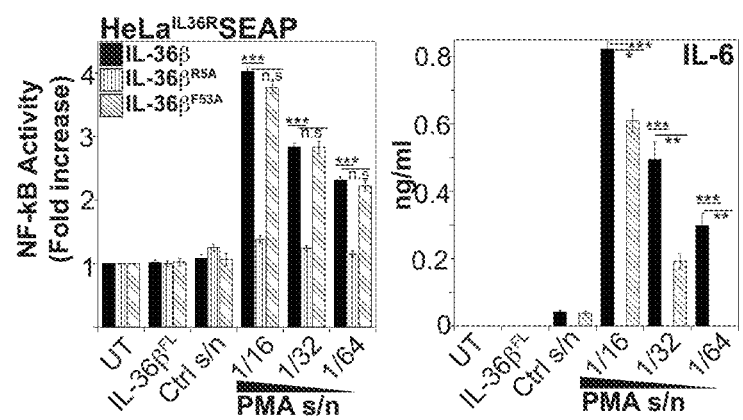
FIG. 12 are graphs showing HeLa$^{IL36R}$ stimulated with 500 pM of IL36β, IL-36β$^{R5A}$ and IL36β$^{F53A}$ pre-incubated for 2 h at 37° with a titration of PMA-activated neutrophil degranulate. After 24 hr, NF-kB activity was measured as a fold induction of SEAP in the supernatant and cytokine concentrations in culture supernatants were determined by ELISA.
Figure 13:
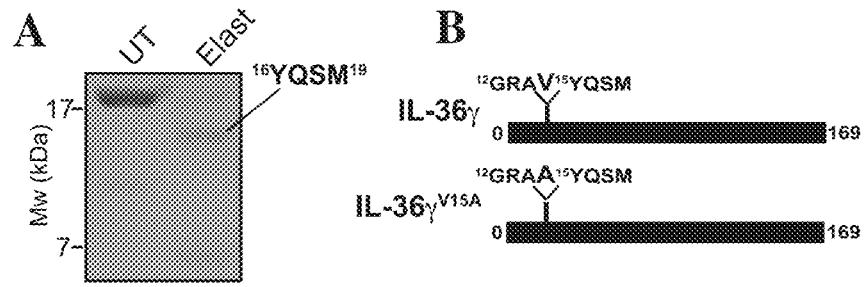
FIG. 13 (A) is a Coomassie blue stained gel of recombinant IL-36γ that was incubated in the presence or absence of Elastase (100 nM). Indicated fragment was analysed by Edman Degradation sequencing and novel N-terminus was identified as ($^{16}$YQSM). (B) is schematics representing GRAV$^{15}$ cleavage motif within IL-36γ and the point mutant IL-36γ V15A.
Figure 14:
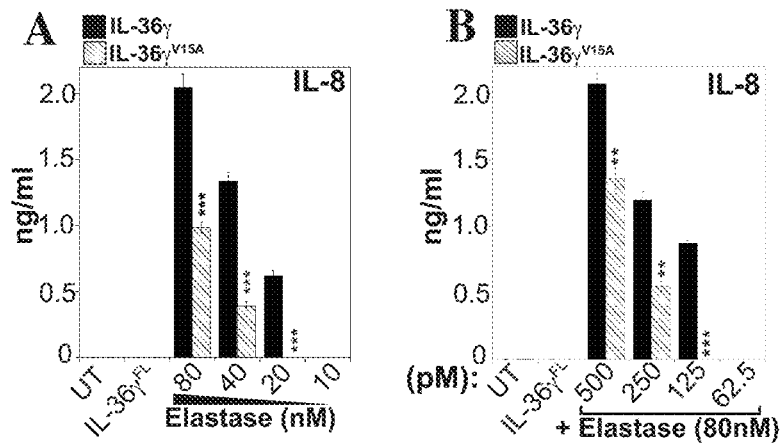
FIG. 14 (A) is a graph showing recombinant IL-36γ and IL-36γ$^{V15A}$ incubated with a titration of Elastase or (B) fixed dose of Elastase (80 nM). After 24 hr, cytokine concentrations in culture supernatants were determined by ELISA.
Figure 15:
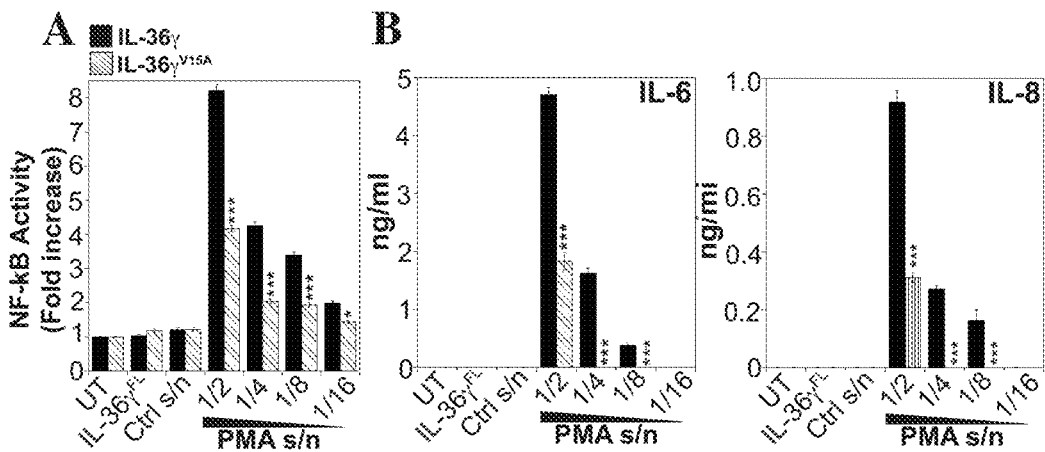
FIG. 15 are graphs showing recombinant IL-36γ and IL-36γ$^{V15A}$ incubated with a titration of PMA-activated neutrophil degranulate. After 24 hr, (A) NF-κB activity was measured as a fold induction of SEAP in the supernatant and (B) cytokine concentrations in culture supernatants were determined by ELISA.

To identify the cathepsin G cleavage site(s) within IL-36β that result in activation, we performed N-terminal sequencing of cathepsin G-treated IL-36β preparations. This analysis identified two candidate sites at Arg5 and Phe53 (FIG. 9). Thus, we generated mutations at both of these sites to assess their role in cathepsin G-mediated activation of IL-36β. We initially tested each mutant for resistance to proteolysis by cathepsin G. As FIG. 10 shows, IL-36β$^{F53A}$ suppresses appearance of the two major cleavage bands (~10 and ~4 kDa), yet still generates a third cleavage band (~17 kDa) just below the full-length protein. In contrast, IL-36β$^{R5A}$ largely attenuates the appearance of the ~17 kDa band just below the full-length band while the appearance of the cleavage bands (~10 and ~4 kDa) are significantly diminished. As FIG. 11, FIG. 12 illustrate, whereas mutation of Phe53 had no effect on cathepsin G-mediated IL-36β activation, mutation of Arg5 dramatically abolished activation of this cytokine. Furthermore, mutation of Arg5 also abolished activation of IL-36β by PMA-activated neutrophil degranulates (FIG. 11, FIG. 12). Using a similar approach, we identified Val15 in IL-36γ as the residue cleaved by elastase to promote activation of the latter (FIG. 13). Mutation of this residue also significantly attenuated activation of the latter by elastase, as well as by PMA-activated neutrophil degranulates (FIG. 14, FIG. 15).

Activated IL-36 Promotes Robust Cytokine Production by Keratinocytes

Figure 16:
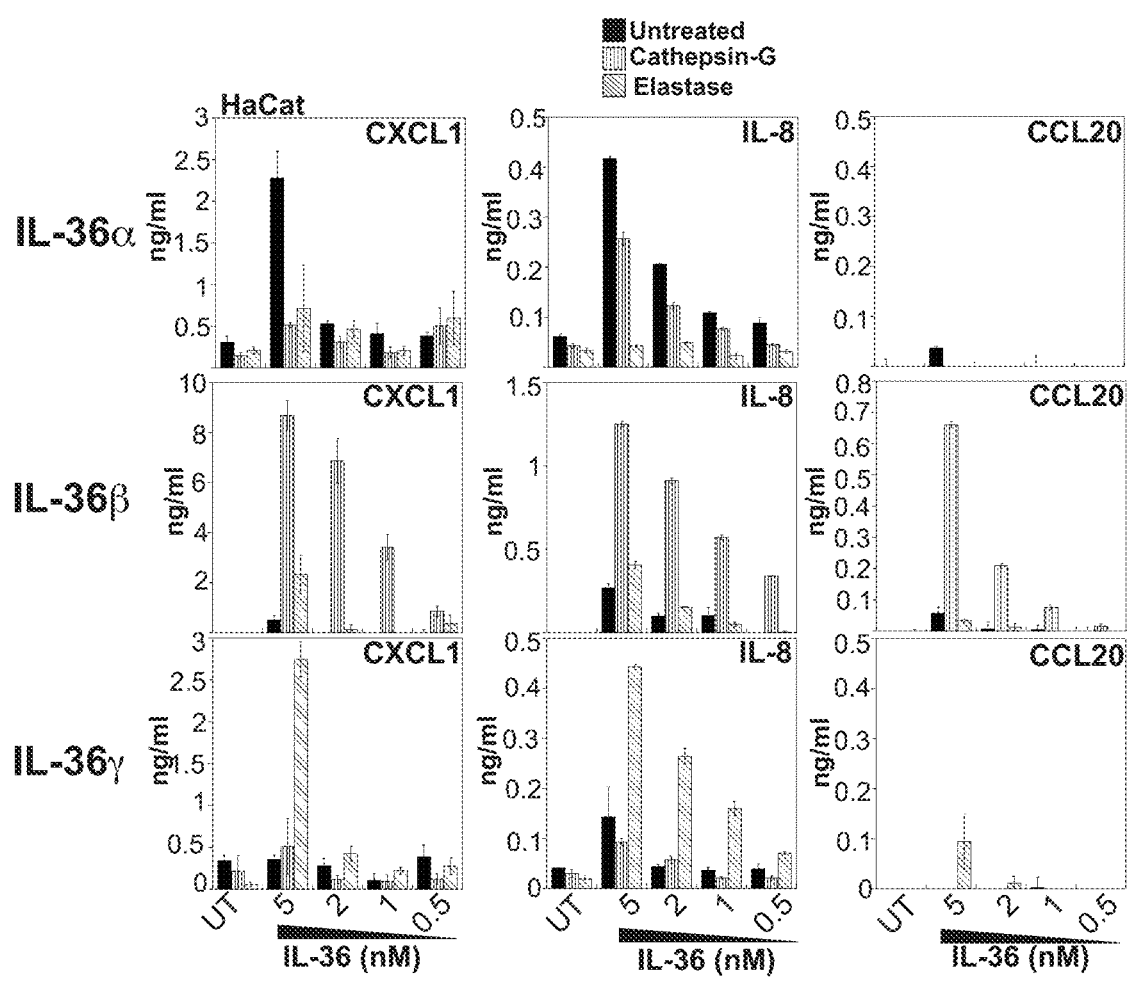
FIG. 16 are graphs showing HaCat stimulated with indicated titration of IL36α, β and γ pre-incubated for 2 h at 37° with cathepsin-G (50 nM), elastase (100 nM). After 24 h, cytokine concentrations in culture supernatants were determined by ELISA.
Figure 17:
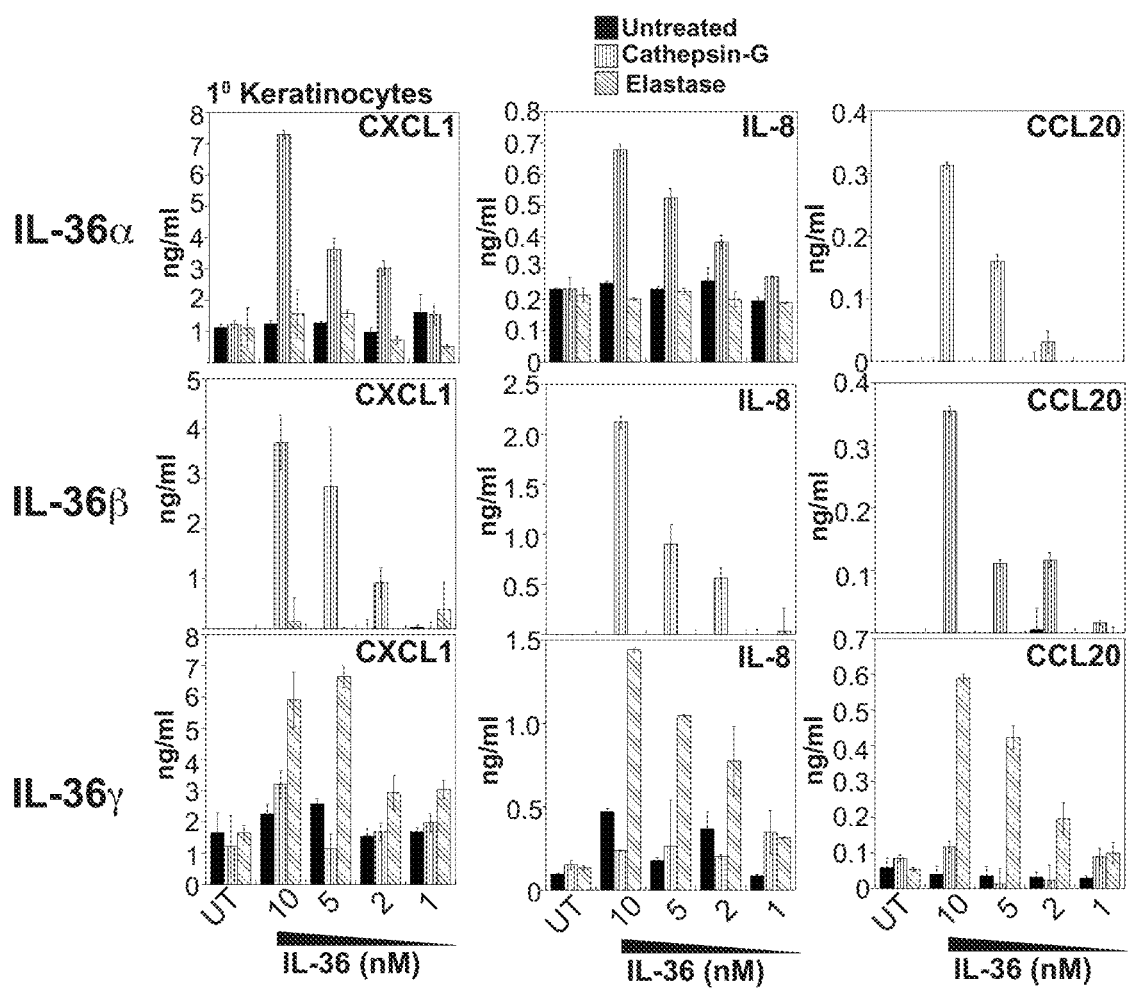
FIG. 17 are graphs showing primary keratinocytes stimulated with indicated titration of IL36α, β and γ pre-incubated for 2 h at 37° with cathepsin-G (50 nM), elastase (100 nM). After 24 h, cytokine concentrations in culture supernatants were determined by ELISA.

To explore the biological activity of IL-36β in a physiologically relevant cell type, we used transformed HaCat keratinocytes as well as primary human epidermal keratinocytes to ask whether cathepsin G-processed IL-36β or elastase-processed IL-36γ were capable of triggering the production of pro-inflammatory cytokines from these cells. As illustrated in FIG. 16, whereas full length IL-36β or IL-36γ exhibited little activity on HaCaT cells, cathepsin G-treated IL-36β and elastase-processed IL-36γ induced robust production of chemokines from these cells. Essentially identical results were seen with primary human keratinocytes (FIG. 17). Furthermore, using a reconstituted human 3D skin model, we also found that cathepsin G-processed IL-36θ was sufficient to perturb skin differentiation to produce features resembling psoriasis, such as acanthosis and marked hyperkeratosis of the cornfield layer (FIG. 18).

IL-36b is Sufficient to Drive IL-17 Production in Keratinocytes

To explore the biological effects of IL-36 further, we conducted gene expression array analyses in primary keratinocytes. As FIG. 19 demonstrates, cathepsin G-activated IL-36β induced robust expression of a diverse array of pro-inflammatory cytokines and chemokines from these cells. Of particular note, IL-36 induced strong transcriptional upregulation of IL-17C (~50-fold within 8 hours), a cytokine that has been implicated as a key driver of the pathology observed in psoriasis and other conditions. IL-36β also induced robust expression of multiple additional inflammatory factors, such as complement C3, b-defensin-2, S100A9, TNFα, and G-CSF which are frequently elevated in lesional skin from psoriatic patients[19] (FIG. 19). Interestingly, we also found that IL-36γ induced a strong signature of IL-36γ upregulation in primary keratinocytes, suggesting that this cytokine can promote a positive feedback loop for IL-36 cytokine expression. We validated IL-36-induced expression of several of these cytokines at the mRNA level (FIG. 20), as well as by ELISA, including IL-8, CXCL1 and IL-17C (FIG. 21a, b). Furthermore, IL-17C can itself promote cytokine production from primary keratinocytes (FIG. 21c).

Endogenous IL-36 Cytokines are Induced by Poly:(IC) as Well as IL-36

To explore the expression of endogenous IL-36 cytokines in keratinocytes, we generated polyclonal antibodies against all three IL-36 cytokines (FIG. 22). Whereas little endogenous IL-36α or β could be detected constitutively, IL-36γ was detected in primary keratinocytes (FIG. 22a). However, treatment of these cells with IL-36, PMA or the Toll-3 agonist poly:(IC) robustly induced the expression of endogenous IL-36γ (FIG. 23a, b). HaCat were also found to upregulate IL-36γ after IL-36 and PMA treatment (FIG. 24a, b). Primary human keratinocytes are reported to express the full-length forms of pro-IL-1α and pro-IL-1β at the protein level[25]. Indeed, we detected both, pro-IL-1α and pro-IL-1β constitutively expressed in primary keratinocytes (FIG. 22a, b). Furthermore, these cytokines were upregulated further in response to IL-36 and Poly:(IC) (FIG. 22a, b). Similar observations were made with HaCat cells (24 a, b).

Endogenous IL-36γ is Cleaved by Neutrophil Proteases

Consistent with previous data on other IL-1 family members IL-1β and IL-18, we failed to detect IL-36-dependent activity in the supernatants of SLO-lysed keratinocytes containing full-length IL-36γ (FIG. 7a, b). Of particular note, we also observed release of the full-length forms of IL-1α and IL-1β along with release of irrelevant proteins Cullin-3 and Actin into the cell supernatants, indicative of the non-selective nature of necrotic cell death (FIG. 7a). Furthermore, supernatants from SLO-lysed keratinocytes cells displayed activity that was IL-36-independent, but was dependent on IL-1α (FIG. 25a, b). To explore if IL-36γ, both intracellularly and extracellularly is subject to cleavage by neutrophil elastase, we generated cell extracts and supernatants followed by incubation with neutrophil proteases. As FIG. 26 a, b, illustrates, IL-36γ incubated with elastase resulted in robust IL-36γ proteolysis both intracellularly as well as extracellularly, with the resulting cleavage fragments running at a similar mobility to that produced through proteolysis of recombinant IL-36γ by elastase. Collectively these data indicate a role for IL-36 cytokines as targets of neutrophil serine proteases.

IL-36γ is Greatly Elevated within Lesional Skin from Psoriatic Individuals

To explore whether IL-36 ligands was elevated in lesional skin from psoriatic individuals, we generated homogenates from skin samples obtained from uninvolved as well as involved areas from psoriatic individuals. As FIG. 27a shows, these experiments revealed that IL-36g was greatly elevated in psoriatic tissue, while IL-36α and IL-36β were undetectable in these patient samples. Furthermore, incubating these psoriatic homogenates with neutrophil elastase resulted in IL-36γ proteolysis, with the resulting cleavage fragments running at a similar mobility to that produced through proteolysis of recombinant IL-36γ (FIG. 27b).

Psoriatic Lesional Skin Displays a Predominantly Cathepsin-G Like Activity that Activates IL-36 Cytokines To explore the role of neutrophil proteases in a disease relevant setting, we generated control skin and psoriatic skin samples via the tape-strip method. As FIG. 40a, b show, these experiments revealed that psoriatic skin eluates contains a significantly elevated cathepsin-G like protease activity as demonstrated by robust FLF-sBzl hydrolysis, while Elastase-like activity was not elevated in psoriatic skin measured using the AAPV-AMC peptide. Next, we incubated these control and psoriatic skin eluates with equal molar concentrations of IL-36 cytokines. As FIG. 40c demonstrates, IL-36β was robustly activated by psoriatic skin eluates, with IL-36α activated but to much less efficient degree. Control skin eluates failed to activate IL-36 cytokines. Consistent with the cathepsin-G-like enzymatic activity, a specific cathepsin-G inhibitor attenuated IL-36β and IL-36α activation by the psoriatic skin eluates, while an elastase inhibitor failed to attenuate IL-36 activation. These data, are consistent with a cathepsin-G like enzymatic activity in psoriatic skin that is capable of activating IL-36β.

CONCLUSION

Our findings show that IL-36 cytokines are activated by neutrophil granule proteases. In particular, IL-36β and IL36γ are processed by cathepsin G, elastase and proteinase-3, respectively and proteolysis of these cytokines releases their full biological potency. Previous reports by Sims and colleagues[24] suggested that IL-36 cytokines have limited biological activity as full-length proteins, and require processing at their N-termini to activate them. However, the latter authors did not identify the proteases that naturally process and activate these cytokines, but mapped their active forms using artificial truncations. We have also found that IL-36 cytokines have very limited biological activity as full-length proteins, however proteolysis by cathepsin G, elastase and proteinase-3 greatly enhanced the biological activity of IL-36β and IL-36γ respectively.

Proteolysis of IL-36 cytokines may induce a profound conformational change in these proteins that increase their affinity for the IL-36 receptor (IL-1 Rrp2), thereby increasing biological potency. Alternatively, the IL-36 N-termini may partly occlude the receptor binding domain, removal of which permits a more stable interaction with the IL-36R complex. Previously, Hazuda and colleagues have reported that pro-IL-1α and pro-IL-1β cytokines undergo profound conformational changes upon removal of their N-termini and, as a consequence, the mature regions of these molecules switch from a proteinase K-sensitive to a proteinase K-insensitive state. This change is most likely reflected in an altered conformation that increase their affinity for the IL-1 receptor[26].

Immune cell infiltration is a hallmark of a number of skin-related inflammatory diseases. In particular, psoriatic plaques are heavily infiltrated with neutrophils, dendritic cells, macrophages, and T-cells[26]. Neutrophils are critical first responder cells in our innate immune system and play a critical role in the initial response to infection or tissue damage. Neutrophils perform a range of functions in their role in immune defence and inflammation which includes: engulfment and destruction of microbes via ROS production, release of neutrophil extracellular traps to sequester and kill microbes, release of cytokines to orchestrate immune responses, as well as the production of a vast repertoire of antimicrobial molecules such as defensins, and granule proteases such as elastase and cathepsin G[27]. Furthermore, mice doubly deficient in the neutrophil granule proteases cathepsin G and elastase have deficiencies in bacterial clearance as well as increased mortality to *streptococcus, pseudomonas*, and mycobacterial infections[28-29]. While the degranulation and release of neutrophil proteases exert profound antimicrobial and protective effects during infection, in excess they can cause extensive tissue damage through ROS production, inflammatory cytokine activation, as described herein, and protease degradation of the extracellular matrix[31]. Excessive neutrophil protease activity is typically prevented by serum anti-proteases such as α-1-antitrypsin and 2-macroglobulin that are also typically synthesized during inflammatory responses[27].

Interestingly, the onset of psoriasis symptoms in affected individuals often follows a streptococcal A infection, which is likely to be associated with both necrosis of infected, as well as surrounding tissue and with robust neutrophil and macrophage infiltration. If necrosis is not a direct consequence of pathogen activities, necrosis of barrier tissues as a result of compression injuries or burns, for example, is likely to lead to infection. Thus, the immune system recognizes this as potential danger and mounts an innate immune response characterized by the infiltration immune cells such as neutrophils and macrophages into the site of injury[9,30]. Curiously, clinicians have observed that the development of psoriatic lesions can develop as a result of the epidermis experiencing physical injuries such as lacerations, burns or after surgical incisions. This trauma-induced psoriasis is often described as the 'Koebner phenomenon', which was first described in 1877[35]. An important feature that unites all of the above diverse scenarios is that all are capable of triggering necrotic cell death in the epidermis. As a direct consequence of necrosis, non-classical cytokines such as IL-36, IL-33 and IL-1α are released into the extracellular space where they can act on local epithelia to drive further inflammation. Necrosis can also lead to robust activation and infiltration of the injured site by cells of the immune systems such as neutrophils, macrophages and mast cells. It is under these conditions that extracellular IL-36 ligands may encounter and become processed by neutrophil serine proteases as these proteases are frequently found at elevated levels within psoriatic lesions. Indeed, our results show that activated IL-36 is capable of driving a robust inflammatory response in primary keratinocytes, including the induction of IL-1α, TNFα, IL-17C, G-CSF, IL-8, S100 proteins, as well as IL-36 itself. Keratinocytes make up the majority of cells within the epidermis, which constitutes a very important barrier against infection. In addition to serving as a physical barrier against the entry of microorganisms, it is now well appreciated that keratinocytes are capable of directly responding to damage or infection by releasing a number of key cytokines, such as IL-1α, IL-1β and IL-36 cytokines to activate local macrophages and dendritic cells to initiate immune responses[5]. In this respect keratinocytes serve as key sentinel cells that alert the immune system to potential danger. Moreover, our results show that IL-36γ as well as IL-1α/β, are endogenously expressed by keratinocytes and subject to modulation by either IL-36 signalling or Toll-receptor engagement. Therefore, keratinocytes are posed to release cytokines such as IL-36γ and IL-1α upon tissue injury. Thus, damage to keratinocytes, either as a result of microbial infection or through tissue trauma, is likely to play an important initiating role in psoriasis, especially in individuals carrying genetic predispositions to this disease (such as deficiency in the IL-36R antagonist). This leads to the triggering of an inflammatory reaction, of which IL-36 cytokines play a critical role, leading to further amplification of damage in a self-sustaining inflammatory loop.

In summary, we have shown that IL-36 cytokines are robustly activated by the neutrophil proteases, cathepsin G, elastase and proteinase-3, as well as cathepsin K, and that this proteolysis increases their biological activity ~500-fold. Collectively these results show an important role for neutrophil proteases as potent activators of IL-36 cytokines and suggest that targeted inhibition of these proteases, as described here, may have therapeutic benefits in inflammatory skin conditions such as psoriasis and other similar conditions.

The invention is not limited to the embodiment(s) described herein but can be amended or modified without departing from the scope of the present invention.

REFERENCES

1. Marrakchi, S., Guigue, P., Renshaw, B. R., Puel, A., Pei, X. Y., Fraitag, S., Zribi, J., Bal, E., Cluzeau, C., Chrabieh, M., Towne, J. E., et al. Interleukin-36-receptor antagonist deficiency and generalized pustular psoriasis. N. Engl. J. Med. 365, 620-8 (2011)
2. Jesus, A. A., Goldbach-Mansky, R. IL-1 Blockade in Autoinflammtory syndromes Annu. Rev. Med. 65, 223-44 (2014)
3. Gottlieb, A. B Psoriasis: emerging therapeutic strategies Nat. Rev. Drug Discov 4, 19-34 (2005)
4. Lowes, M. A., Bowcock, A. M., Kruger, J. G. Pathogenesis and therapy of psoriasis Nature. 445, 866-873 (2007)
5. Pasparakis, M., Haase, I., Nestle, F. O. Mechanisms regulating skin immunity and inflammation. Nat. Rev. Immunol. 14, 289-301 (2014)
6. Taylor, P. C., Feldmann, M. Anti-TNF biologic agents: still the therapy of choice for rheumatoid arthritis. Nat. Rev. Rheumatol. 10, 578-82 (2009)
7. Chaudhari, U., Romano, P., Mulcahy, L. D, et al. Efficacy and safety of infliximab monotherapy for plaque-type psoriasis: a randomised trial. LANCET 357, 1842-1847 (2001)
8. Lowes, M. A., Russell, C. B., Martin, D. A., Towne, J. E., Krueger, J. G. The IL-23/T17 pathogenic axis in psoriasis is amplified by keratinocyte responses. Trends Immunol. 34, 174-81 (2013)
9. Kono, H., and Rock, K. L. How dying cells alert the immune system to danger. Nat. Rev. Immunol. 8, 279-89 (2008)

10. Sims, J. E., Smith, D. E., The IL-1 family: regulators of immunity. Nat. Rev. Immunol. 2, 89-102 (2010)
11. Lukens, J. R., Gross, J. M., Kanneganti, T. D. IL-1 family cytokines trigger sterile inflammatory disease. Front Immunol. 3, 315 (2012).
12. Dinarello, C. A. Immunological and inflammatory functions of the interleukin-1 family. Ann. Rev. Immunol. 27, 519-550 (2009)
13. Vigne, S., Palmer, G., Lammacchia, C., Martin, P., Talabot-Ayer, D., Rodriguez, E., Ronchi, F., Sallusto, F., Dinh, H., Sims, J. E., Gabay, C. IL-36R ligands are potent regulators of dendritic and T-cells. Blood 118, 5813-23 (2011)
14. Milovanovic, M., Volarevic, V., Radosavljevic, G., Jovanovic, I., Pejnovic, N., Arsenijevic, N., Lukic, M. L. IL-33/ST2 axis in inflammation and immunopathology. Immunologic Research 52, 89-99 (2012)
15. Towne, J. E., Sims, J. E. IL-36 in psoriasis. Curr. Opin. Pharmacol. 4, 486-90 (2012)
16. Farooq, M., Nakai, H., Fujimoto, A., Fujikawa, H., Matsuyama, A., Kariya, N., Aizawa, A., Fujiwara, H., Ito, M., Shimomura, Y. Mutation analysis of the IL36RN gene in 14 Japanese patients with generalized pustular psoriasis. Hum. Mutat. 34, 176-183 (2013)
17. Onoufriadis, A., Simpson, M. A., Pink, A. E., DiMeglio, P., Smith, C. H., Pullabhatla, V., Knight, J., Spain, S. L., Nestle, F. O., Burden, A. D., Capon, F., Trembath, R. C., et al. Mutations in IL36RN/IL1F5 are associated with the severe episodic inflammatory skin disease known as generalized pustular psoriasis. Am. J. Hum. Genet. 89, 432-437 (2011)
18. Kanazawa, N., Nakamura, T., Mikita, N., Furukawa, F. Novel IL-36RN mutation in a japanease case of early onset generalized pustular psoriasis. J Dermatol. 9, 749-51 (2013)
19. Johnston, A., Xing, X., Guzman, A. M., Riblett, M., Loyd, C. M., Ward, N. L., Wohn, C., Prens, E. P., Wang, F., Maier, L. E., Kang, S., Voorhees, J. J., Elder, J. T., Gudjonsson J. E. IL-1F5, -F6, -F8, -F9: a novel family signaling system that is active in psoriasis and promotes keratinocyte antimicrobial peptide expression. J. Immunol. 186, 2613-22 (2011)
20. Blumberg, H., Dinh, H., Trueblood, E. S., Pretorius, J., Kugler, D., Weng, N., Kanaly, S. T., Towne, J. E., Willis, C. R., Keuchle, M. K., Sims, J. E., Peschon, J. J. Opposing activities of two novel members of the IL-1 ligand family regulate skin inflammation. J. Exp. Med. 204, 2603-14 (2007)
21. Blumberg, H., Dinh, H., Dean, C. Jr., Trueblood, E. S., Bailey, K., Shows, D., Bhangavathula, N., Aslam, M. N., Varani, J., Towne, J. E., Sims, J. E. IL-1RL2 and its ligands contribute to the cytokine network in psoriasis. J. Immuno. 185, 4354-62 (2010)
22. Tortola, L., Rosenwald, E., Abel, B., Blumberg, H., Schafer, M., Coyle, A. J., Renauld, J. C., Werner, S., Kisielow, J., Kofp, M. Psoriasiform dermatitis is driven by IL-36-mediated D C-keratinocyte crosstalk. J Clin. Invest. 122, 3965-76 (2012)
23. Wu J K, Siller G, Strutton G. (2004). Psoriasis induced by topical imiquimod. Aust, J. Dermatol. 45, 47-50
24. Towne, J. E, Renshaw, B. R., Douangpanya, J., Lipsky, B. P., Shen, M., Gabel, C. A., Sims, J. E. Interleukin-36 (IL-36) ligands require processing for full agonist (IL-36a, IL-36b, IL-36g) or antagonist (IL-36Ra) activity. J. Biol. Chem. 286, 42594-602 (2011)
25. Hazuda, D, J., Strickler, J., Simon, P., Young, P. R. Structure-function mapping of interleukin 1 precursors. Cleavage leads to a conformational change in the mature protein. J. Biol. Chen. 266, 7081-7086 (1991)
26. Frank, O., Nestle, M. D., Daniel, H., Kaplan, M. D., Barker, M. D. Psoriasis. N. Engl. J. Med. 361, 496-508 (2009)
27. Koloaczakowska, E., Kubes, P. Neutrophil recruitment and function in health and inflammation. Nat. Rev. Immunol. 13, 159-75 (2013)
28. Hahn, I., Klaus, A., Janze, A. K., Steinwede, K., Ding, N., Bohling, J., Brumshagen, C., Serrano, H., Gauthier, F., Paton, J. C., Welte, T., Maus, U. A. Cathepsin G and neutrophil elastase play critical and nonredundant roles in lung-protective immunity against *Streptococcus pneumoniae* in mice. Infect. Immunl. 12, 4893-901 (2011)
29. Steinwede, K., Maus, R., Bohling, J., Voedisch, S., Braun, A., Ochs, M., Schmiedl, A., Langer, F., Gauthier, F., Roes, J., Welte, T., Bange, F. C., Niederweis, M., Buhling, F., Maus, U. A. Cathepsin G and neutrophil elastase contribute to lung-protective immunity against mycobacterial infections in mice. J. Immunol. 199, 4476-87 (2012)
30. Martin, S. J., Henry, C. M., Cullen, S. P. A perspective on mammalian caspases as positive and negative regulators of inflammation. Mol. Cell. 46, 387-97 (2012)
31. Weiss, G., Shemer, A., Trau, H. The Koebner phenomenon: review of the literature. JEADV. 16, 241-248 (2002)
32. Schechter, I and Berger, A. On the size of the active site in proteases. I. Papain. *Biochem Biophys Res Commun,* 27(2):157-162. (1967)
33. Schechter, I. and Berger, A. On the active site of proteases. 3. Mapping the active site of papain; specific peptide inhibitors of papain. *Biochem Biophys Res Commun,* 32(5):898-902. (1968)
34. Bruno, B. J., Miller, G. D., Lim, C. S. Basics and recent advances in peptide and protein drug delivery. Ther. Deliv. 4, 1443-67 (2013)
35. Powers J C[1], Asgian J L, Ekici O D, James K E. Irreversible inhibitors of serine, cysteine, and threonine proteases. Chem. Rev. 102, 4639-750. (2002)
36. Merrifield, R. B. Solid Phase Peptide Synthesis. I. The Synthesis of a Tetrapeptide J. Am. Chem. Soc., 85, 2149-2154 (1963)
37. Nilsson, B. L., Soellner, M. B., Raines, R. T. Chemical Synthesis of Proteins. Annu. Rev. Biophys. Biomol. Struct 2005; 34: 91-118 (2005)

The invention will now be described by the following numbered statements.

1. Use of an agent capable of inhibiting IL-36 proteolytic processing, including IL-36α, IL-36β and/or IL-36γ proteolytic processing, for the treatment and/or reduction of inflammation in a subject.
2. Use for the treatment according to statement 1 wherein the agent prevents the production of a biologically active IL-36 to prevent and/or reduce the pro-inflammatory effects of IL-36.
3. Use for the treatment according to statement 1 or 2 wherein the agent directly inhibits IL-36 proteolytic processing by either binding to one or more protease cleavage sites within IL-36 required for activation of IL-36 or competing with IL-36 activating protease(s) for binding to one or more protease cleavage sites within IL-36 required for activation of IL-36.
4. Use for the treatment according to statement 3 wherein the agent targets the protease cleavage sites within IL-36 and/or amino acid residues downstream and/or upstream of the cleavage site.

5. Use for the treatment according to statement 3 or statement 4 wherein the agent targets the IL-36β protease cleavage site NPQR$_5$ and/or one or more of upstream amino acid residues EAAP or the agent targets IL-36γ cleavage site GRAV$_{15}$ and/or one or more of upstream amino acid residues YQSM.
6. Use for the treatment according to statement 1 or 2 wherein the agent indirectly inhibits IL-36 proteolytic processing by preventing and/or inhibiting the activity of IL-36 activating proteases, or activators of IL-36 activating proteases, which proteolytically process IL-36.
7. Use for the treatment according to statement 6 wherein the IL-36 activating protease is selected from elastase, cathepsin G, cathepsin K or DPPI (Cathepsin C).
8. Use for the treatment according to any of the preceding statements wherein the agent is a small molecule, peptide, polypeptide, protein, siRNA, sgRNA, and/or antibody.
9. Use for the treatment according statement 6 wherein the peptide is at least a tripeptide or tetrapeptide or up to 8-10 peptide in length that binds the IL-36 activating protease and/or competes with IL-36 activating proteases for access to the IL-36 cleavage sites.
10. Use for the treatment according to statement 9 wherein the peptide is designed to mimic the protease cleavage sites within IL-36β and IL-36γ required for activation of IL-36 and bind the protease active site to inhibit its activity.
11. Use for the treatment according to statement 9 or statement 10 wherein the peptide is selected from one or more of the following:

Glu-Pro-Phe;

Ala-Phe-Leu-Phe;

Lys-Ala-Leu;

-continued

Glu-Pro-Phe-CMK;

Ala-Phe-Leu-Phe-CMK;

Lys-Ala-Leu-CMK,

Arg-Ala-Val,

Asp-Thr-Glu-Phe,

Ala-Pro-Leu,

Pro-Gln-Arg,

Arg-Pro-Leu or chemically modified derivatives thereof or combinations thereof.

12. Use for the treatment according to any of the preceding statements wherein the agent is a small molecule inhibitor of cathepsin G and elastase, including serine protease inhibitors, optionally selected from Boswellic Acids, cathepsin G inhibitor I, Elastase inhibitor IV, Sodium Fluoride, 4-(2-Aminoethyl) benzenesulfonyl fluoride hydrochloride (AEBSF.HCl), Aprotinin, Leupeptin, and/or phenylmethanesulfonylfluoride (PMSF).
13. Use for the treatment according to any of the preceding statements wherein the antibody is a polyclonal or monoclonal antibody raised against neutrophil-derived proteases, including the proteases elastase or cathepsin G or cathepsin K wherein the antibody binds to the protease to prevent its binding to the protease cleavage sites within IL-36 required for activation of IL-36.
14. Use according to any of the preceding statements for the treatment of inflammation of barrier organs in a subject, including inflammation of the skin, gut and/or lung, preferably inflammatory skin disorders, optionally selected from psoriasis, dermatitis and/or acne.
15. A composition, optionally a topical inflammatory skin disorder treatment, comprising an agent capable of inhibiting IL-36 proteolytic processing and a suitable pharmaceutical excipient.

The invention claimed is:

1. A method for the treatment of at least one inflammatory skin disorder selected from the group consisting of plaque psoriasis, guttate psoriasis, palmoplantar psoriasis, generalized pustular psoriasis, flexural psoriasis, inverse psoriasis, erythrodermic psoriasis, psoriasis vulgaris, and arthritic psoriasis, in a subject in need thereof, the method comprising:

administering to the subject an effective amount of at least one peptide, or a combination thereof, selected from the group consisting of:

a) a peptide consisting of 3 to 8 consecutive amino acids of SEQ ID NO:1, wherein the 3 to 8 consecutive amino acids comprises:

Asp-Pro-Gln-Arg (NPQR);

Pro-Gln-Arg (PQR);

Gln-Arg-Glu-Ala (QREA);

Asp-Pro-Gln-Arg (NPQR-CMK);

Pro-Gln-Arg (PQR-CMK);
or
Gln-Arg-Glu-Ala (QREA-CMK);

b) a peptide consisting of 3 to 8 consecutive amino acids of SEQ ID NO:2, wherein the 3 to 8 consecutive amino acids comprises:

Arg-Ala-Val (RAV);

Gly-Arg-Ala-Val (GRAV);

Ala-Val-Tyr-Gln (AVYQ);

Arg-Ala-Val (RAV-CMK);

Gly-Arg-Ala-Val (GRAV-CMK);
or
Ala-Val-Tyr-Gln (AVYQ-CMK);

c) a peptide consisting of 3 to 8 consecutive amino acids of SEQ ID NO:28, wherein the 3 to 8 consecutive amino acids comprises:

```
        Lys-Ala-Leu (KAL);
    or
        Lys-Ala-Leu (KAL-CMK);
``` and d) a peptide selected from the group consisting of:

```
        Ala-Leu-Ala (ALA);
        Met-Ala-Leu-Ala (MALA);
        Ala-Leu-Ala (ALA-CMK);
    and
        Met-Ala-Leu-Ala (MALA-CMK).
```

2. The method of claim 1, wherein the peptide is:

a peptide consisting of 3 to 8 consecutive amino acids of SEQ ID NO:1, or a combination thereof, wherein the 3 to 8 consecutive amino acids comprises:

```
        Asp-Pro-Gln-Arg (NPQR);
        Pro-Gln-Arg (PQR);
        Gln-Arg-Glu-Ala (QREA);
        Asp-Pro-Gln-Arg (NPQR-CMK);
        Pro-Gln-Arg (PQR-CMK);
    or
        Gln-Arg-Glu-Ala (QREA-CMK).
```

3. The method of claim 1, wherein the peptide is:

a peptide consisting of 3 to 8 consecutive amino acids of SEQ ID NO:2, or a combination thereof, wherein the 3 to 8 consecutive amino acids comprises:

```
        Arg-Ala-Val (RAV-CMK);
        Gly-Arg-Ala-Val (GRAV-CMK);
        Ala-Val-Tyr-Gln (AVYQ-CMK);
        Arg-Ala-Val (RAV);
        Gly-Arg-Ala-Val (GRAV);
    or
        Ala-Val-Tyr-Gln (AVYQ).
```

4. The method of claim 1, wherein the peptide is:

a peptide consisting of 3 to 8 consecutive amino acids of SEQ ID NO:28, or a combination thereof, wherein the 3 to 8 consecutive amino acids comprises:

```
        Lys-Ala-Leu (KAL);
    or
        Lys-Ala-Leu (KAL-CMK).
```

5. The method of claim 1, wherein the peptide is:

a peptide, or a combination thereof, selected from the group consisting of:

```
        Ala-Leu-Ala (ALA);
        Met-Ala-Leu-Ala (MALA);
        Ala-Leu-Ala (ALA-CMK);
        Met-Ala-Leu-Ala (MALA-CMK).
```

6. The method of claim 1, wherein the at least one inflammatory skin disorder is plaque psoriasis or psoriasis vulgaris.

7. The method of claim 1, wherein the at least one inflammatory skin disorder is guttate psoriasis.

8. The method of claim 1, wherein the at least one inflammatory skin disorder is palmoplantar psoriasis.

9. The method of claim 1, wherein the at least one inflammatory skin disorder is generalized pustular psoriasis.

10. The method of claim 1, wherein the at least one inflammatory skin disorder is flexural psoriasis.

11. The method of claim 1, wherein the at least one inflammatory skin disorder is inverse psoriasis.

12. The method of claim 1, wherein the at least one inflammatory skin disorder is erythrodermic psoriasis.

13. The method of claim 1, wherein the at least one inflammatory skin disorder is arthritic psoriasis.

14. The method of claim 1, wherein the administration is selected from the group consisting of topical, oral, parenteral, or intravenous.

\* \* \* \* \*